(12) United States Patent
Berger et al.

(10) Patent No.: US 9,321,724 B2
(45) Date of Patent: Apr. 26, 2016

(54) HETEROARYL COMPOUNDS WITH A-CYCLIC BRIDGING UNIT

(71) Applicant: Intervet Inc., Summit, NJ (US)

(72) Inventors: Michael Berger, Wiesbaden (DE); Marko Eck, Wiesbaden (DE); Christopher Kern, Edenkoben (DE)

(73) Assignee: Intervet Inc., Madison, NJ (US)

( * ) Notice: Subject to any disclaimer, the term of this patent is extended or adjusted under 35 U.S.C. 154(b) by 0 days.

(21) Appl. No.: 14/386,954

(22) PCT Filed: Mar. 27, 2013

(86) PCT No.: PCT/EP2013/056465
§ 371 (c)(1),
(2) Date: Sep. 22, 2014

(87) PCT Pub. No.: WO2013/144179
PCT Pub. Date: Oct. 3, 2013

(65) Prior Publication Data
US 2015/0057279 A1 Feb. 26, 2015

(30) Foreign Application Priority Data
Mar. 28, 2012 (EP) .................................. 12161718

(51) Int. Cl.
| | |
|---|---|
| C07D 207/34 | (2006.01) |
| C07D 213/74 | (2006.01) |
| C07D 215/38 | (2006.01) |
| C07D 277/42 | (2006.01) |
| A61K 31/4164 | (2006.01) |
| A61K 31/426 | (2006.01) |
| A61K 31/435 | (2006.01) |
| C07D 213/40 | (2006.01) |
| C07D 213/85 | (2006.01) |
| C07D 217/22 | (2006.01) |
| C07D 241/20 | (2006.01) |
| C07D 249/14 | (2006.01) |
| C07D 271/07 | (2006.01) |
| C07D 277/56 | (2006.01) |
| C07D 401/12 | (2006.01) |
| C07D 405/12 | (2006.01) |
| C07D 409/12 | (2006.01) |
| C07D 413/04 | (2006.01) |
| C07D 471/10 | (2006.01) |
| C07D 487/04 | (2006.01) |

(52) U.S. Cl.
CPC ............ *C07D 213/40* (2013.01); *C07D 207/34* (2013.01); *C07D 213/74* (2013.01); *C07D 213/85* (2013.01); *C07D 215/38* (2013.01); *C07D 217/22* (2013.01); *C07D 241/20* (2013.01); *C07D 249/14* (2013.01); *C07D 271/07* (2013.01); *C07D 277/42* (2013.01); *C07D 277/56* (2013.01); *C07D 401/12* (2013.01); *C07D 405/12* (2013.01); *C07D 409/12* (2013.01); *C07D 413/04* (2013.01); *C07D 471/10* (2013.01); *C07D 487/04* (2013.01)

(58) Field of Classification Search
None
See application file for complete search history.

(56) References Cited

U.S. PATENT DOCUMENTS

| | | | | |
|---|---|---|---|---|
| 4,663,333 | A | * | 5/1987 | Mueller et al. ................ 514/346 |
| 4,950,666 | A | | 8/1990 | Peake et al. |

FOREIGN PATENT DOCUMENTS

| | | |
|---|---|---|
| DE | 195 31 300 A1 | 2/1997 |
| JP | 57021370 A * | 2/1982 |
| WO | 9708231 A1 | 3/1997 |
| WO | 2007089455 A1 | 8/2007 |
| WO | 2012041873 A1 | 4/2012 |

OTHER PUBLICATIONS

Wu et al., Toxicology, 236, pp. 1-6, 2007.*
Tranlation of JP 57021370 (Feb. 1982).*
Fletcher et al., Bioorganic & Medicinal Chemistry (2007), 15(16), 5457-5479.*
Ruchkina, et al., "The Vinylogous Witkop Cyclisation", Tetrahedron Letters, 1999, pp. 8443-8445, vol. 40.
International Search Report for corresponding PCT Application No. PCT/EP2013/056465, mailed on May 17, 2013.
European Search Report for EP Application No. 12161718.7, mailed on Oct. 30, 2012.

* cited by examiner

*Primary Examiner* — Zinna Northington Davis

(57) ABSTRACT

This invention relates to certain heteroaryl compounds which may be used as medicaments, more specifically as medicaments for treating animals. The medicament can be used for the treatment of parasitic infections such as helminth infections and the treatment of parasitosis caused by such infections. This invention also relates to uses of the compounds to make medicaments and treatments comprising the administration of the compounds to animals in need of the treatments. This invention also relates to pharmaceutical compositions and kits comprising the compounds.

8 Claims, No Drawings

HETEROARYL COMPOUNDS WITH A-CYCLIC BRIDGING UNIT

CROSS-REFERENCE TO RELATED APPLICATIONS

This application is a national stage entry under 35 U.S.C. §371 of PCT/EP2013/056465, filed on Mar. 27, 2013, which claims priority to EP Application No. 12161718.7, filed on Mar. 28, 2012. The content of PCT/EP2013/056465 is hereby incorporated by reference in its entirety.

FIELD OF THE INVENTION

This invention relates to novel heteroaryl compounds that are useful as medicaments, more specifically as medicaments for animals, including non-human animals, and the preparation of such compounds. The medicament can preferably be used for the treatment of parasitic infections such as helminth infections and especially for the treatment of parasitoses, such as caused by helminth infections. This invention also relates to uses of the compounds to make medicaments and treatments comprising the administration of the compounds to animals in need of the treatments. Moreover this invention relates to pharmaceutical compositions and kits comprising the compounds.

BACKGROUND OF THE INVENTION

Parasitic diseases in animals cause substantial suffering and economic losses throughout the world. Thus, treatment of parasitic infections remains an important global endeavor. The causative organisms include helminths, such as nematodes, cestodes, and trematodes. These organisms can infect, for example, the stomach, intestinal tract, lymphatic system, muscle tissues, kidney, liver, lungs, heart, and brain of animals.

There are many known drugs (or "anthelmintic agents") available to treat various helminith parasite infections, see, e.g., McKellar, Q. A., et al., "Veterinary anthelmintics: old and new," *Review: Trends in Parasitology*, 20(10), 456-61 (October 2004). These anthelmintic agents treat specifically either nematode, cestode or trematode infections or have a broader anthelmintic spectrum. An example of an anthelmintic agent with sole effect on cestodes (tapeworms) is praziquantel. Some primary nematicidal compounds like fenbendazole, mebendazole, oxfendazole, albendazole have a broader spectrum than nematodes and treat cestode infections as well. Closantel, rafoxanide and triclabendazole are examples of specific compounds for the treatment of trematode infections (flukes).

While many parasitic infections can be treated with known drugs, evolutionary development of resistance by the parasites can render such drugs obsolete over time, see, e.g., Jabbar, A., et al., "Anthelmintic resistance: the state of play revisited," *Life Sciences*, 79, 2413-31 (2006). In addition, known drugs may have other deficiencies, such as limited spectrum of activity and the need for repeated treatments.

In WO 2008/028689 A1 certain N-(1-phtalazin-1-ylpiperidin-4-yl)amides are described as EP2 receptor modulators. WO 2008/028691 A1 discloses as EP2 receptors certain N-(1-hetaryl-piperidin-4-yl)(het)arylamides.

There still exists a need for new medicaments, such as antiparasitic agents to ensure safe, effective, and convenient treatment of a wide range of parasitic helminth infections over a long period of time.

SUMMARY OF THE INVENTION

Briefly, this invention relates to compounds that can in particular be used as a medicament for animals. The compounds correspond in structure to formula (I) or its pharmaceutically acceptable salts, solvates, N-oxides or prodrugs

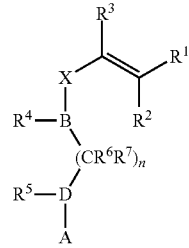

Formula I wherein
$R^1$ is hydrogen, halogen, alkyl, alkoxy, alkylthio, alkenyl, alkylcarbonyl, alkoxycarbonyl, alkynyl, alkylthioalkyl, alkoxyalkyl, $SF_5$, thiophenyl, imidazolyl, phenyl, furanyl wherein each of the carbon-containing radicals optionally is substituted by one or more halogen atoms, preferably fluorine atoms, $R^2$ is hydrogen, halogen, alkyl, alkoxy, alkylthio, alkenyl, alkylcarbonyl, alkoxycarbonyl, alkynyl, alkylthioalkyl, alkoxyalkyl, $SF_5$, thiophenyl, imidazolyl, phenyl, furanyl wherein each of the carbon-containing radicals optionally is substituted by one or more halogen atoms, preferably fluorine atoms, $R^3$ is hydrogen, halogen or alkyl, wherein each of the carbon atoms of the alkyl is optionally substituted by one or more halogen atoms, preferably fluorine atoms, preferably $R^3$ is hydrogen $R^4$ is hydrogen, alkyl or alkylcarbonyl, preferably $R^4$ is hydrogen $R^5$ is hydrogen, alkyl or alkylcarbonyl, preferably $R^5$ is hydrogen $R^6$ is hydrogen, alkyl, phenyl or benzyl, $R^7$ is hydrogen, alkyl, phenyl or benzyl, or $R^6$ is joined together with $R^4$ to form a $C_1$-$C_3$-alkylene group and $R^7$ is joined together with $R^5$ to form a $C_1$-$C_3$-alkylene group, wherein on or both of said $C_1$-$C_3$-alkylene groups are optionally substituted by one or more $C_1$-$C_3$-alkyl radicals, n is 1-3, X is CO, CS or $SO_2$, preferably X is CO, B, D is N or $CR^8$ wherein $R^8$ is hydrogen or alkyl, preferably hydrogen, at least one of B and D is N, preferably at least B is N and A is a heteroaryl, chosen from the group consisting of a 6 membered aromate according to formula II and a 5 membered heteroaromate according to formula III,

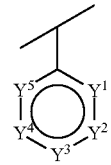

Formula II

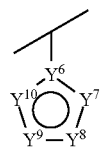

Formula III wherein in formula II:

$Y^1, Y^2, Y^4$ and $Y^5$ may be N or $CR^9$, wherein at least one and at most three of $Y^1, Y^2, Y^4$ and $Y^5$ is N, $Y^3$ is $CR^{10}$, $R^9$ is hydrogen, alkyl, alkoxy, alkylthio, halogen, nitrilo, nitro, alkylsulfonyl, alkylsulfoxyl, alkylcarbonyl, alkoxycarbonyl, aminocarbonyl, alkylaminocarbonyl, dialkylaminocarbonyl, aminosulfonyl, amino, alkylamino, dialkylamino, N-pyrrolidinyl, N-piperidinyl, N-morpholinyl, alkylcarbonylamino, phenyl wherein each of the carbon-containing radicals optionally is substituted by one or more halogen atoms, preferably fluorine atoms, $R^{10}$ is hydrogen, alkyl, alkoxy, alkylthio, halogen, nitrilo, nitro, alkylsulfonyl, alkylsulfoxyl, alkylcarbonyl, alkoxycarbonyl, aminocarbonyl, alkylaminocarbonyl, dialkylaminocarbonyl, aminosulfonyl, amino, alkylamino, dialkylamino, N-pyrrolidinyl, N-piperidinyl, N-morpholinyl, alkylcarbonylamino, phenyl wherein each of the carbon-containing radicals optionally is substituted by one or two halogen atoms, preferably fluorine atoms, $Y^1$ and $Y^2$ may form a ring system or $Y^2$ and $Y^3$ may form a ring system or $Y^3$ and $Y^4$ may form a ring system or $Y^4$ and $Y^5$ may form a ring system, and in formula III:

$Y^6$ is N or C, $Y^7, Y^8, Y^9$ and $Y^{10}$ is $CR^{11}$, $NR^{12}$, O or S, wherein at least one and at maximum three of $Y^7, Y^8, Y^9$ and $Y^{10}$ is $NR^{12}$, O or S, $R^{11}$ is hydrogen, alkyl, alkoxy, alkylthio, halogen, nitrilo, nitro, alkylcarbonyl, alkoxycarbonyl, aminocarbonyl, alkylaminocarbonyl, alkylsulfonyl, alkylsulfoxyl, dialkylaminocarbonyl, aminosulfonyl, amino, alkylamino, dialkylamino, N-pyrrolidinyl, N-piperidinyl, N-morpholinyl, alkylcarbonylamino, phenyl, wherein each of the carbon-containing radicals optionally is substituted by one or more halogen atoms, preferably fluorine atoms, $R^{12}$ is hydrogen, alkyl or missing, $Y^7$ and $Y^8$ may form a ring system or $Y^8$ and $Y^9$ may form a ring system or $Y^9$ and $Y^{10}$ may form a ring system.

The compounds of the formula (I) and pharmaceutically acceptable solvates, N-oxides, salts and prodrugs thereof are hereinafter together referred to as "compound(s) according to this invention". For these compounds, it is foreseen that $R^1$ and $R^2$ are not alkoxyalkyl.

If $R^6$ is joined together with $R^4$ to form a C1-C3 alkylene group and $R^7$ is joined together with $R^5$ to form a C1-C3 alkylene group a spiro compound is formed.

The integer n is from 1 to 3, and is preferably 2. If n is larger than 1 the $CR^6R^7$-groups can be identical or different.

The 6 or 5 membered aromatic group A of formula (I) represents a mono- or polycyclic ring system. A monocyclic ring system is obtained if for example the carbon/nitrogen atoms $Y^1, Y^2, Y^3, Y^4$ and $Y^5$ are unsubstituted or substituted but not joined together additionally to what is indicated in formula (I), in conjunction with formula (II) and (III). A polycyclic ring system is obtained if for example $Y^1$ and $Y^2$ are joined together, $Y^3$ and $Y^4$ are joined together or both $Y^1$ and $Y^2$ as well as $Y^3$ and $Y^4$ are joined together, etc.

A ring system formed by joining together neighbouring Y atoms is a saturated or non-saturated ring system (e.g. an aromatic ring system). The ring system itself is a monocyclic or polycyclic ring system, preferably a monocyclic, bicyclic or tricyclic, preferably a monocyclic or bicyclic ring system. The ring system contains from 4 to 10 ring atoms, preferably from 5 to 8 ring atoms, more preferably from 5 to 6 ring atoms, wherein the number of ring atoms includes the Y atoms The ring system optionally contains one or more, preferably one, two or three, more preferably one or two, ring heteroatoms, such as nitrogen, sulfur or oxygen. The ring system is unsubstituted or substituted, preferred substituents are one or more, preferably one, two or three, more preferably one or two, radicals selected from the group of $C_1$-$C_6$-alkyl, $C_1$-$C_6$-alkoxy, $C_1$-$C_6$-alkoxycarbonyl and $C_1$-$C_6$-alkylthio.

The mentioning of the preferred embodiments of the ring system formed by joining together neighbouring Y atoms is intended to disclose all combinations of the preferred embodiments, including but not limited to a saturated, monocyclic, bicyclic or tricyclic ring system with 4 to 10 ring atoms, one, two or three ring heteroatoms from the group of nitrogen, sulphur and oxygen, which is unsubstituted or substituted by one or two radicals from the group of $C_1$-$C_6$-alkyl, $C_1$-$C_6$-alkyloxy and $C_1$-$C_6$-alkylthio, or an unsaturated, monocyclic or bicyclic ring system with 5 to 6 ring atoms, one or two ring heteroatoms, which is unsubstituted, etc.

This invention is directed, in part, to a compound according to the invention and pharmaceutically acceptable solvates, N-oxides, salts and prodrugs thereof, which can be used as a medicament, preferably a medicament for animals for treating helminth infections. This invention also is directed, in part, to using at least one compound according to the invention and pharmaceutically acceptable solvates, N-oxides, salts and prodrugs thereof to prepare a medicament for treating an infection including diseases caused by such infections, in particular parasitoses caused by a helminth infection in animals.

This invention also is directed, in part, to pharmaceutical compositions, in particular anthelminitic compositions. The pharmaceutical compositions comprise a) at least one N-heteroaryl compound according to this invention, and b) at least one excipient, and/or at least one active compound (preferably anthelmintic compound) which differs in structure from the component a).

This invention also is directed, in part, to methods for treating a parasitic infection in animals, particularly a treatment of parasitoses caused by a helminth infection. The methods comprise administering at least one compound according to this invention to the animal.

This invention also is directed, in part, to a kit. The kit comprises at least one N-heteroaryl compound according to this invention. In addition, the kit comprises at least one other component, such as another ingredient (e.g., an excipient or active ingredient), and/or an apparatus for combining the compound with another ingredient, and/or an apparatus for administering the compound, and/or a diagnostic tool.

Further benefits of Applicants' invention will be apparent to one skilled in the art from reading this specification.

DETAILED DESCRIPTION OF PREFERRED EMBODIMENTS

In a preferred embodiment of a compound according to the invention $R^2$ is hydrogen, halogen or alkyl, wherein each of the carbon containing radical optionally is substituted by one or more halogen atoms, preferably fluorine atoms, in a more preferred embodiment $R^2$ is hydrogen; $R^3$ is hydrogen, halogen or alkyl, wherein each carbon containing radical optionally is substituted by one or more halogen atoms, preferably fluorine atoms, in a more preferred embodiment $R^3$ is hydrogen; $R^4$ is hydrogen, $R^5$ is hydrogen or alkyl, preferably hydrogen; $R^6$ is hydrogen, alkyl, phenyl, benzyl, preferably hydrogen; $R^7$ is hydrogen, alkyl, phenyl, benzyl, preferably hydrogen; and in formula II: one or two of $Y^1$, $Y^2$, $Y^4$ and $Y^5$ are N; $R^9$ is hydrogen, alkyl, alkoxy, alkylthio, halogen, nitrilo, nitro, alkylsulfonyl, alkylsulfoxyl, alkylcarbonyl, alkoxycarbonyl, aminocarbonyl, alkylaminocarbonyl, dialkylaminocarbonyl, amino, wherein each of the carbon-containing radicals optionally is substituted by one or more halogen atoms, preferably fluorine atoms; $R^{10}$ is hydrogen, alkyl, alkoxy, alkylthio, halogen, nitrilo, nitro, alkylsulfonyl, alkylsulfoxyl, alkylcarbonyl, alkoxycarbonyl, aminocarbonyl, alkylaminocarbonyl, dialkylaminocarbonyl, amino, wherein each of the carbon-containing radicals optionally is substituted by one or two halogen atoms, preferably fluorine atoms; and in formula III: $Y^9$ is $CR^{11}$; $R^{11}$ is hydrogen, alkyl, halogen, nitrilo, nitro, alkylcarbonyl, alkoxycarbonyl, aminocarbonyl, alkylaminocarbonyl, alkylsulfonyl, alkylsulfoxyl, dialkylaminocarbonyl, amino, wherein each of the carbon-containing radicals optionally is substituted by one or more halogen atoms, preferably fluorine atoms, and $R^{12}$ is missing.

In another embodiment $R^7$ is hydrogen or alkyl, and one of $Y^1$, $Y^2$, $Y^4$ and $Y^5$ is N. Preferably $R^1$ is hydrogen, chloro, propenyl, methylcarbonyl, methoxycarbonyl, propynyl, SF5, thiophenyl, imidazolyl, phenyl, furanyl, $C_1$-$C_4$ alkyl, C1-C2 alkoxy, C1-C2 alkylthio, C1-C2 alkoxy-C1-C2 alkyl, C1-C2 alkylthio-C1-C2 alkyl, each carbon containing radical optionally is substituted by one or more halogen atoms, preferably fluorine atoms; $R^2$ is hydrogen, chloro or C1-C2 alkyl; $R^3$ is hydrogen, or C1-C2 alkyl; $R^4$, $R^5$ is hydrogen; $R^6$ is hydrogen, C1-C2 alkyl, phenyl or benzyl; $R^7$ is hydrogen, C1-C2 alkyl; $R^9$ is hydrogen, C1-C2 alkyl, C1-C2 alkoxy, C1-C2 alkylthio; $R^{10}$ is hydrogen, C1-C2 alkyl, C1-C2 alkoxy, C1-C2 alkylthio; and $R^{11}$ is hydrogen or C1-C2 alkyl.

Preferably one of $Y^1$, $Y^2$, $Y^4$ and $Y^5$ is N.

In another embodiment A is a pyridine, thiazole, oxadiazole, thiophene, pyrazole, pyridazine, pyrazine, pyrimidine, imidazole or a quinoline. Preferably A is a pyridine, thiazole or an imidazole.

In a particular preferred embodiment the invention pertains to a compound having the structure of formula (IV), and pharmaceutically acceptable solvates, N-oxides, salts and prodrugs thereof,

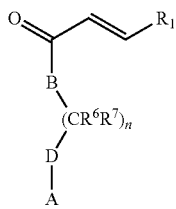

Formula (IV)

wherein
$R^1$ is hydrogen, halogen, alkyl, alkoxy, alkylthio, alkenyl, alkylcarbonyl, alkoxycarbonyl, alkynyl, alkylthioalkyl, alkoxyalkyl, $SF_5$ thiophenyl, imidazolyl, phenyl, furanyl wherein each of the carbon-containing radicals optionally is substituted by one or more halogen atoms, preferably fluorine atoms, $R^6$ is hydrogen, alkyl, phenyl or benzyl, preferably $R^6$ is hydrogen,
$R^7$ is hydrogen, alkyl, phenyl or benzyl, preferably $R^7$ is hydrogen,
B is N, and,
in formula II:
$Y^1$, $Y^2$, $Y^4$ and $Y^5$ may be N or $CR^9$, wherein at least one and at most three of $Y^1$, $Y^2$, $Y^4$ and $Y^5$ is N,
$Y^3$ is $CR^{10}$,
$R^9$ is hydrogen, alkyl, alkoxy, alkylthio, halogen, nitrilo, nitro, alkylsulfonyl, alkylsulfoxyl alkylcarbonyl, alkoxycarbonyl, aminocarbonyl, alkylaminocarbonyl, dialkylaminocarbonyl, aminosulfonyl, amino, alkylamino, dialkylamino, N-pyrrolidinyl, N-piperidinyl, N-morpholinyl, alkylcarbonylamino, phenyl wherein each of the carbon-containing radicals optionally is substituted by one or more halogen atoms, preferably fluorine atoms; preferably $R^9$ is hydrogen, alkyl, alkoxy, alkylthio, wherein each of the carbon-containing radicals optionally is substituted by one or more halogen atoms, preferably fluorine atoms
$R^{10}$ is hydrogen, alkyl, alkoxy, alkylthio, halogen, nitrilo, nitro, alkylsulfonyl, alkylsulfoxyl, alkylcarbonyl, alkoxycarbonyl, aminocarbonyl, alkylaminocarbonyl, dialkylaminocarbonyl, aminosulfonyl, amino, alkylamino, dialkylamino, N-pyrrolidinyl, N-piperidinyl, N-morpholinyl, alkylcarbonylamino, phenyl wherein each of the carbon-containing radicals optionally is substituted by one or two halogen atoms, preferably fluorine atoms, preferably $R^{10}$ is hydrogen, alkyl, alkoxy, alkylthio, wherein each of the carbon-containing radicals optionally is substituted by one or more halogen atoms, preferably fluorine atoms.
$Y^1$ and $Y^2$ may form a ring system or $Y^2$ and $Y^3$ may form a ring system or $Y^3$ and $Y^4$ may form a ring system or $Y^4$ and $Y^5$ may form a ring system,
and in formula III:
$Y^6$ is N or C,
$Y^7$, $Y^8$, $Y^9$ and $Y^{10}$ is $CR^{11}$, $NR^{12}$, O or S, wherein at least one and at maximum three of $Y^7$, $Y^8$, $Y^9$ and $Y^{10}$ is $NR^{12}$, O or S,
$R^{11}$ is hydrogen, alkyl, alkoxy, alkylthio, halogen, nitrilo, nitro, alkylcarbonyl, alkoxycarbonyl, aminocarbonyl, alkylaminocarbonyl, alkylsulfonyl, alkylsulfoxyl, dialkylaminocarbonyl, aminosulfonyl, amino, alkylamino, dialkylamino, N-pyrrolidinyl, N-piperidinyl, N-morpholinyl, alkylcarbonylamino, phenyl, wherein each of the carbon-containing radicals optionally is substituted by one or more halogen atoms, preferably fluorine atoms, preferably $R^{11}$ is hydrogen or alkyl which is optionally substituted by one or more halogen atoms, preferably fluorine atoms,
$R^{12}$ is hydrogen, alkyl or missing,
$Y^7$ and $Y^8$ may form a ring system or $Y^8$ and $Y^9$ may form a ring system or $Y^9$ and $Y^{10}$ may form a ring system.
Preferably B and D is N.

In another embodiment $R^1$ is hydrogen, chloro, C1-C4 alkyl (preferably C1-C2 alkyl), propenyl, methylcarbonyl, methoxycarbonyl, propynyl, SF5, thiophenyl, imidazolyl, phenyl, furanyl, C1-C2 alkoxy, C1-C2 alkylthio, C1-C2 alkoxy-C1-C2 alkyl, C1-C2 alkylthio-C1-C2 alkyl, each carbon containing radical optionally substituted by one or more halogen atoms, preferably fluorine. Preferably $R^1$ is C1-C4 alkyl, wherein each carbon containing radical is optionally substituted by one ore more fluorine atoms.

In another embodiment $R^6$, $R^7$ is hydrogen or C1-C2 alkyl, preferably hydrogen.

In yet another embodiment in formula II one or two of $Y^1$, $Y^2$, $Y^4$ and $Y^5$ are N; $R^9$ is hydrogen, alkyl, alkoxy, alkylthio, halogen, nitrilo, nitro, alkylsulfonyl, alkylsulfoxyl, alkylcarbonyl, alkoxycarbonyl, aminocarbonyl, alkylaminocarbonyl, dialkylaminocarbonyl, amino, wherein each of the carbon-containing radicals optionally is substituted by one or more halogen atoms, preferably fluorine atoms, preferably $R^9$ is hydrogen, alkyl, alkoxy, alkylthio, wherein each of the carbon-containing radicals optionally is substituted by one or more halogen atoms, preferably fluorine atoms; and $R^{10}$ is hydrogen, alkyl, alkoxy, alkylthio, halogen, nitrilo, nitro, alkylsulfonyl, alkylsulfoxy, alkylcarbonyl, alkoxycarbonyl, aminocarbonyl, alkylaminocarbonyl, dialkylaminocarbonyl, amino, wherein each of the carbon-containing radicals optionally is substituted by one or two halogen atoms, preferably fluorine atoms, preferably $R^9$ is hydrogen, alkyl, alkoxy, alkylthio, wherein each of the carbon-containing radicals optionally is substituted by one or two halogen atoms, preferably fluorine atoms; and in formula III $Y^9$ is $CR^{11}$; $R^{11}$ is hydrogen, alkyl, halogen, nitrilo, nitro, alkylcarbonyl, alkoxycarbonyl, aminocarbonyl, alkylaminocarbonyl, alkylsulfonyl, alkylsulfoxy, dialkylaminocarbonyl, amino, wherein each of the carbon-containing radicals optionally is substituted by one or more halogen atoms, preferably fluorine atoms, and $R^{12}$ is missing.

In a further embodiment, in formula II one of $Y^1, Y^2, Y^4$ and $Y^5$ is N.

In another embodiment A is a pyridine, thiazole, oxadiazole, thiophene, pyrazole, pyridazine, pyrazine, pyrimidine, imidazole or a quinoline. Preferably A is a pyridine, thiazole or an imidazole.

In another embodiment of any of the embodiments of the invention in formula II $Y^2$ and $Y^4$ are $CR^{12}$, and in formula III $R^{11}$ is hydrogen, alkyl, alkoxy, alkylthio, halogen, nitrilo, nitro, alkylcarbonyl, alkoxycarbonyl, aminocarbonyl, alkylaminocarbonyl, alkylsulfonyl, alkylsulfoxyll, dialkylaminocarbonyl, aminosulfonyl, alkylamino, dialkylamino, N-pyrrolidinyl, N-piperidinyl, N-morpholinyl, alkylcarbonylamino, phenyl, wherein each of the carbon-containing radicals optionally is substituted by one or more halogen atoms, preferably fluorine atoms.

In another embodiment A is a monocyclic ring system.

In still another embodiment of a compound according to the invention, $R^{10}$ is hydrogen, alkyl, alkoxy, alkylthio, haloalkyl, haloalkoxy, halogen, nitrilo, nitro, alkylsulfonyl, alkylsulfoxy, alkylcarbonyl, alkoxycarbonyl, aminocarbonyl, alkylaminocarbonyl, dialkylaminocarbonyl, aminosulfonyl, amino, alkylamino, dialkylamino, alkylcarbonylamino, phenyl wherein each of the carbon-containing radicals optionally is substituted by one or more halogen atoms, preferably fluorine atoms, and the compound is for the treatment of a parasitic infection of an animal, in particular a helminth infection of an animal.

The invention is also embodied in the use of a compound as defined hereabove for the manufacture of a medicament for the treatment of a parasitic infection of an animal. The invention is also embodied in an antiparasitic composition, wherein the composition comprises one or more compounds according to the invention and one or more pharmaceutically acceptable excipients and/or one or more pharmaceutically acceptable active ingredients which differ from the said one or more compounds according to the invention. In particular, the composition is used for the treatment of a parasitic infection of an animal. As such, the invention is also embodied in a kit which comprises as a component a) one or more compounds according to the invention, and as a component b) one or more other components selected from the group consisting of an excipient, an active ingredient, an apparatus for combining the compound of component a) with an excipient and/or active ingredient, an apparatus for administering the compound of component a) to an animal, and a diagnostic tool.

a) Salts, Solvates, N-oxides and Prodrugs

A salt of the compounds according to the invention may be advantageous due to one or more of the salt's physical properties, such as pharmaceutical stability in differing temperatures and humidities; crystalline properties; and/or a desirable solubility in water, oil, or other solvent. In some instances, a salt may be used as an aid in the isolation, purification, and/or resolution of the compound. Acid and base salts can typically be formed by, for example, mixing the compound with an acid or base, respectively, using various known methods in the art. To the extent a salt of the compound is intended to be administered in vivo (i.e. to an animal) for a therapeutic benefit, the salt is pharmaceutically acceptable.

Salts may also be of advantage in the synthesis of the compounds according to this invention. For instance certain intermediates may advantageously be used in form of their salts in the preparation process of the compounds according to this invention.

In general, an acid addition salt can be prepared by reacting a free base compound with an approximately stoichiometric amount of an inorganic or organic acid. Examples of often suitable inorganic acids for making (pharmaceutically acceptable) salts include hydrochloric, hydrobromic, hydroiodic, nitric, carbonic, sulfuric, and phosphoric acid. Examples of often suitable organic acids for making (pharmaceutically acceptable) salts generally include, for example, aliphatic, cycloaliphatic, aromatic, araliphatic, heterocyclic, carboxylic, and sulfonic classes of organic acids. Specific examples of often suitable organic acids include cholic, sorbic, lauric, acetic, trifluoroacetic, formic, propionic, succinic, glycolic, gluconic, digluconic, lactic, malic, tartaric acid, citric, ascorbic, glucuronic, maleic, fumaric, pyruvic, aspartic, glutamic, aryl carboxylic acid (e.g., benzoic), anthranilic acid, mesylic, stearic, salicylic, p-hydroxybenzoic, phenylacetic, mandelic, embonic (pamoic), alkylsulfonic (e.g., ethanesulfonic), arylsulfonic (e.g., benzenesulfonic), pantothenic, 2-hydroxyethanesulfonic, sulfanilic, cyclohexylaminosulfonic, β-hydroxybutyric, galactaric, galacturonic, adipic, alginic, butyric, camphoric, camphorsulfonic, cyclopentanepropionic, dodecylsulfic, glycoheptanoic, glycerophosphic, heptanoic, hexanoic, nicotinic, 2-naphthalesulfonic, oxalic, palmoic, pectinic, 3-phenylpropionic, picric, pivalic, thiocyanic, tosylic, and undecanoic acid. In some such embodiments, for example, the salt comprises a trifluoroacetate, mesylate, or tosylate salt. In other embodiments, the salt comprises a hydrochloric acid salt.

In general, a base addition salt can be prepared by reacting a free acid compound with an approximately stoichiometric amount of an inorganic or organic base. Examples of base addition salts may include, for example, metallic salts and organic salts. Metallic salts, for example, include alkali metal (group Ia) salts, alkaline earth metal (group IIa) salts, and other physiologically acceptable metal salts. Such salts may be made from aluminum, calcium, lithium, magnesium, potassium, sodium, and zinc. For example, a free acid compound may be mixed with sodium hydroxide to form such a base addition salt. Organic salts may be made from amines, such as trimethylamine, diethylamine, N,N'-dibenzylethylenediamine, chloroprocaine, ethanolamine, diethanolamine, ethylenediamine, meglumine (N-methylglucamine), and procaine. Basic nitrogen-containing groups may be quaternized with agents such as $C_1$-$C_6$-alkyl halides (e.g., methyl, ethyl, propyl, and butyl chlorides, bromides, and iodides), dialkyl sulfates (e.g., dimethyl, diethyl, dibuytl, and diamyl sulfates), long chain halides (e.g., decyl, lauryl, myristyl, and stearyl chlorides, bromides, and iodides), arylalkyl halides (e.g., benzyl and phenethyl bromides), and others.

A solvate of a compound according to the invention may be formed by aggregation of said compound according to the invention with solvent molecules such as water, alcohols, for example ethanol, aromatic solvents such as toluene, ethers, halogenated organic solvents such as dichloromethane, preferably in a definite proportion by weight.

An N-oxide of a compound according to the invention may be formed by oxidation of an N-atom in an amine or N-heterocycle such as pyridine by oxidation agents such as hydrogen peroxide, peracids or inorganic oxidation agents such as potassium peroxymonosulfate (oxone). In preferred N-oxides a nitrogen atom in the group of formula II or III is oxidized, more preferred are N-oxides wherein the nitrogen atom in the group of formula II oxidized giving, for example, a pyridine N-oxide, if one $Y^1$, $Y^2$, $Y^3$ or $Y^4$ is N.

This invention also encompasses prodrug derivatives of the compounds according to the invention The term prodrug refers to compounds that are transformed in vivo to yield the parent compound according to the invention. In vivo means that in the case of, for example, treatment of a parasitic infection this transformation can occur in the host organism and/or the parasite. Various forms of prodrugs are well known in the art. For example, if the group of formula (II) represents a pyridine, it is possible to form pyridinium salts such as, for example, acyloxyalkylpyridinium salts, which can offer advantages in terms of higher solubility for parenteral dosage forms, which are described in S. K. Davidsen et al., *J. of Med. Chem.* 37 4423-4429 (1994). Other examples of possible prodrugs are compounds that form the double bond present in formulae I and IV by elimination from a saturated precursor compound:

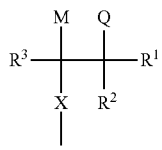

Elimination of MQ will generate compounds of formula I or IV. If M is hydrogen, this type of elimination is also known in the art as retro-Michael reaction or retro-Michael addition. Examples of such retro-Michael reactions that occur in vivo to generate unsaturated compounds are described in, for example, S. C. Alley, *Bioconjugate Chem.* 19, 759-765 (2008); D. Lopez, *Abstracts of Papers*, 231$^{st}$ *National Meeting*, Atlanta, Ga., United States, Mar. 26-30, 2006, MEDI-292.

b) Isomers

The compounds according to this invention and their intermediates may exist in various isomeric forms. A reference to a compound according to this invention or an intermediate thereof always includes all possible isomeric forms of such compound.

In some embodiments, a compound according to this invention may have two or more isomers, such as optical isomers or conformational isomers. For example, the compounds can have a (E) or (Z) configuration at the —$CXR^3$=$CR^1R^2$ double bond. In some preferred embodiments, such compound has the (E) configuration, in other embodiments, the compound has the (Z) configuration. In a preferred embodiment the compounds have (E) configuration. For instance the compounds of formula (IV) and the compounds of Tables B, C and D and most of the compounds of table A below exhibit (E) configuration.

Unless otherwise stated, a compound structure that does not indicate a particular conformation is intended to encompass compositions of all the possible conformational isomers of the compound, as well as compositions comprising fewer than all the possible conformational isomers. In some embodiments, the compound is a chiral compound. In some embodiments, the compound is a non-chiral compound.

Treatment Methods Using Compounds According to this Invention

The compounds according to the invention and pharmaceutically acceptable solvates, N-oxides, salts and prodrugs thereof are for use as a medicament for animals. In some embodiments of this invention, one or more, preferably one compound according to this invention is administered to treat infections, in particular a helminth infection of an animal. In one embodiment one or more, preferably one compound according to this invention is administered to treat parasitoses of an animal.

The term "(parasitic) infection" includes conditions associated with or caused by one or more (parasitic) pathogens; said conditions include clinical conditions (parasitoses) and sub-clinical conditions. The term "treatment of parasitic infection" thus includes both the treatment of parasitoses and the treatment of sub-clinical conditions. The treatment of a parasite infection generally implies the suppression of parasite (e.g. helminth) burdens in the animal below that level at which economic loss occurs.

Sub-clinical conditions are typically conditions not directly leading to clinical symptoms in the parasite infected animal but leading to economic losses. Such economic losses can be e.g. by depression of growth in young animals, lower feed efficiency, lower weight gain in meat producing animals, lower milk production in ruminants, lower egg production in laying hens, or lower wool-production in sheep.

The term "parasitoses" relates to clinically manifest pathologic conditions and diseases associated with or caused by an infection by one or more parasites, such as, for example parasitic gastroenteritis or anemia in ruminants e.g. sheep and goats or colic in horses.

In general, the prevention or treatment of parasitic infection including parasitoses is achieved by administering one or more, preferably one compound according to this invention to treat a parasitic infection such as a helminth infection.

Thus the invention provides a method of treating a (parasitic) infection such as a helminth infection, including parasitoses, which comprises administering to the animal an antiparasitically, preferably an anthelmintically, effective amount of one or more compounds according to this invention. Preferably nematode, cestode or trematode infections are treated, more preferably nematode infections.

"Treating (parasitic) infections" includes treating parasitoses and means to partially or completely inhibit the development of (parasitic) infections of an animal susceptible to (parasitic) infection, reduce or completely eliminate the symptoms of infections of an animal having infections, and/or partially or completely cure infections of an animal having infections. This can be achieved by alleviating or reducing pathogen numbers such as parasite numbers in an animal.

The effect of the compounds according to this invention can be e.g. ovicidal, larvicidal, and/or adulticidal or a combination thereof. The effect can manifest itself directly, i.e. killing the parasites either immediately or after some time has elapsed, for example when molting occurs, or by destroying their eggs, or indirectly, e.g. reducing the number of eggs laid and/or the hatching rate. Alternatively the parasite is not killed but paralyzed and is then dislodged and excreted by the host animal.

In another aspect the present invention thus provides a pharmaceutical composition comprising an anthelmintically effective amount of one or more, preferably one compound according to this invention and one or more pharmaceutically acceptable excipients.

The compounds and pharmaceutical compositions according to this invention are useful in treating parasitic infections such as helminth infections of animals. An "effective amount," is the amount or quantity of a compound that is required to alleviate or reduce parasite numbers in an animal, and/or to inhibit the development of parasite infections in an animal, in whole or in part.

This amount is readily determined by observation or detection of the pathogen numbers such as parasite numbers both before and after contacting the sample of pathogens such as parasites including their stages with the compound according to this invention, directly and/or indirectly, e.g., by contacting articles, surfaces, foliage, or animals with the compound e.g. the parasite count is reduced, after a first administration, by an amount ranging from 5% to about 100%.

This can be evaluated by counting parasites (especially helminthes) directly after necroscopy of the host animal.

The reduction of parasite numbers, especially gastrointestinal helminth parasites can be alternatively measured indirectly by faecal egg or differential larval counts. In this case the effective amount of the compound is determined by the reduction of the number of excreted helminth eggs or larvae in the faeces of the treated animal before and after treatment. For an in vivo administration the compound according to this invention, is preferably administered to an animal in an effective amount which is synonymous with "pharmaceutically effective amount" or "anthelmintically effective amount".

A single administration of a compound according to this invention is typically sufficient to treat a parasitic infection such as a helminth infection, preferably a nematode, cestode or trematode infection, more preferably a nematode infection. Although such a single dose is typically preferred, it is contemplated that multiple doses can be used. When the compound according to this invention is orally administered, the total dose to treat a disease such as a helminth infection is generally greater than about 0.01 mg/kg (i.e., milligram of compound according to this invention per kilogram body weight of the treated animal). In some such embodiments, the total dose is from about 0.01 to about 100 mg/kg, from about 0.01 to about 50 mg/kg, from about 0.1 to about 25 mg/kg, or from about 1 to about 20. For sheep, for example, the dose is generally from about 0.5 to about 15 mg/kg, from about 1 to about 10 mg/kg. The same dose range may be suitable for other dosage routes. For example, in some embodiments, the same dose range is used for subcutaneous administration. The desired dose, however, may be less in some instances where the compound according to this invention is administered intravenously.

If the compound according to this invention is administered parenterally via an injection, the concentration of the compound according to this invention in the dosage form preferably is sufficient to provide the desired therapeutically effective amount of the compound according to this invention in a volume that is acceptable for parenteral administration.

Factors affecting the preferred dosage may include, for example, the parasite species infection to be treated and the development stages of the parasites, the type (e.g., species and breed), age, size, sex, diet, activity, and condition of the of the infected animal; the dosage route; pharmacological considerations, such as the activity, efficacy, pharmacokinetic, and toxicology profiles of the particular composition administered; and whether the compound according to this invention being administered as part of a combination of active ingredients. Thus, the preferred amount of the compound according to this invention can vary, and, therefore, can deviate from the typical dosages set forth above. Determining such dosage adjustments is generally within the skill of those in the art.

In a preferred embodiment the compounds according to this invention are used to treat a helminth infection caused by one or more helminths selected from the group consisting of a) cestodes: e.g. *Anaplocephala* spp.; *Dipylidium* spp.; *Diphyllobothrium* spp.; *Echinococcus* spp.; *Moniezia* spp.; *Taenia* spp.; b) trematodes e.g. *Dicrocoelium* spp.; *Fasciola* spp.; *Paramphistomum* spp.; *Schistosoma* spp.; or c) nematodes, e.g.; *Ancylostoma* spp.; *Anecator* spp.; *Ascaridia* spp.; *Ascaris* spp.; *Brugia* spp.; *Bunostomum* spp.; *Capillaria* spp.; *Chabertia* spp.; *Cooperia* spp.; *Cyathostomum* spp.; *Cylicocyclus* spp.; *Cylicodontophorus* spp.; *Cylicostephanus* spp.; *Craterostomum* spp.; *Dictyocaulus* spp.; *Dipetalonema* spp; *Dirofilaria* spp.; *Dracunculus* spp.; *Enterobius* spp.; *Filaroides* spp.; *Habronema* spp.; *Haemonchus* spp.; *Heterakis* spp.; *Hyostrongylus* spp.; *Metastrongylus* spp.; *Meullerius* spp. *Necator* spp.; *Nematodirus* spp.; *Nippostrongylus* spp.; *Oesophagostomum* spp.; *Onchocerca* spp.; *Ostertagia* spp.; *Oxyuris* spp.; *Parascaris* spp.; *Stephanurus* spp.; *Strongylus* spp.; *Syngamus* spp.; *Toxocara* spp.; *Strongyloides* spp.; *Teladorsagia* spp.; *Toxascaris* spp.; *Trichinella* spp.; *Trichuris* spp.; *Trichostrongylus* spp.; *Triodontophorous* spp.; *Uncinaria* spp., and/or *Wuchereria* spp.;

It is contemplated that the compounds according to this invention may be used to treat animals, including humans and non-human animals, especially non-human mammals. Such non-human mammals include, for example, livestock mammals (e.g., swine, livestock ruminats like bovines, sheep, goats, etc.), laboratory mammals (e.g., mice, rats, jirds, etc.), companion mammals (e.g., dogs, cats, equines, etc.), and wild and zoo mammals (e.g., buffalo, deer, etc.). It is contemplated that the compounds according to this invention also are suitable to treat non-mammals, such as poultry (e.g., turkeys, chickens, ducks, etc.) and fish (e.g., salmon, trout, koi, etc.).

In some embodiments, one or more, preferably one compound according to this invention is used to treat an infection by a helminth, such as a nematode, cestode or trematode, preferably a nematode (such as *Haemonchus contortus*), that is resistant to one or more other anthelmintic agents. In some embodiments, the compound according to this invention is active against a helminth, such as a nematode, cestode or trematode, preferably a nematode such as *Haemonchus contortus*, that is resistant to one or more of the following anthelmintics: an avermectin (e.g., ivermectin, selamectin, doramectin, abamectin, and eprinomectin); a milbemycin (moxidectin and milbemycin oxime); a pro-benzimidazole (e.g., febantel, netobimin, and thiophanate); a benzimidazole derivative, such as a thiazole benzimidazole derivative (e.g., thiabendazole and cambendazole) or a carbamate benzimidazole derivative (e.g., fenbendazole, albendazole (oxide), mebendazole, oxfendazole, parbendazole, oxibendazole, flubendazole, and triclabendazole); an imidazothiazole (e.g., levamisole and tetramisole); a tetrahydropyrimidine (morantel and pyrantel), an organophosphate (e.g., trichlorphon, haloxon, dichlorvos, and naphthalophos); a salicylanilide (e.g., closantel, oxyclozanide, rafoxanide, and niclosamide); a nitrophenolic compound (e.g., nitroxynil and nitroscanate); benzoenedisulphonamide (e.g., clorsulon); a pyrazinaisoquinoline (e.g., praziquantel and epsiprantel); a heterocyclic compound (e.g., piperazine, diethylcarbamazine, dichlorophen, and phenothiazine); an arsenical (e.g., thiacetarsamide, melorsamine, and arsenamide); cyclooctadepsipeptide (e.g., emodepside); and a paraherquamide.

In some such embodiments, for example, the compound according to this invention is active against a helminth (for example, *Haemonchus contortus*) resistant to an avermectin, such as ivermectin. In other embodiments, the compound according to this invention is alternatively or additionally active against a helminth (for example, *Haemonchus contortus*) resistant to a benzimidazole derivative, such as fenbendazole. In other embodiments, the compound according to this invention is alternatively or additionally active against a helminth (for example, *Haemonchus contortus*) resistant to levamisole. And, in other embodiments, the compound according to this invention is alternatively or additionally active against a helminth (for example, *Haemonchus contortus*) resistant to pyrantel.

The compounds according to this invention may be administered in various dosage forms. The term "dosage form" means that the compounds according to this invention are formulated into a product suitable for administering to the animal via the envisaged dosage route. Such dosage forms are sometimes referred to herein as formulations or pharmaceutical composition.

The formulation type chosen for a dosage form in any instance will depend upon the particular purpose envisaged and the physical, chemical and biological properties of the compound according to this invention.

Dosage forms useful in the current invention can be liquid, semi-solid or solid dosage forms.

Liquid dosage forms of the compounds are generally solutions, suspensions or emulsions. A solution is a mixture of two or more components that form a single phase that is homogeneous down to the molecular level. A suspension consists of insoluble solid particles dispersed in a liquid medium, with the solid particles accounting for about 0.5% to about 30% of the suspension. The liquid may be aqueous, oily, or both. An emulsion is a heterogeneous dispersion of one immiscible liquid in another; it relies on an emulsifying agent for stability. A dry powder (or granule) for reconstitution is reconstituted as a solution or as a suspension immediately prior to injection. The principal advantage of this dosage form is that it overcomes the problem of instability in solution or suspension.

One possible dosage route is the oral dosage route, wherein the compound according to this invention is administered via the mouth. Oral dosage forms suitable for oral administration comprise liquids (e.g. drench or drinking water formulations), semi-solids (e.g. pastes, gels), and solids (e.g. tablets, capsules, powders, granules, chewable treats, premixes and medicated blocks).

A drench is a liquid oral formulation that is administered directly into the mouth/throat of an animal, especially a livestock animal, by means of a "drench gun" or syringe or another suitable device. When the composition is administered in the animal recipient's drinking water or as a drench, it may be convenient to use a solution or suspension formulation. This formulation can be, for example, a concentrated suspension that is mixed with water or a dry preparation that is mixed and suspended in the water.

Semi-solid oral formulations (pastes or gels) are generally administered via an applicator directly into the mouth of an animal or mixed with the feed.

Solid oral formulations are either administered directly to an animal (tablet, capsule) or mixed with the feed or via medicated feed blocks.

When the oral formulation is administered via a non-human animal's feed, it may, for example, be fed as a discrete feed or as a chewable treat. Alternatively (or additionally), it may, for example, be intimately dispersed in the animal recipient's regular feed, used as a top dressing, or in the form of solid pellets, paste or liquid that is added to the finished feed. When the oral formulation is administered as a feed additive, it may be convenient to prepare a "premix" in which the oral formulation is dispersed in a liquid or solid carrier. This "premix" is, in turn, dispersed in the animal's feed using, for example, a conventional mixer.

Several modified-release delivery systems have been developed, that take advantage of the unique anatomy of the ruminant forestomach, i.e. for intra-ruminal administration. An intraruminal bolus is a specific formulation for ruminants (cattle, sheep, goats, buffalos, camelids, deer etc). It is a veterinary delayed release delivery system which remains in the rumeno-reticular sac of a ruminant animal over an extended period of time and in which the therapeutically active substance has a predictable and delayed release pattern. Such intraruminal boluses are usually administered using a balling gun or another suitable device.

It is contemplated that the compounds according to this invention may alternatively be administered via non-oral dosage routes, such as topically (e.g., via a spot-on, pour-on or transdermal patch), or parenterally (e.g., subcutaneous injection, intravenous injection, intramuscular injection, etc.).

For instance the compounds according to this invention may be administered topically using a transdermal formulation (i.e. a formulation that passes through the skin). Alternatively the compounds according to this invention may be administered topically via the mucosa.

Topical dosage forms suitable for topical administration comprise liquids (e.g. bath, spray, spot-on), semi-solids (e.g. creams, gels), and solids (e.g. patches, powders, collars). Typical topical formulations for animals are liquid or semi-liquid dosage forms. Typical formulations for transdermal and mucosal administration include, for example, pour-ons, spot-ons, dips, sprays, mousses, shampoos, powders, gels, hydrogels, lotions, solutions, creams, ointments, dusting powders, dressings, foams, films, skin patches, limb bands, collars, ear tags, wafers, sponges, fibers, bandages, and microemulsions. When a liquid formulation is used topically on skin, it can be administered by, for example, pouring on (pour-on or spot-on), spreading, rubbing, atomizing, spraying, dipping, bathing, or washing.

The pour-on or spot-on methods, for example, comprise applying the formulation to a specific location of the skin or coat, such as on the neck or backbone of the animal. This may be achieved by, for example, applying a swab or drop of the pour-on or spot-on formulation to a relatively small area of the recipient animal's skin or coat (i.e., generally no greater than about 10% of the animal recipient's skin or coat). In some embodiments, the compound according to this invention is dispersed from the application site to wide areas of the fur due to the spreading nature of the components in the formulation and the animal's movements while, in parallel, being absorbed through the skin and distributed via the animal recipient's fluids and/or tissues.

Parenteral formulations and delivery systems for non-oral routes comprise liquids (e.g. solutions, suspensions, emulsions, and dry powders for reconstitution), semi-solids and solids (e.g. implants). The majority of implants that are used in veterinary medicine are compressed tablets or dispersed matrix systems in which the drug is uniformly dispersed within a nondegradable polymer or alternatively extrusion products.

Pharmaceutical Compositions

This invention also is directed to pharmaceutical compositions (or medicaments) comprising one or more, preferably one compound according to this invention. The compositions also may (and preferably will) comprise one or more pharmaceutically acceptable excipients.

Pharmaceutical compositions of the present invention may be manufactured by, for example, processes known in the art. These processes include, for example, a variety of known mixing, dissolving, granulating, emulsifying, encapsulating, entrapping, and lyophilizing processes. Optimal formulation depends on, for example, the dosage route (e.g. oral, injection, topical).

Solid dosage forms, for example, may be prepared by, for example, intimately and uniformly mixing the compounds with fillers, binders, lubricants, glidants, disintegrants, flavoring agents (e.g., sweeteners), buffers, preservatives, pharmaceutical-grade dyes or pigments, and controlled release agents.

Oral dosage forms other than solids may be prepared by mixing the compounds with, for example, one or more solvents, viscosity-enhancing agents, surfactants, preservatives, stabilizers, resins, fillers, binders, lubricants, glidants, disintegrants, co-solvents, sweeteners, flavorings, perfuming agents, buffers, suspending agents, and pharmaceutical-grade dyes or pigments.

Contemplated binders include, for example, gelatin, acacia, and carboxymethyl cellulose.

Contemplated lubricants include, for example, magnesium stearate, stearic acid, and talc.

Contemplated disintegrants include, for example, corn starch, alginic acid, sodium carboxymethylcellulose, and sodium croscarmellose.

Contemplated buffers include, for example, sodium citrate, and magnesium and calcium carbonate and bicarbonate.

Contemplated solvents include, for example, water, petroleum, animal oils, vegetable oils, mineral oil, and synthetic oil. Physiological saline solution or glycols (e.g., ethylene glycol, propylene glycol, or polyethylene glycol) also may be included. The solvent preferably has sufficient chemical properties and quantity to keep the compounds solubilized at temperatures in which the composition is stored and used.

Contemplated viscosity-enhancing agents include, for example, polyethylene, methylcellulose, sodium carboxymethylcellulose, hydroxypropyl-methylcellulose, hydroxypropylcellulose, sodium alginate, carbomer, povidone, acacia, guar gum, xanthan gum, tragacanth, methylcellulose, carbomer, xanthan gum, guar gum, povidone, sodium carboxymethylcellulose, magnesium aluminum silicate, carboxyvinyl polymers, carrageenan, hydroxyethyl cellulose, laponite, water-soluble salts of cellulose ethers, natural gums, colloidal magnesium aluminum silicateor finely divided silica, homopolymers of acrylic acid crosslinked with an alkyl ether of pentaerythritol or an alkyl ether of sucrose, and carbomers.

Contemplated surfactants include, for example, polyoxyethylene sorbitan fatty acid esters; polyoxyethylene monoalkyl ethers; sucrose monoesters; lanolin esters and ethers; alkyl sulfate salts; and sodium, potassium, and ammonium salts of fatty acids.

Contemplated preservatives include, for example, phenol, alkyl esters of parahydroxybenzoic acid (e.g., methyl p-hydroxybenzoate (or "methylparaben") and propyl p-hydroxybenzoate (or "propylparaben")), sorbic acid, o-phenylphenol benzoic acid and the salts thereof, chlorobutanol, benzyl alcohol, thimerosal, phenylmercuric acetate and nitrate, nitromersol, benzalkonium chloride, and cetylpyridinium chloride.

Contemplated stabilizers include, for example, chelating agents and antioxidants.

Solid dosage forms also may comprise, for example, one or more excipients to control the release of the compounds. For example, it is contemplated that the compounds may be dispersed in, for example, hydroxypropylmethyl cellulose. Some oral dosage forms (e.g., tablets and pills) also may be prepared with enteric coatings.

Topical dosage route uses, for example, a concentrated liquid or semi-liquid solution, suspension (aqueous or non-aqueous), emulsion (water-in-oil or oil-in-water), or microemulsion comprising a compounds dissolved, suspended, or emulgated in a pharmaceutically-acceptable liquid vehicle. In such embodiments, a crystallization inhibitor optionally may generally be present.

Such a pour-on or spot-on formulation can be prepared by dissolving, suspending, or emulsifying the compounds in a suitable skin-fitted solvent or solvent mixture. Other excipients may be included as well, such as, for example, a surfactant, colorant, antioxidant, stabilizer, adhesive, etc. Contemplated solvents include, for example, water, alkanol, glycol, polyethylene glycol, polypropylene glycol, glycerin, benzyl alcohol, phenylethanol, phenoxyethanol, ethyl acetate, butyl acetate, benzyl benzoate, dipropylene glycol monomethyl ether, diethylene glycol monobutyl ether, acetone, methyl ethyl ketone, aromatic and/or aliphatic hydrocarbons, vegetable or synthetic oil, DMF, liquid paraffin, silicone, dimethylacetamide, N-methylpyrrolidone, or 2,2-dimethyl-4-oxy-methylene-1,3-dioxolane.

In some embodiments, a topical formulation (particularly a pour-on or spot-on formulation) comprises a carrier that promotes the absorption or penetration of the compounds through the skin into the blood stream, other bodily fluids (lymph), and/or body tissue (fat tissue). Contemplated examples of dermal penetration enhancers include, for example, dimethylsulfoxide, isopropyl myristate, dipropylene glycol pelargonate, silicone oil, aliphatic esters, triglycerides, and fatty alcohols.

Topical formulations also (or alternatively) may comprise, for example, one or more spreading agents. These substances act as carriers that assist in distributing an active ingredient over the animal recipient's coat or skin. They may include, for example, isopropyl myristate, dipropylene glycol pelargonate, silicone oils, fatty acid esters, triglycerides, and/or fatty alcohols. Various spreading oil/solvent combinations also may be suitable, such as, for example, oily solutions, alcoholic and isopropanolic solutions (e.g., solutions of 2-octyl dodecanol or oleyl alcohol), solutions of esters of monocarboxylic acids (e.g., isopropyl myristate, isopropyl palmitate, lauric acid oxalic ester, oleic acid oleyl ester, oleic acid decyl ester, hexyl laurate, oleyl oleate, decyl oleate, and caproic acid esters of saturated fatty alcohols having a carbon chain of 12 to 18 carbons), solutions of esters of dicarboxylic acids (e.g., dibutyl phthalate, diisopropyl isophthalate, adipic acid diisopropyl ester, and di-n-butyl adipate), or solutions of esters of aliphatic acids (e.g., glycols). When the formulation comprises a spreading agent, it also may be advantageous to include a dispersant, such as, for example, pyrrolidin-2-one, N-alkylpyrrolidin-2-one, acetone, polyethylene glycol or ether or ester thereof, propylene glycol, or synthetic triglycerides.

When formulated in, for example, an ointment, it is contemplated that the compounds may be mixed with, for example, either a paraffinic or a water-miscible ointment base. When formulated in a cream, it is contemplated that the compounds may be formulated with, for example, an oil-in-water cream base. In some instances, the aqueous phase of the cream base includes, for example at least about 30% (w/w) of a polyhydric alcohol, such as propylene glycol, butane-1,3-diol, mannitol, sorbitol, glycerol, polyethylene glycol, or a mixture thereof.

Injectable formulations may be prepared according to, for example, the known art using suitable solvents, solubilizing agents, protecting agents, dispersing agents, wetting agents, and/or suspending agents. Contemplated carrier materials include, for example, water, ethanol, butanol, benzyl alcohol, glycerin, 1,3-butanediol, Ringer's solution, isotonic sodium chloride solution, bland fixed oils (e.g., synthetic mono- or diglycerides), vegetable oil (e.g., corn oil), dextrose, mannitol, fatty acids (e.g., oleic acid), dimethyl acetamide, surfactants (e.g., ionic and non-ionic detergents), N-methylpyrrolidone, propylene glycol, and/or polyethylene glycols (e.g., PEG 400). Contemplated solubilizing agents include, for example, polyvinyl pyrrolidone, polyoxyethylated castor oil, polyoxyethylated sorbitan ester, and the like. Contemplated protecting agents include, for example, benzyl alcohol, trichlorobutanol, p-hydroxybenzoic acid ester, n-butanol, and the like.

In some embodiments, a parenteral formulation is, for example, prepared from sterile powders or granules having one or more of the carriers materials discussed above for other formulations. The compounds is, for example, dissolved or suspended in a liquid comprising water, polyethylene glycol, propylene glycol, ethanol, corn oil, cottonseed oil, peanut oil, sesame oil, benzyl alcohol, sodium chloride, and/or various buffers. The pH generally may be adjusted, if necessary, with a suitable acid, base, or buffer.

Other inert ingredients may generally be added to the composition as desired. To illustrate, it is contemplated that these may include, for example, lactose, mannitol, sorbitol, calcium carbonate, sodium carbonate, tribasic calcium phosphate, dibasic calcium phosphate, sodium phosphate, kaolin, compressible sugar, starch, calcium sulfate, dextro or microcrystalline cellulose, colloidal silicon dioxide, starch, sodium starch glycolate, crospovidone, microcrystalline cellulose, tragacanth, hydroxypropylcellulose, pregelatinized starch, povidone, ethylcellulose, hydroxypropylcellulose, hydroxypropylmethylcellulose, and methylcellulose.

Further aspects regarding formulation of drugs and various excipients are found in, for example, Gennaro, A. R., et al., eds., *Remington: The Science and Practice of Pharmacy* (Lippincott Williams & Wilkins, 20th Ed., 2000). Another source regarding formulation of drugs and various excipients is found in, for example, Liberman, H. A., et al., eds., *Pharmaceutical Dosage Forms* (Marcel Decker, New York, N.Y., 1980).

The concentration of the compounds according to this invention in the applied dosage form may vary widely depending on, for example, the dosage route. In general, the concentration is from about 1 to about 70% (by weight). In some such embodiments, for example, the concentration is from about 1 to about 50% (by weight), or from about 10 to about 50% (by weight). In other embodiments, the concentration is from about 35 to about 65% (by weight), from about 40 to about 60% (by weight), from about 45 to about 55% (by weight), or about 50% (by weight).

In another aspect the present invention thus provides a pharmaceutical composition comprising an anthelmintically effective amount of one or more, preferably one compound according to this invention and one or more pharmaceutically acceptable excipients.

The formulation type chosen for a dosage form in any instance will depend upon the particular purpose envisaged and the physical, chemical and biological properties of the compound according to this invention.

The compounds and pharmaceutical compositions according to this invention are useful in treating parasitic infections such as helminth infections of animals. An "effective amount," is the amount or quantity of a compound that is required to alleviate or reduce parasite numbers in an animal, and/or to inhibit the development of parasite infections in an animal, in whole or in part.

This amount is readily determined by observation or detection of the pathogen numbers such as parasite numbers both before and after contacting the sample of pathogens such as parasites including their stages with the compound according to this invention, directly and/or indirectly, e.g., by contacting articles, surfaces, foliage, or animals with the compound.

This can be evaluated by counting parasites (especially helminthes) directly after necroscopy of the host animal.

The reduction of parasite numbers, especially gastrointestinal helminth parasites can be alternatively measured indirectly by faecal egg or differential larval counts. In this case the effective amount of the compound is determined by the reduction of the number of excreted helminth eggs or larvae in the faeces of the treated animal before and after treatment. For an in vivo administration the compound according to this invention, is preferably administered to an animal in an effective amount which is synonymous with "pharmaceutically effective amount" or "anthelmintically effective amount".

A single administration of a compound according to this invention is typically sufficient to treat a parasitic infection such as a helminth infection, preferably a nematode, cestode or trematode infection, more preferably a nematode infection. Although such a single dose is typically preferred, it is contemplated that multiple doses can be used. When the compound according to this invention is orally administered, the total dose to treat a disease such as a helminth infection is generally greater than about 0.01 mg/kg (i.e., milligram of compound according to this invention per kilogram body weight of the treated animal). In some such embodiments, the total dose is from about 0.01 to about 100 mg/kg, from about 0.01 to about 50 mg/kg, from about 0.1 to about 25 mg/kg, or from about 1 to about 20. For sheep, for example, the dose is generally from about 0.5 to about 15 mg/kg, from about 1 to about 10 mg/kg. The same dose range may be suitable for other dosage routes. For example, in some embodiments, the same dose range is used for subcutaneous administration. The desired dose, however, may be less in some instances where the compound according to this invention is administered intravenously.

If the compound according to this invention is administered parenterally via an injection, the concentration of the compound according to this invention in the dosage form preferably is sufficient to provide the desired therapeutically effective amount of the compound according to this invention in a volume that is acceptable for parenteral administration.

Factors affecting the preferred dosage may include, for example, the parasite species infection to be treated and the development stages of the parasites, the type (e.g., species and breed), age, size, sex, diet, activity, and condition of the of the infected animal; the dosage route; pharmacological considerations, such as the activity, efficacy, pharmacokinetic, and toxicology profiles of the particular composition administered; and whether the compound according to this invention being administered as part of a combination of active ingredients. Thus, the preferred amount of the compound according to this invention can vary, and, therefore, can deviate from the typical dosages set forth above. Determining such dosage adjustments is generally within the skill of those in the art.

Examples of Contemplated Combination Therapies

The methods and pharmaceutical compositions of this invention encompass methods wherein a compound according to this invention is the sole active ingredient administered to the recipient animal. It is contemplated, however, that the methods and pharmaceutical compositions also encompass combination therapies wherein a compound is administered in combination with one or more other pharmaceutically acceptable active ingredients. The other active ingredient(s) may be, for example, one or more other compounds according to this invention. Alternatively (or additionally), the other active ingredient(s) may be one or more pharmaceutically acceptable compounds that are not compounds according to this invention. The other active ingredient(s) may target the same and/or different parasites and conditions.

Contemplated active ingredient(s) that may be administered in combination with the compounds include, for example, pharmaceutically acceptable anthelmintics, insecticides and acaricides, insect growth regulators, anti-inflammatories, anti-infectives, hormones, dermatological preparations (e.g., antiseptics and disinfectants), and immunobiologicals (e.g., vaccines and antisera) for disease prevention.

Therefore this invention is also directed to the use as a medicament of combinations comprising a) one or more compounds according to this invention with b) one or more pharmaceutically acceptable active compounds which differ in structure from component a). The active compounds b) are preferably anthelmintic compounds, more preferably selected from the group consisting of avermectins (e.g., ivermectin, selamectin, doramectin, abamectin, and eprinomectin); milbemycins (moxidectin and milbemycin oxime); pro-benzimidazoles (e.g., febantel, netobimin, and thiophanate); benzimidazole derivatives, such as a thiazole benzimidazole derivative (e.g., thiabendazole and cambendazole) or a carbamate benzimidazole derivatives (e.g., fenbendazole, albendazole (oxide), mebendazole, oxfendazole, parbendazole, oxibendazole, flubendazole, and triclabendazole); an imidazothiazoles (e.g., levamisole and tetramisole); a tetrahydropyrimidine (morantel and pyrantel), organophosphates (e.g., trichlorphon, haloxon, dichlorvos, and naphthalophos); salicylanilides (e.g., closantel, oxyclozanide, rafoxanide, and niclosamide); nitrophenolic compounds (e.g., nitroxynil and nitroscanate); benzenedisulphonamides (e.g., clorsulon); pyrazineisoquinolines (e.g., praziquantel and epsiprantel); heterocyclic compounds (e.g., piperazine, diethylcarbamazine, dichlorophen, and phenothiazine); arsenicals (e.g., thiacetarsamide, melorsamine, and arsenamide); cyclooctadepsipeptides (e.g., emodepside); paraherquamides (e.g. derquantel); and amino-acetonitrile compounds (e.g. monepantel, AAD 1566); tribendimidine (amidine compound); amidine compounds (e.g., amidantel and tribendimidin), including all pharmaceutically acceptable forms, such as salts, solvates or N-oxides.

Preferred combinations are comprising a) one compound selected from the group of compounds A-1 to A-435, B-1 to B-16, C-1, C-291 and D1-D4 of the Tables A, B, C and D below (or salts, solvates or N-oxides thereof if applicable) and b) one compound selected from the group consisting of anthelmintic avermectins (e.g., ivermectin, selamectin, doramectin, abamectin, emamectin and eprinomectin); milbemycins (moxidectin and milbemycin oxime); pro-benzimidazoles (e.g., febantel, netobimin, and thiophanate); benzimidazole derivatives, such as thiazole benzimidazole derivatives (e.g., thiabendazole and cambendazole), carbamate benzimidazole derivatives (e.g., fenbendazole, albendazole (oxide), mebendazole, oxfendazole, parbendazole, oxibendazole, flubendazole, and triclabendazole); imidazothiazoles (e.g., levamisole and tetramisole); tetrahydropyrimidines (morantel and pyrantel), organophosphates (e.g., trichlorphon, haloxon, dichlorvos, and naphthalophos); salicylanilides (e.g., closantel, oxyclozanide, rafoxanide, and niclosamide); nitrophenolic compounds (e.g., nitroxynil and nitroscanate); benzenedisulphonamides (e.g., clorsulon); pyrazineisoquinolines (e.g., praziquantel and epsiprantel); heterocyclic compounds (e.g., piperazine, diethylcarbamazine, dichlorophen, and phenothiazine); arsenicals (e.g., thiacetarsamide, melorsamine, and arsenamide); cyclooctadepsipeptides (e.g., emodepside); paraherquamides (e.g. derquantel); amino-acetonitrile compounds (e.g. monepantel, AAD 1566); tribendimidine (amidine compound); and amidantel (amidine compound); including all pharmaceutically acceptable forms, such as salts.

Preferred combinations comprise at least one compound selected from the group of compounds A-1 to A-435, B-1 to B-16, C-1 to C-291 and D1-D4 of the Tables A, B, C and D below (or salts, solvates or N-oxides thereof if applicable) and abamectin, ivermectin, emamectin, eprinomectin, doramectin, moxidectin, milbemycin oxime; or.

closantel, oxyclozanide, rafoxanide, niclosamide; or nitroxynil, nitroscanate, clorsulon; or praziquantel, epsiprantel; or emodepside, derquantel, monepantel.

Examples of such combinations are combinations of one of the compounds A-1 to A-435, B-1 to B-16, C-1 to C-291 and D1-D4 of the Tables A, B, C and D below with abamectin.

Other examples are combinations of one of the compounds A-1 to A-435, B-1 to B-16, C-1 to C-291 and D1-D4 of the Tables A, B, C and D below with ivermectin.

Other examples are combinations of one of the compounds A-1 to A-435, B-1 to B-16, C-1 to C-291 and D1-D4 of the Tables A, B, C and D below with emamectin.

Other examples are combinations of one of the compounds A-1 to A-435, B-1 to B-16, C-1 to C-291 and D1-D4 of the Tables A, B, C and D below with eprinomectin.

Other examples are combinations of one of the compounds A-1 to A-435, B-1 to B-16, C-1 to C-291 and D1-D4 of the Tables A, B, C and D below with doramectin.

Other examples are combinations of one of the compounds A-1 to A-435, B-1 to B-16, C-1 to C-291 and D1-D4 of the Tables A, B, C and D below with moxidectin.

Other examples are combinations of one of the compounds A-1 to A-435, B-1 to B-16, C-1 to C-291 and D1-D4 of the Tables A, B, C and D below with milbemycin oxime.

Other examples are combinations of one of the compounds A-1 to A-435, B-1 to B-16, C-1 to C-291 and D1-D4 of the Tables A, B, C and D below with closantel.

Other examples are combinations of one of the compounds A-1 to A-435, B-1 to B-16, C-1 to C-291 and D1-D4 of the Tables A, B, C and D below with oxyclozanide.

Other examples are combinations of one of the compounds A-1 to A-435, B-1 to B-16, C-1 to C-291 and D1-D4 of the Tables A, B, C and D below with rafoxanide.

Other examples are combinations of one of the compounds A-1 to A-435, B-1 to B-16, C-1 to C-291 and D1-D4 of the Tables A, B, C and D below with niclosamide.

Other examples are combinations of one of the compounds A-1 to A-435, B-1 to B-16, C-1 to C-291 and D1-D4 of the Tables A, B, C and D below with nitroxynil.

Other examples are combinations of one of the compounds A-1 to A-435, B-1 to B-16, C-1 to C-291 and D1-D4 of the Tables A, B, C and D below with nitroscanate.

Other examples are combinations of one of the compounds A-1 to A-435, B-1 to B-16, C-1 to C-291 and D1-D4 of the Tables A, B, C and D below with clorsulon.

Other examples are combinations of one of the compounds A-1 to A-435, B-1 to B-16, C-1 to C-291 and D1-D4 of the Tables A, B, C and D below with praziquantel.

Other examples are combinations of one of the compounds A-1 to A-435, B-1 to B-16, C-1 to C-291 and D1-D4 of the Tables A, B, C and D below with epsiprantel.

Other examples are combinations of one of the compounds A-1 to A-435, B-1 to B-16, C-1 to C-291 and D1-D4 of the Tables A, B, C and D below with emodepside.

Other examples are combinations of one of the compounds A-1 to A-435, B-1 to B-16, C-1 to C-291 and D1-D4 of the Tables A, B, C and D below with derquantel.

Other examples are combinations of one of the compounds A-1 to A-435, B-1 to B-16, C-1 to C-291 and D1-D4 of the Tables A, B, C and D below with monepantel.

Examples of such combinations are combinations of a salt of one of the compounds A-1 to A-435, B-1 to B-16, C-1 to C-291 and D1-D4 of the Tables A, B, C and D below with abamectin.

Other examples are combinations of a salt of one of the compounds A-1 to A-435, B-1 to B-16, C-1 to C-291 and D1-D4 of the Tables A, B, C and D below with ivermectin.

Other examples are combinations of a salt of one of the compounds A-1 to A-435, B-1 to B-16, C-1 to C-291 and D1-D4 of the Tables A, B, C and D below with emamectin.

Other examples are combinations of a salt of one of the compounds A-1 to A-435, B-1 to B-16, C-1 to C-291 and D1-D4 of the Tables A, B, C and D below with eprinomectin.

Other examples are combinations of a salt of one of the compounds A-1 to A-435, B-1 to B-16, C-1 to C-291 and D1-D4 of the Tables A, B, C and D below with doramectin.

Other examples are combinations of a salt of one of the compounds A-1 to A-435, B-1 to B-16, C-1 to C-291 and D1-D4 of the Tables A, B, C and D below with moxidectin.

Other examples are combinations of a salt of one of the compounds A-1 to A-435, B-1 to B-16, C-1 to C-291 and D1-D4 of the Tables A, B, C and D below with milbemycin oxime.

Other examples are combinations of a salt of one of the compounds A-1 to A-435, B-1 to B-16, C-1 to C-291 and D1-D4 of the Tables A, B, C and D below with closantel.

Other examples are combinations of a salt of one of the compounds A-1 to A-435, B-1 to B-16, C-1 to C-291 and D1-D4 of the Tables A, B, C and D below with oxyclozanide.

Other examples are combinations of a salt of one of the compounds A-1 to A-435, B-1 to B-16, C-1 to C-291 and D1-D4 of the Tables A, B, C and D below with rafoxanide.

Other examples are combinations of a salt of one of the compounds A-1 to A-435, B-1 to B-16, C-1 to C-291 and D1-D4 of the Tables A, B, C and D below with niclosamide.

Other examples are combinations of a salt of one of the compounds A-1 to A-435, B-1 to B-16, C-1 to C-291 and D1-D4 of the Tables A, B, C and D below with nitroxynil.

Other examples are combinations of a salt of one of the compounds A-1 to A-435, B-1 to B-16, C-1 to C-291 and D1-D4 of the Tables A, B, C and D below with nitroscanate.

Other examples are combinations of a salt of one of the compounds A-1 to A-435, B-1 to B-16, C-1 to C-291 and D1-D4 of the Tables A, B, C and D below with clorsulon.

Other examples are combinations of a salt of one of the compounds A-1 to A-435, B-1 to B-16, C-1 to C-291 and D1-D4 of the Tables A, B, C and D below with praziquantel.

Other examples are combinations of a salt of one of the compounds A-1 to A-435, B-1 to B-16, C-1 to C-291 and D1-D4 of the Tables A, B, C and D below with epsiprantel.

Other examples are combinations of a salt of one of the compounds A-1 to A-435, B-1 to B-16, C-1 to C-291 and D1-D4 of the Tables A, B, C and D below with emodepside.

Other examples are combinations of a salt of one of the compounds A-1 to A-435, B-1 to B-16, C-1 to C-291 and D1-D4 of the Tables A, B, C and D below with derquantel.

Other examples are combinations of a salt of one of the compounds A-1 to A-435, B-1 to B-16, C-1 to C-291 and D1-D4 of the Tables A, B, C and D below with monepantel.

Examples of such combinations are combinations of a solvate of one of the compounds A-1 to A-435, B-1 to B-16, C-1 to C-291 and D1-D4 of the Tables A, B, C and D below with abamectin.

Other examples are combinations of a solvate of one of the compounds A-1 to A-435, B-1 to B-16, C-1 to C-291 and D1-D4 of the Tables A, B, C and D below with ivermectin.

Other examples are combinations of a solvate of one of the compounds A-1 to A-435, B-1 to B-16, C-1 to C-291 and D1-D4 of the Tables A, B, C and D below with emamectin.

Other examples are combinations of a solvate of one of the compounds A-1 to A-435, B-1 to B-16, C-1 to C-291 and D1-D4 of the Tables A, B, C and D below with eprinomectin.

Other examples are combinations of a solvate of one of the compounds A-1 to A-435, B-1 to B-16, C-1 to C-291 and D1-D4 of the Tables A, B, C and D below with doramectin.

Other examples are combinations of a solvate of one of the compounds A-1 to A-435, B-1 to B-16, C-1 to C-291 and D1-D4 of the Tables A, B, C and D below with moxidectin.

Other examples are combinations of a solvate of one of the compounds A-1 to A-435, B-1 to B-16, C-1 to C-291 and D1-D4 of the Tables A, B, C and D below with milbemycin oxime.

Other examples are combinations of a solvate of one of the compounds A-1 to A-435, B-1 to B-16, C-1 to C-291 and D1-D4 of the Tables A, B, C and D below with closantel.

Other examples are combinations of a solvate of one of the compounds A-1 to A-435, B-1 to B-16, C-1 to C-291 and D1-D4 of the Tables A, B, C and D below with oxyclozanide.

Other examples are combinations of a solvate of one of the compounds A-1 to A-435, B-1 to B-16, C-1 to C-291 and D1-D4 of the Tables A, B, C and D below with rafoxanide.

Other examples are combinations of a solvate of one of the compounds A-1 to A-435, B-1 to B-16, C-1 to C-291 and D1-D4 of the Tables A, B, C and D below with niclosamide.

Other examples are combinations of a solvate of one of the compounds A-1 to A-435, B-1 to B-16, C-1 to C-291 and D1-D4 of the Tables A, B, C and D below with nitroxynil.

Other examples are combinations of a solvate of one of the compounds A-1 to A-435, B-1 to B-16, C-1 to C-291 and D1-D4 of the Tables A, B, C and D below with nitroscanate.

Other examples are combinations of a solvate of one of the compounds A-1 to A-435, B-1 to B-16, C-1 to C-291 and D1-D4 of the Tables A, B, C and D below with clorsulon.

Other examples are combinations of a solvate of one of the compounds A-1 to A-435, B-1 to B-16, C-1 to C-291 and D1-D4 of the Tables A, B, C and D below with praziquantel.

Other examples are combinations of a solvate of one of the compounds A-1 to A-435, B-1 to B-16, C-1 to C-291 and D1-D4 of the Tables A, B, C and D below with epsiprantel.

Other examples are combinations of a solvate of one of the compounds A-1 to A-435, B-1 to B-16, C-1 to C-291 and D1-D4 of the Tables A, B, C and D below with emodepside.

Other examples are combinations of a solvate of one of the compounds A-1 to A-435, B-1 to B-16, C-1 to C-291 and D1-D4 of the Tables A, B, C and D below with derquantel.

Other examples are combinations of a solvate of one of the compounds A-1 to A-435, B-1 to B-16, C-1 to C-291 and D1-D4 of the Tables A, B, C and D below with monepantel.

Examples of such combinations are combinations of an N-oxide of one of the compounds A-1 to A-435, B-1 to B-16 and C-1 to C-291 of the Tables A, B, and C below with abamectin.

Other examples are combinations of an N-oxide of one of the compounds A-1 to A-435, B-1 to B-16 and C-1 to C-291 of the Tables A, B, and C below with ivermectin.

Other examples are combinations of an N-oxide of one of the compounds A-1 to A-435, B-1 to B-16 and C-1 to C-291 of the Tables A, B, and C below with emamectin.

Other examples are combinations of an N-oxide of one of the compounds A-1 to A-435, B-1 to B-16 and C-1 to C-291 of the Tables A, B, and C below with eprinomectin.

Other examples are combinations of an N-oxide of one of the compounds A-1 to A-435, B-1 to B-16 and C-1 to C-291 of the Tables A, B, and C below with doramectin.

Other examples are combinations of an N-oxide of one of the compounds A-1 to A-435, B-1 to B-16 and C-1 to C-291 of the Tables A, B, and C below with moxidectin.

Other examples are combinations of an N-oxide of one of the compounds A-1 to A-435, B-1 to B-16 and C-1 to C-291 of the Tables A, B, and C below with milbemycin oxime.

Other examples are combinations of an N-oxide of one of the compounds A-1 to A-435, B-1 to B-16 and C-1 to C-291 of the Tables A, B, and C below with closantel.

Other examples are combinations of an N-oxide of one of the compounds A-1 to A-435, B-1 to B-16 and C-1 to C-291 of the Tables A, B, and C below with oxyclozanide.

Other examples are combinations of an N-oxide of one of the compounds A-1 to A-435, B-1 to B-16 and C-1 to C-291 of the Tables A, B, and C below with rafoxanide.

Other examples are combinations of an N-oxide of one of the compounds A-1 to A-435, B-1 to B-16 and C-1 to C-291 of the Tables A, B, and C below with niclosamide.

Other examples are combinations of an N-oxide of one of the compounds A-1 to A-435, B-1 to B-16 and C-1 to C-291 of the Tables A, B, and C below with nitroxynil.

Other examples are combinations of an N-oxide of one of the compounds A-1 to A-435, B-1 to B-16 and C-1 to C-291 of the Tables A, B, and C below with nitroscanate.

Other examples are combinations of an N-oxide of one of the compounds A-1 to A-435, B-1 to B-16 and C-1 to C-291 of the Tables A, B, and C below with clorsulon.

Other examples are combinations of an N-oxide of one of the compounds A-1 to A-435, B-1 to B-16 and C-1 to C-291 of the Tables A, B, and C below with praziquantel.

Other examples are combinations of an N-oxide of one of the compounds A-1 to A-435, B-1 to B-16 and C-1 to C-291 of the Tables A, B, and C below with epsiprantel.

Other examples are combinations of an N-oxide of one of the compounds A-1 to A-435, B-1 to B-16 and C-1 to C-291 of the Tables A, B, and C below with emodepside.

Other examples are combinations of an N-oxide of one of the compounds A-1 to A-435, B-1 to B-16 and C-1 to C-291 of the Tables A, B, and C below with derquantel.

Other examples are combinations of an N-oxide of one of the compounds A-1 to A-435, B-1 to B-16 and C-1 to C-291 of the Tables A, B, and C below with monepantel.

The compounds of the current invention can be combined with pharmaceutically acceptable insecticides or acaricides. Such pharmaceutically acceptable insecticides and acaricides include, for example, acetamiprid, acetoprole, amitraz, amidoflumet, avermectin, azadirachtin, bifenthrin, bifenazate, buprofezin, bistrifluron, chlorfenapyr, chlorfluazuron, chlorantraniliprole, chlorpyrifos, chromafenozide, clothianidin, cyantraniliprole, cyflumetofen, β-cyfluthrin, cyhalothrin, λ-cyhalothrin, cymiazole cypermethrin, cyromazine, deltamethrin, demiditraz, diafenthiuron, diazinon, diflubenzuron, dimefluthrin, dinotefuran, emamectin, esfenvalerate, ethiprole, fenoxycarb, fenpropathrin, fenvalerate, fipronil, flonicamid, flubendiamide, flucythrinate, tau-fluvalinate, flufenoxuron, halofenozide, hexaflumuron, imidacloprid, indoxacarb, lufenuron, metaflumizone, methoprene, metofluthrin, methoxyfenozide, nitenpyram, novaluron, noviflumuron, permethrin, phosmet, profluthrin, protrifenbute, pymetrozine, pyrafluprole, pyrethrin, pyridalyl, pyrifluquinazon, pyriprole, pyriproxyfen, rotenone, ryanodine, spinetoram, spinosad, spirodiclofen, spiromesifen, spirotetramat, sulfoxaflor, tebufenozide, tebufenpyrad, teflubenzuron, tefluthrin, tetrachlorvinphos, tetramethylfluthrin, thiacloprid, thiamethoxam, tolfenpyrad, tralomethrin, and triflumuron. General references discussing antiparasitic agents, such as insecticides and acaricides, include, for example, *The Pesticide Manual,* 13th Edition, C. D. S. Tomlin, Ed., British Crop Protection Council, Farnham, Surrey, U.K. (2003).

In some contemplated embodiments, the compounds are administered with pyridylmethylamine derivatives, such as, for example, pyridylmethylamine derivatives discussed in European Patent Appl. EP0539588 or Intl Patent Appl. Publ. WO2007/115643.

In some contemplated embodiments, the compounds is administered with nodulisporic acids and derivatives thereof, such as, for example, compounds discussed in U.S. Pat. Nos. 5,399,582; 5,945,317; 5,962,499; 5,834,260; 6,221,894; or 5,595,991; or Intl Patent Appl. Publ. 1996/29073.

Pharmaceutically acceptable insect growth regulators include, for example, methoprene, pyriproxyfen, tetrahydroazadirachtin, chlorfluazuron, cyromazine, diflubenzuron, fluazuron, flucycloxuron, flufenoxuron, hexaflumuron, lufenuron, ifenuron, tebufenozide, and triflumuron. These compounds tend to provide both initial and sustained treatment of parasite infections at all stages of insect development, including eggs, on the animal subject, as well as within the environment of the animal subject.

Other antiparasitic compounds contemplated to be useful in combination therapies with the compounds include, for example, imidazo[1,2-b]pyridazine compounds discussed in US Patent Appl. Publ. No. 2005-0182059; 1-(4-Mono and di-halomethylsulphonylphenyl)-2-acylamino-3-fluoropropanol compounds discussed U.S. Pat. No. 7,361,689; trifluoromethanesulfonanilide oxime ether compounds discussed in U.S. Pat. No. 7,312,248; n-[(phenyloxy)phenyl]-1,1,1-trifluoromethanesulfonamide and n-[(phenylsulfanyl)phenyl]-1,1,1-trifluoromethanesulfonamide compounds discussed in US Patent Appl. Publ. 2006-0281695; and 2-phenyl-3-(1H-pyrrol-2-yl)acrylonitrile compounds discussed in US Appl. Publ. 2006/0128779; isoxazoline compounds discussed in WO Patent Appl, Publ. 2005-085216, WO 2007-026965, WO 2007-070606, WO 2007-075459, WO 2007-079162, WO 2007-105814, WO 2007-125984, WO 2008-019760, WO 2008-122375, WO 2008-150393, WO 2009-002809, WO 2009-003075, WO 2009-022746, WO 2009-035004, WO 2009-045999, WO 2009-051956, WO 2009-035004.

In the contemplated combination therapies, the compounds according to this invention may be administered before, simultaneously, and/or after the other active ingredient(s). In addition, the compounds according to this invention may be administered in the same composition as the other active ingredient(s) and/or in separate compositions from the other active ingredient(s). Further, the compounds according to this invention and other active ingredient(s) may be administered via the same and/or different dosage route.

When the compounds according to this invention are administered in a combination therapy, the weight ratio of the active ingredients may vary widely. Factors influencing this ratio include, for example, the particular compounds; the identity of the other active ingredient(s) be administered in the combination therapy; the dosage route of the compounds and other active ingredient(s); the target condition and pathogen; the type (e.g., species and breed), age, size, sex, diet, activity, and condition of the animal; and pharmacological considerations, such as the activity, efficacy, pharmacokinetic, and toxicology profiles of the compounds and other active ingredient(s). In some contemplated embodiments, for example, the weight ratio of the compounds to the other active ingredient(s) is, for example, is from about 1:3000 to about 3000:1. In some such instances, the weight ratio is from about 1:300 to about 300:1. In other such instances, the weight ratio is from about 1:30 and about 30:1.

In addition to other active ingredients, it is contemplated that the compounds may be administered with one or more other compounds that beneficially affects (e.g. enhances or prolongs) the activity (or other characteristic, such as safety) of the compounds. For example, it is contemplated that the compounds may be administered with one or more synergists, such as, for example, piperonyl butoxide (PBO) and triphenyl phosphate (TPP). Other synergists include, for example, N-(2-ethylhexyl)-8,9,10-trinorborn-5-ene-2,3-dicarboxamide (also known as "ENT 8184" or "MGK 264") and Verbutin (also known as "MB-599").

This invention also is directed to kits that are, for example, suitable for use in performing the methods of treatment described above. The kit comprises a therapeutically effective amount of one or more compounds of this invention, and an additional component. The additional component(s) may be, for example, one or more of the following: another ingredient (e.g., an excipient or active ingredient), an apparatus for combining the compound of this invention with another ingredient and/or for administering the compound of this invention, or a diagnostic tool.

The compounds used according to this invention show an excellent activity in treating parasite infections and in addition are acceptable for the animals treated.

EXAMPLES

The following examples are merely illustrative, and not limiting to the remainder of the disclosure in any way.

A. General Description of Synthesis of Compounds According to this Specification The compounds as described in this specification can be obtained by various synthesis routes. A person skilled in the art will choose the synthetic route to obtain compounds as described in this specification depending on the nature of its radicals as defined in relation to Formula I. This is illustrated in the following schemes, which are merely illustrative but not limiting the disclosure in any way.

Scheme 1:

route 1

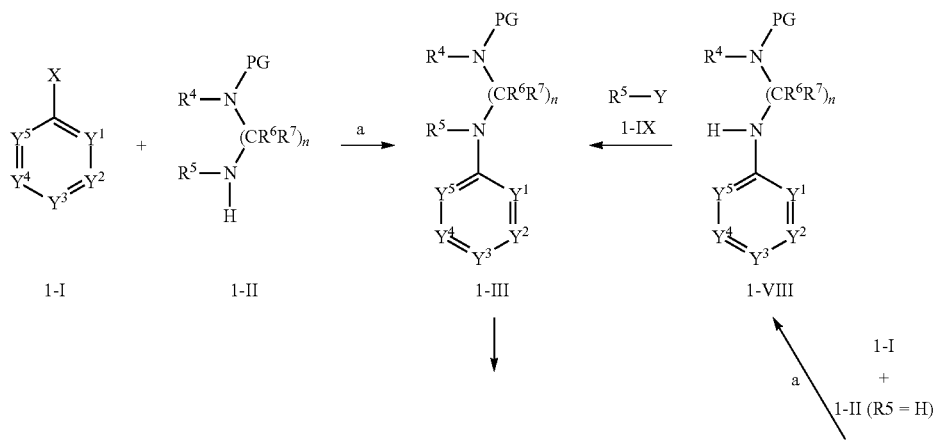

route 2

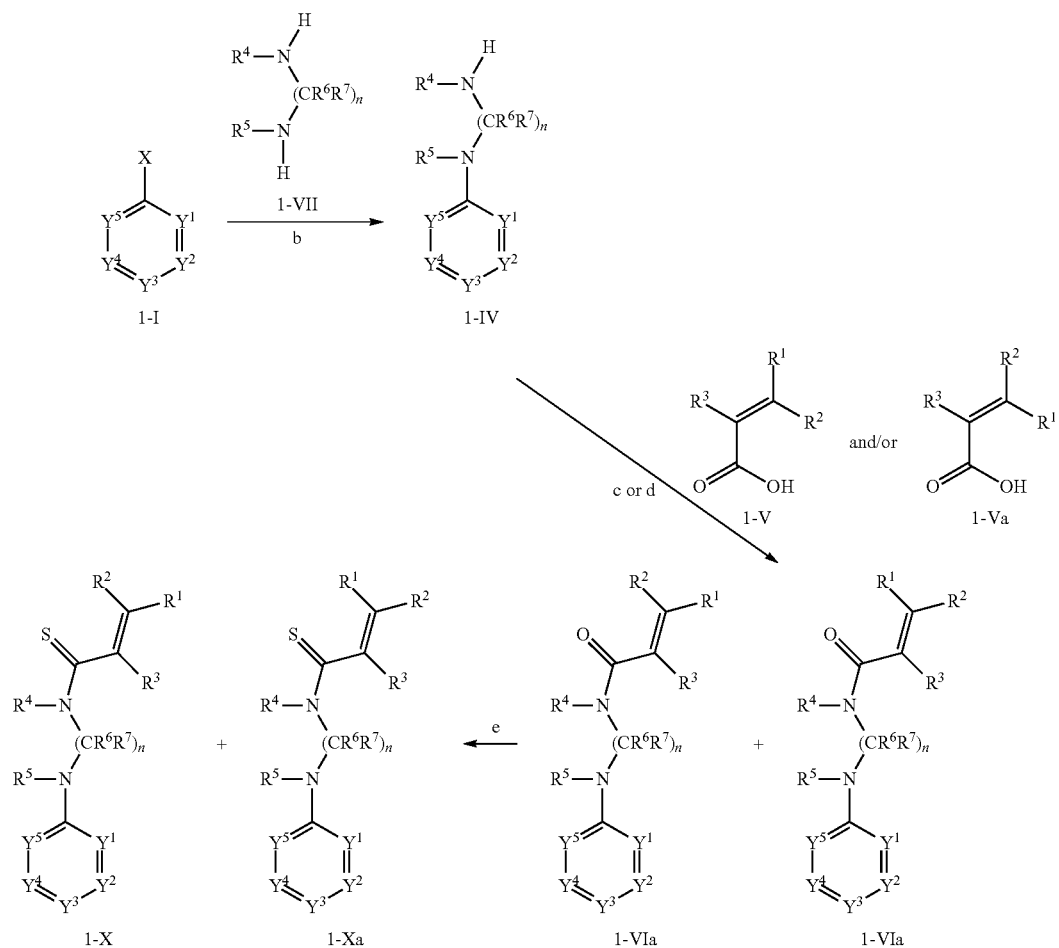

Exemplary conditions: a: palladium acetate, 2,2'-Bis(diphenylphosphino)-1,1'-binaphthyl (BINAP), caesium carbonate, dioxane; b: $K_2CO_3$, 140° C. c: oxalyl chloride, dichloromethane (DCM), dimethylformamide (DMF) then DCM, triethylamine (TEA); d: 2-(1H-Benzotriazole-1-yl)-1,1,3,3-tetramethylaminium hexafluorophosphate (HBTU), diisopropylethylamine, DMF, room temperature; e: Lawesson's reagent, tetrahydrofuran (THF), 130° C.

A compound of general formula 1-VI can be synthesized as shown in scheme 1: in route 2 a heteroarylcompound 1-I is reacted with a diamine 1-VII to give 1-IV. 1-I contains a suitable leaving group X, which is preferably a halogon like chloro or bromo. The reaction is done preferably under Pd-catalysis employing a Pd-containing molecule like palladium acetate or tris(dibenzylideneacetone)dipalladium(0)($Pd_2$(DBA)$_3$), a phosphorus-containing ligand like 2-2'-bis(diphenylphosphino)-1,1'-binaphthyl (BINAP) or 2-(dicyclohexylphosphino)-2',6'-di-isopropoxy-1,1'-biphenyl (RuPhos) or 2-(dicyclohexylphosphino)-3,6-dimethoxy-2',4',6'-tri-isopropyl-1,1'biphenyl (BrettPhos), a base like caesium carbonate or sodium tert-butoxide in a solvent like an ether-containing solvent like diethylether, dioxane or tetrahedrofuran, preferably dioxane or an inert solvent like toluene and preferably at elevated temperatures. 1-VII is employed preferably in excess. Alternativly, the reaction might be done under copper-catalysis using a copper compound like CuI, a base like triethylamine or potassium carbonate and preferably at elevated temperatures. Depending on the nature of 1-I the leaving group X might be displaced by 1-II under conditions for nucleophilic substitutions. For example, if X is a leaving group like halogen or a nitro group and $Y^1$-$Y^5$ are substituted by electron withdrawing substituents, the reaction can be carried out in a solvent like dioxane or, for example, a high boiling solvent like ethyleneglycolmonomethyl ether, optionally with addition of a base like, for example, ethyldiisopropylamine. Or the reaction can be carried out without solvent by using the diamine 1-VII in excess with the optional addition of a base like, for example, potassium carbonate. Also if $Y^1$ and/or $Y^5$ in 1-I is a nitrogen, such a nucleophilic substitution might be performed.

The diamine can be protected with a suitable protecting group as in 1-II of route 1. Suitable protecting groups (PG) for the nitrogen in 1-II include, but are not limited to, preferably tert-butyl carbamate (Boc), benzyl carbamate (Cbz) and the like. A protected diamine 1-II can be reacted under the same conditions as 1-VII, for example by Pd-catalysis employing a Pd-containing molecule like palladium acetate, a phosphorus-containing ligand like BINAP, a base like caesium carbonate or sodium tert-butoxide in a solvent like an ether-containing solvent like diethylether, dioxane or tetrahydrofuran, preferably dioxane or an inert solvent like toluene. The protecting group in the intermediate 1-III can be removed by suitable methods known to a person skilled in the art; if PG is a Boc-group, for example, the protecting group can be removed by an acid like trifluoroacetic acid or hydrochloric acid to give the amine 1-IV. Other suitable methods for protection and deprotection are described in, for example, Green and Wuts, *Protective Groups in Organic Synthesis*, 3$^{rd}$ *edition*, John Wiley & Sons, New York, 1999. It might be advantageous to convert 1-IV when it is obtained by route 2 to the protected derivative 1-III to facilitate purification, for example by chromatography, and remove the protecting group after purification.

If 1-I and 1-II are reacted and R$^5$ is H, the resulting 1-VIII can be reacted with 1-IX to give the intermediate 1-III. 1-IX contains a suitable leaving group Y, e.g. a chloro and is, depending on the nature of the radical R$^5$ an alkylating or acylating agent that is reacted under conditions known to a person skilled in the art. 1-IV is acylated with an unsaturated acid derivative 1-V to give the final product 1-VI. 1-V can be accompanied by the isomeric 1-Va, so that a mixture of 1-V and 1-Va is used in the acylation step. In this case a mixture of 1-VI and 1-VIa is formed that can be separated by methods known to a person skilled in the art, e.g. by chromatography. Or 1-Va can be used in a pure form in the acylation step to give 1-VIa. Thus, if in the following descriptions and schemes the acid 1-V is mentioned, the same applies for the isomeric acid 1-Va, either in its pure form or in form of a mixture of 1-V and 1-Va. The same applies for reaction products derived from 1-V: these can be obtained in pure form if the isomerically pure 1-V or 1-Va are used in the acylation step, or they can be obtained as a mixture if a mixture of 1-V and 1-Va is used and might be separated then by methods known to a person skilled in the art, e.g. by chromatography. There are many acylation methods known to a person skilled in the art: 1-V can be converted to an acid chloride with oxalyl chloride, thionyl chloride or the like which can be isolated or used directly to react with 1-IV in the presence of a base like triethylamine or diisopropylethylamine to give 1-VI. The base might also be polymer-supported to ease work-up. The base might be used in excess, the excess might be removed using aqueous work-up or polymer-supported reagents like polymer-supported acid chloride. The acid 1-V can also be reacted directly with the amine 1-IV using coupling reagents like N,N,N',N'-tetramethyl-O-(7-azabenzotriazol-1-yl)-uronium hexafluorophosphate (HATU), N,N,N',N'-tetramethyl-O-(1H-benzotriazol-1-yl)-uronium hexafluorophosphate (HBTU), 1-hydroxy-7-azabenzotriazole (HOAt), N,N'-dicyclohexylcarbodiimide (DCC) or the like. Other suitable amide coupling procedures are described in Goodman, M.; Felix, A.; Moroder, L.; Toniolo, C. in volume E22a of *Methods of Organic Chemistry (Houben-Weyl), Synthesis of Peptides and Peptidomimetics*, 4$^{th}$ *edition*, Georg Thieme Verlag, Stuttgart—New York, 2002. 1-VI and 1-VIa can be converted into their thiocarbonyl analogue 1-X and 1-Xa by treatment with, for example, Lawesson's reagent under microwave heating. Other methods are described in, for example, Smith, M. B.; March, J.; *March's Advanced Organic Chemistry*, John Wiley & Sons, Hoboken; New Jersey, 2007, 1277-1280. A compound of general formula 1-VI can be substituted at Y$^1$-Y$^5$. This substituent can already be present in the heteroaryl compound 1-I. A person skilled in the art will appreciate that it can also be introduced in a compound 1-III, 1-IV or 1-VI. For example, Y$^1$-Y$^5$ in 1-I might be substituted by a potential leaving group like, for example, halogen, which can be replaced by another group, for example a nucleophilic group in, for example, a nucleophilic substitution reaction. Or, for example, Y$^1$-Y$^5$ in 1-III might be substituted by a potential leaving group like, for example, halogen, which can be replaced by another group, for example a nucleophilic group in, for example, a nucleophilic substitution reaction. Or, for example, Y$^1$-Y$^5$ in 1-IV might be substituted by a potential leaving group like, for example, halogen, which can be replaced by another group, for example a nucleophilic group in, for example, a nucleophilic substitution reaction. 1-I might also be substituted at Y$^1$-Y$^5$ with a group that can react with a group present in the reaction partner 1-II or 1-VII like, for example, the amino group in 1-II or 1-VII. In this case the reacting group in 1-I can be protected by a protecting group by methods known to a person skilled in the art. For example, 1-I can be substituted by an acyl group. This acyl group can be protected as, for example, an oxolan prior to the reaction with 1-II or 1-VII and deprotected by, for example, aqueous acid after the reaction with 1-II or 1-VII as described in, for example, Green and Wuts, *Protective Groups in Organic Synthesis*, 3$^{rd}$ *edition*, John Wiley & Sons, New York, 1999. The same applies to the following schemes in an analogous way.

The heteroaryl compound 1-I can be substituted at the N-Atom with oxygen, thus being a heteroaryl-N-oxid, for example a quinoline-N-oxid or a pyridine-N-oxid. Methods for the synthesis of such heteroaryl-N-oxides are described in, for example, R. Kreher (editor), volume E7a of *Methods of Organic Chemistry (Houben-Weyl), Hetarenes II, part 1*, 4$^{th}$ *edition*, Georg Thieme Verlag, Stuttgart—New York, 1991. A person skilled in the art will appreciate that the synthetic transformations described in scheme 1 result in this case in the corresponding heteroaryl-N-oxides of heteroaryl compounds of general formula 1-VI and 1-VIa, for example. Or, the presence of such an N-oxide might facilitate the formation of 1-IV or 1-III from 1-I. In this case, the N-oxide might be removed by reduction after substitution with 1-II or 1-VII. The same applies for the following schemes.

Scheme 2:

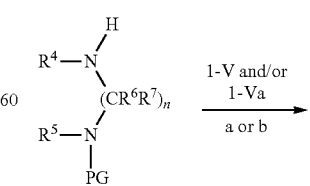

2-I

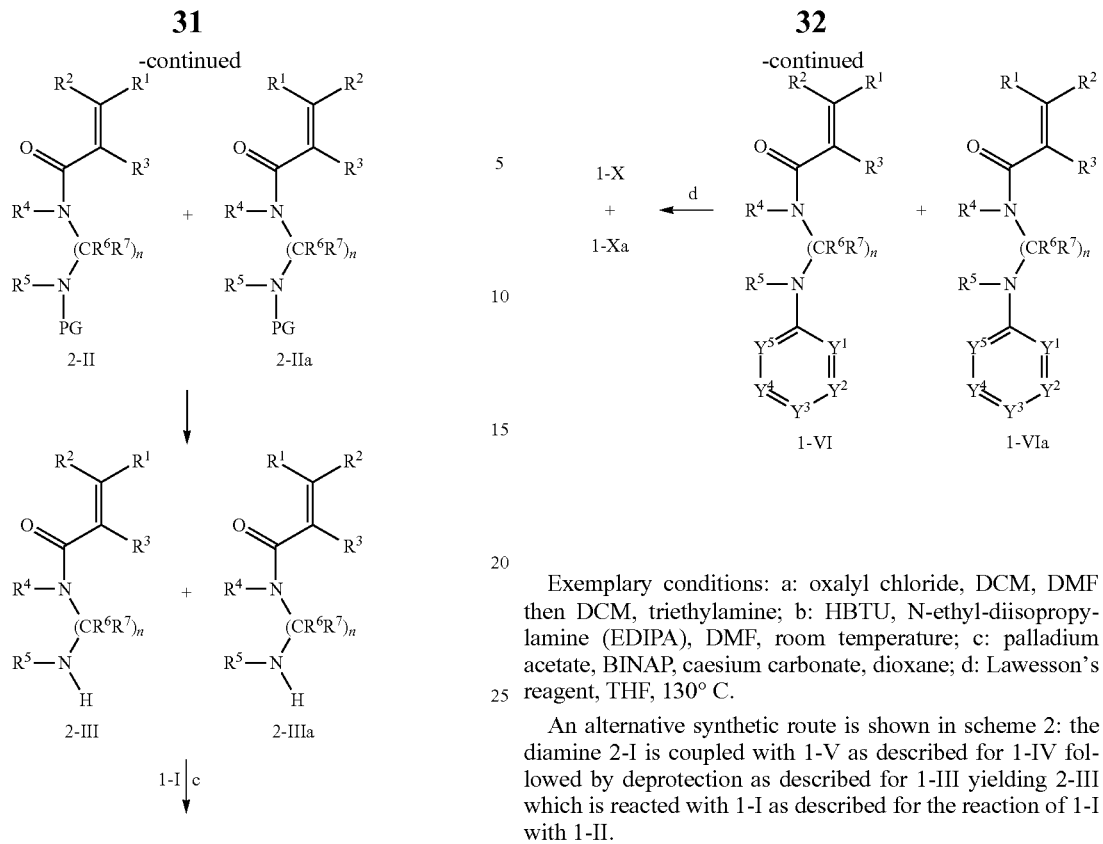

Exemplary conditions: a: oxalyl chloride, DCM, DMF then DCM, triethylamine; b: HBTU, N-ethyl-diisopropylamine (EDIPA), DMF, room temperature; c: palladium acetate, BINAP, caesium carbonate, dioxane; d: Lawesson's reagent, THF, 130° C.

An alternative synthetic route is shown in scheme 2: the diamine 2-I is coupled with 1-V as described for 1-IV followed by deprotection as described for 1-III yielding 2-III which is reacted with 1-I as described for the reaction of 1-I with 1-II.

Scheme 3:

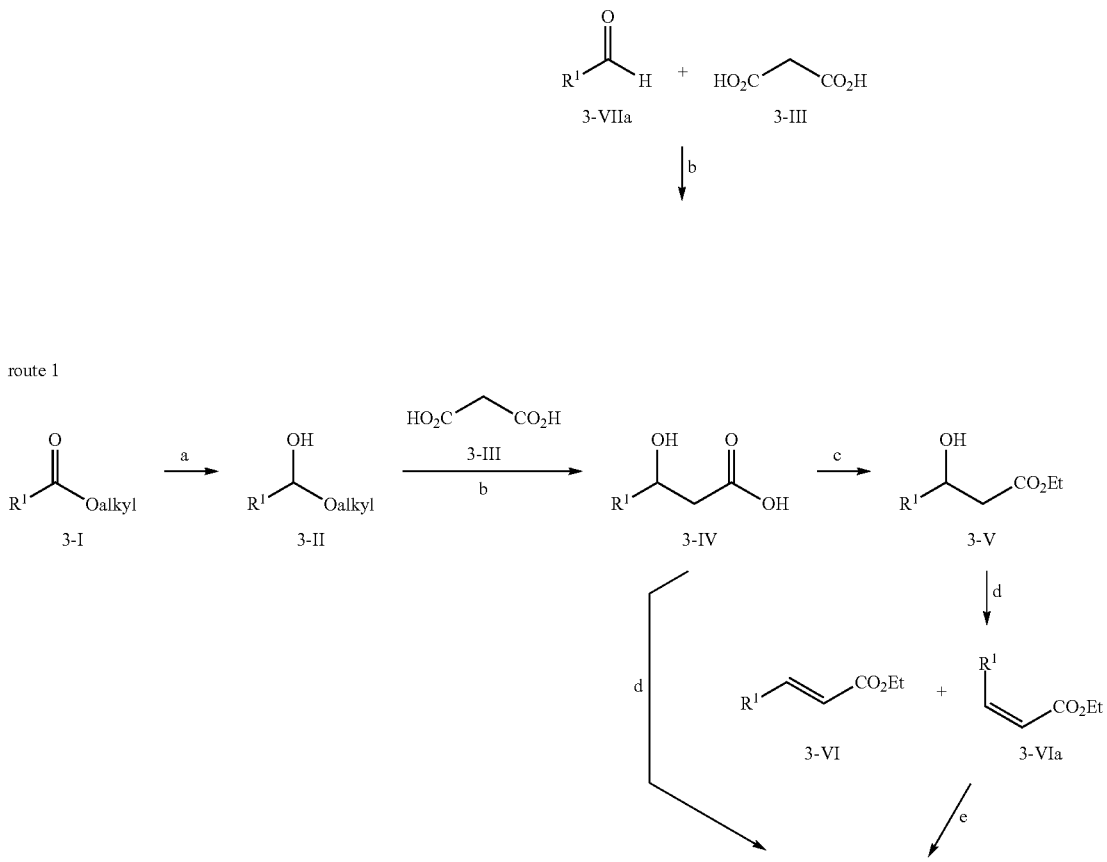

route 2 ($R^3$ = H)

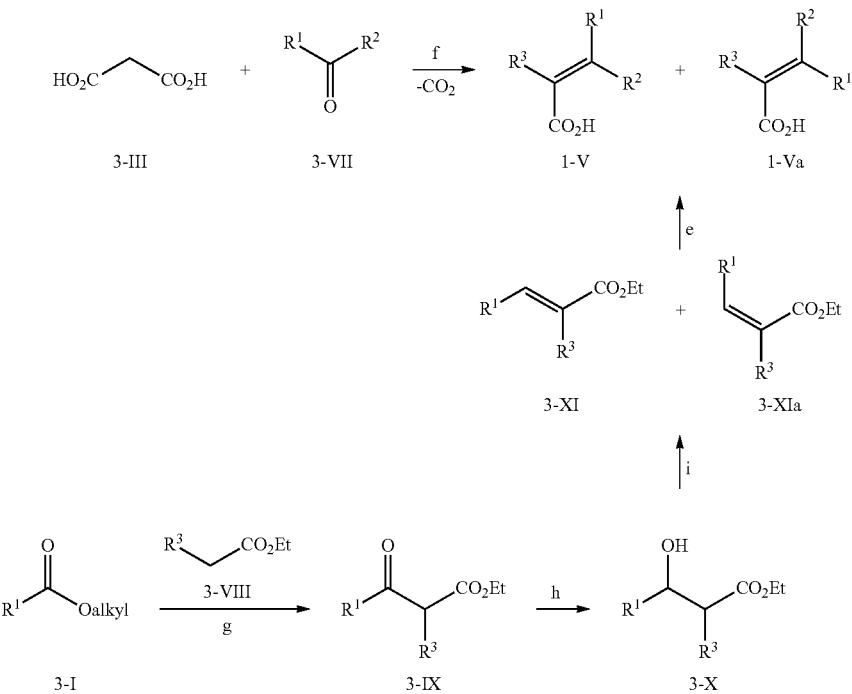

route 3

Exemplary conditions: a: sodium borohydride, methanol; b: pyridine, piperidine; c: ethanol, HCl; d: phosphorus pentoxide; e: NaOH; f: pyridine, piperidine, reflux; g: LiN(Si(CH$_3$)$_3$)$_2$, THF; h: sodium borohydride, toluene; i: phosphorus pentoxide The unsaturated acids used for acylation (1-V in scheme 1) can be synthesized in several ways, many of which are described in: J. Falbe in volume E5, part1 of *Methods of Organic Chemistry (Houben-Weyl), Carboxylic acids,* 4$^{th}$ edition, Georg Thieme Verlag, Stuttgart—New York, 1985. The preferred route will be chosen by a person skilled in the art according to the nature of the radicals $R^1$, $R^2$ and $R^3$. For example, in scheme 3, if $R^2$ is H and $R^1$ is alkyl preferably route 2 will be chosen. If $R^2$ is H and $R^1$ is alkyl substituted by halogen like F and/or Cl, route 1 or 3 will preferably be chosen. According to route 2 in scheme 3 malonic acid 3-III is condensed with an aldehyde or ketone 3-VII to yield directly the crotonic acid 1-V, which can be accompanied by the isomeric 1-Va. Suitable reaction conditions include heating the reactants in a solvent, preferably pyridine with the addition of piperidine. According to route 1, a carboxylic ester 3-I is reduced to the hemiacetal 3-II, which is condensed with malonic acid in a manner analogous to route 1. Alternativly, the aldehyde 3-VIIa can be condensed with malonic acid to give the hydroxyacid 3-IV. The hydroxyacid 3-IV might be isolated or used directly in a dehydration step to yield I-V. Preferably, the hydroxyacid is esterified to 3-V which is dehydrated to 3-VI and hydrolysed to the acid 1-V. Methods for the dehydration of 3-IV and 3-V are described in, for example, M. Jagodzinska et al.; *Tetrahedron* 63 (2007), 2042-2046; P. F. Bevilaqua, *J. Org. Chem.* 94 (1984), 1430-1434 and include treatment of a hydroxyacid or —ester like 3-IV or 3-V with P$_2$O$_5$ at preferably elevated temperatures or treatment with diethylazodicarboxylate and tri phenylphosphine.

According to route 3 an ester 3-I is condensed with a CH-acidic ester 3-VIII to give a beta-keto ester 3-IX which is reduced to the hydroxyester 3-X. Methods for the condensation of an ester with another CH-acidic ester are known to a person skilled in the art, as well as methods for the reduction of a keto group to a hydroxygroup and are described in, for example, M. Jagodzinska et al.; *Tetrahedron* 63 (2007), 2042-2046; T. Kitazume; *J. Fluorine Chemistry* 42 (1989), 17-29. 3-X is then converted to the crotonic acid 1-V in a manner analogous to the one described above for 5-V.

In all of the described routes, 1-V might be accompanied by the isomeric 1-Va. Depending on the nature of the radicals $R^1$ and $R^2$ the isomers 1-V and 1-Va can be formed in varying proportions. For example if $R^2$ is H, the E-isomer 1-V is predominantly formed. The isomeric 1-V and 1-Va can be separated by methods known to a person skilled in the art, e.g. by chromatography and can be used as pure isomers in subsequent reactions. Or 1-V and 1-Va can be used as a mixture in subsequent reactions and the resulting isomeric products can be separated in a later step. Unsaturated acids with $R^1$=SF$_5$ and $R^2$=H and $R^3$=H can also be obtained as described in, for example, V. K. Brel, *Synthesis* 2006, 339-343. Unsaturated acids with $R^1$=alkylthio and alkylsulfonyl and $R^2$=H and $R^3$=H can also be obtained as described in, for example, J. T. Moon, *Bioorg. Med. Chem. Letters* 20 (2010) 52-55. Many unsaturated acids 1-V used as starting materials are also commercially available by a large number of vendors as listed in, for example, the Symyx Available Chemicals Directory (ACD) or SciFinder (ACS).

Scheme 4:
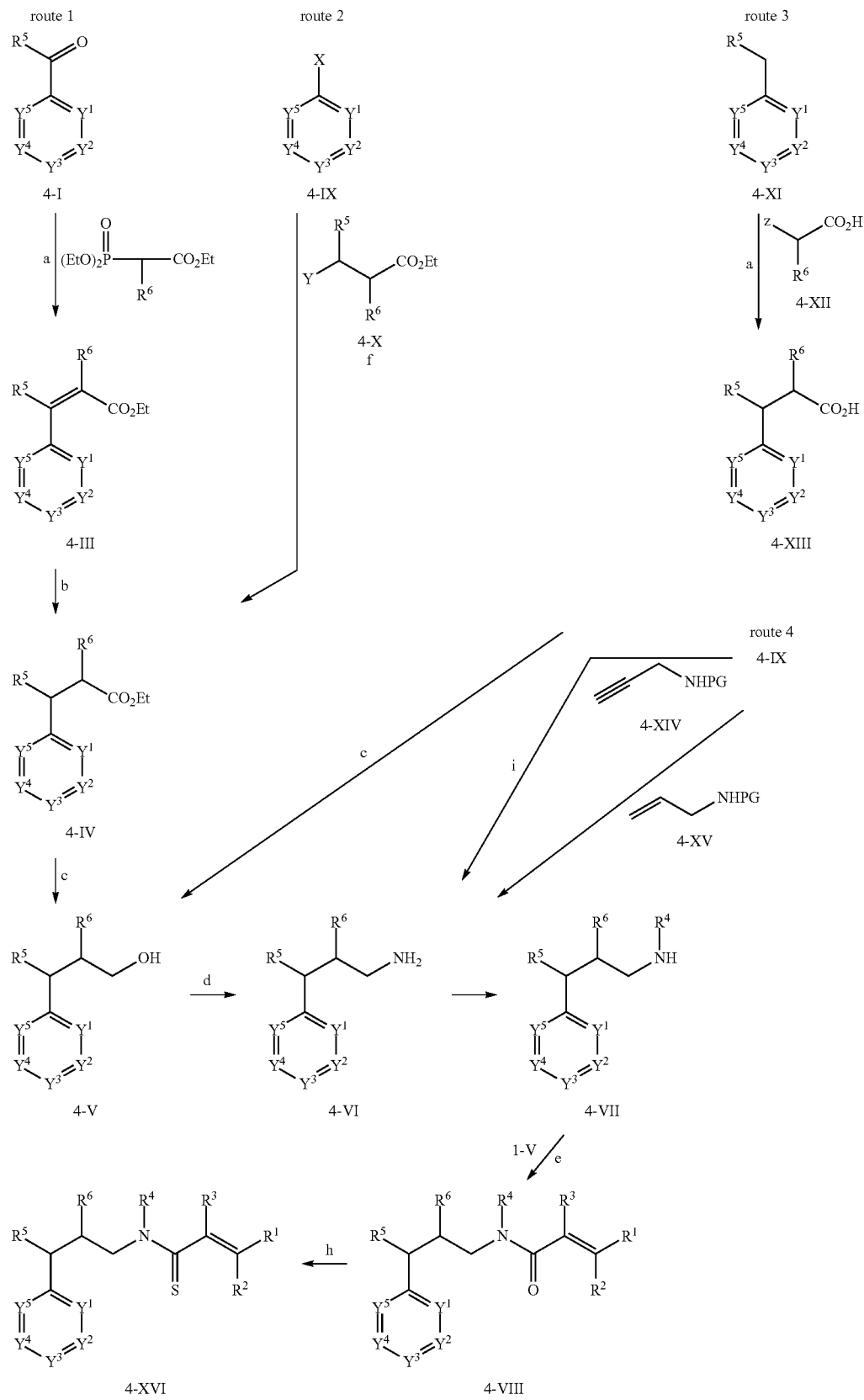

Exemplary conditions: a: THF, LiOH; b: hydrogen, ethanol, Pd/C; c: LiAlH$_4$; d: 1. phthalimide, PPh$_3$, N$_2$(COOEt)$_2$, THF, 2. N$_2$H$_4$, methanol; e: HBTU, EDIPA, DMF; f: Zn/Cu, Pd(PPh$_3$)$_2$, dimethylacetamide; g: NaNH$_2$, NH$_{3(l)}$; h: Lawesson's reagent, THF, 130° C.; i: Pd(PPh$_3$)$_2$Cl$_2$, 1,4-diazabicyclo[2,2,2]octane, THF.

A compound of general formula 4-VIII can be synthesized as shown in scheme 4: in route 1 a heteroarylcarbonyl compound 4-I is reacted with a phosphonic acid derivative 4-II in a Horner-Wadsworth-Emmons reaction to form the unsaturated ester 4-III which is reduced to the saturated ester 4-IV by methods known to a person skilled in the art, e.g. hydrogenation with a suitable catalyst like, for example, palladium on charcoal. Reduction of the ester to the alcohol 4-V by, for example, a hydride transferring reagent like lithium aluminium hydride is followed by transformation to the amine 4-VI. The latter transformation can be achieved by, for example, the known Gabriel synthesis via formation of an intermediate phthalimide. Substitution of the nitrogen in 4-VI to give 4-VII can be done by methods known to a person skilled in the art using, for example, alkylation agents like alkylhalogens or using reductive alkylation procedures as described in, for example, Smith, M. B.; March, J.; *March's Advanced Organic Chemistry*, John Wiley & Sons, Hoboken; New Jersey, 2007, 1288-1292. Acylation with the unsaturated acid 1-V under conditions that have been described in scheme 1 gives the final product 4-VIII. A person skilled in the art can choose an alternative route depending on the availability, for example commercial availability of starting materials. In route 2 a heteroaryl compound 4-IX containing a suitable leaving group X like a halogen, preferably a iodine, is reacted with a zincorganic reagent that is synthesized, for example in situ, from the ester 4-X containing a halogen atom Y, preferably an iodine, by methods known to a person skilled in the art, for example as described in Sakamoto, T., *Synthesis*, (1988), 485-486 to give the intermediate ester 4-IV. In route 3 a heteroarylalkyl compound 4-XI is reacted with a carboxylic acid 4-XII containing a halogen atom z to give the substituted acid 4-XIII as described in, for example, Adger, B. M., et. al. *J. Chem. Soc. Perkin Trans. I* (1988), 2791-2796, that is reduced to the hydroxy intermediate 4-V by methods known to a person skilled in the art. In route 4, a heteroaryl compound 4-IX containing a suitable leaving group X like a halogen, preferably an iodine or bromine, is reacted with a protected amine 4-XIV containing a terminal triple bond in a Sonogashira-type coupling. Reduction of the triple bond and removal of the protecting group yields the amine 4-VI. Alternatively, 4-IV can be obtained by coupling of the protected amine 4-XV containing a terminal double bond with 4-IX in a Heck-type reaction followed by reduction and deprotection. Conversion into the thiocarbonyl analogue 4-XVI can be achieved by treatment with, for example, Lawesson's reagent under microwave heating. Other methods are described in, for example, Smith, M. B.; March, J.; *March's Advanced Organic Chemistry*, John Wiley & Sons, Hoboken; New Jersey, 2007, 1277-1280.

Scheme 5:

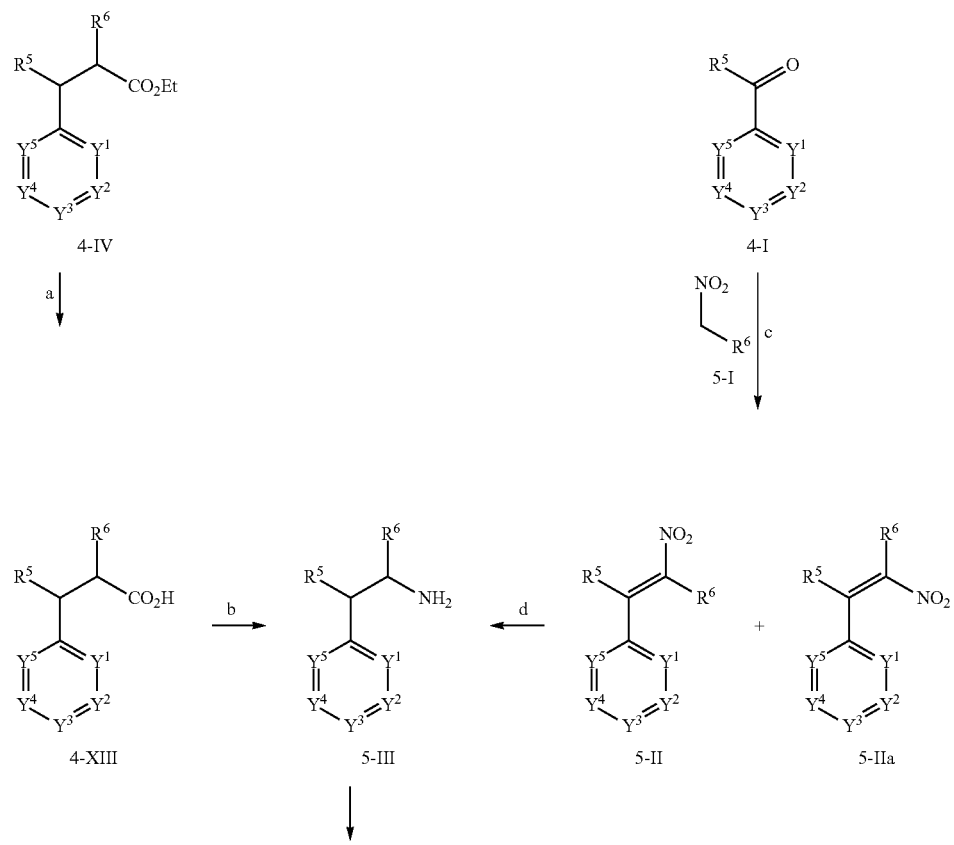

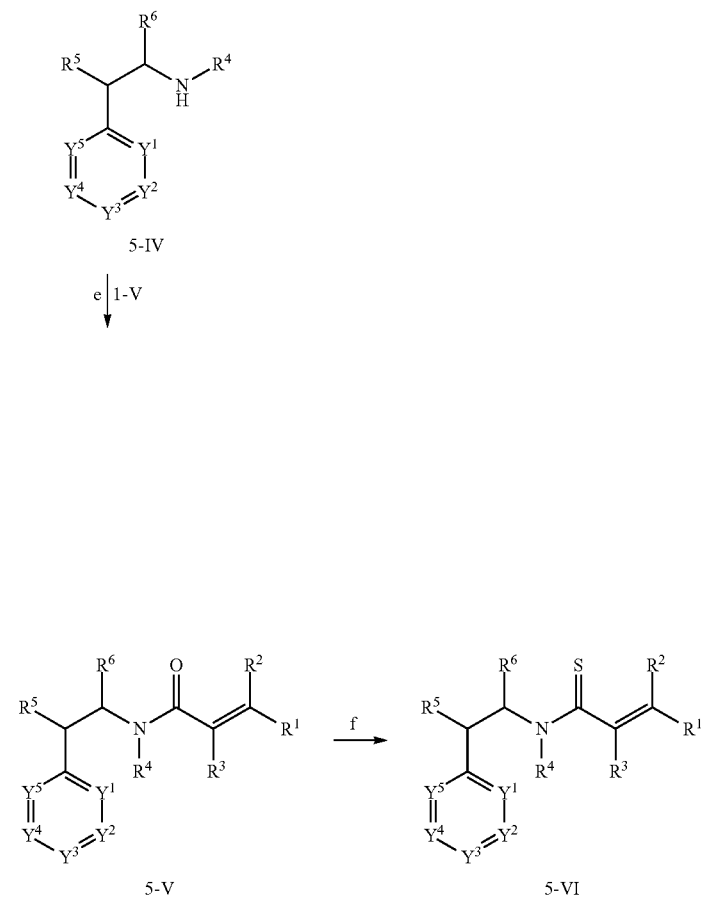

Exemplary conditions: a: NaOH, H$_2$O; b: NaN$_3$, H$_2$SO$_4$; c: 1. DCM, TEA 2. DCM, methanesulfonyl chloride, TEA; d: hydrogen, Raney nickel, methanol; e: HBTU, EDIPA, DMF; f: Lawesson's reagent, THF, 130° C.

Compounds of the general formula 5-V can be synthesized as shown in scheme 5: a heteroarylcarboxylic acid 4-XIII that has been described in scheme 4 is transformed into the amine 5-III with a Schmidt reaction as described in, for example, Claudi, F. et al. *Eur. J. Med. Chem.* 30(5), (1995), 415-421. 4-XIII can also be obtained by hydrolysis of the ester 4-IV that has been described in scheme 4. Alternatively, a heteroarylcarbonyl compound 4-I can be transformed into a mixture of 5-II and the isomeric 5-IIa as described in, for example, WO2008/125839 (example 36) followed by reduction to 5-III as described in, for example, Monti, D. et al. *Farmaco,* 36(6), (1981), 412-418. The primary amine in 5-III is then substituted as has been described in scheme 1 and acylation with a unsaturated acid as has been described in scheme 1 gives the final product 5-V. Conversion into the thiocarbonyl analogue 5-VI can be achieved by treatment with, for example, Lawesson's reagent under microwave heating.

Scheme 6:

route 1

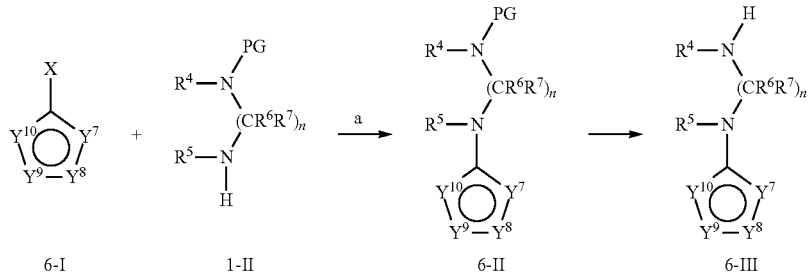

-continued route 2

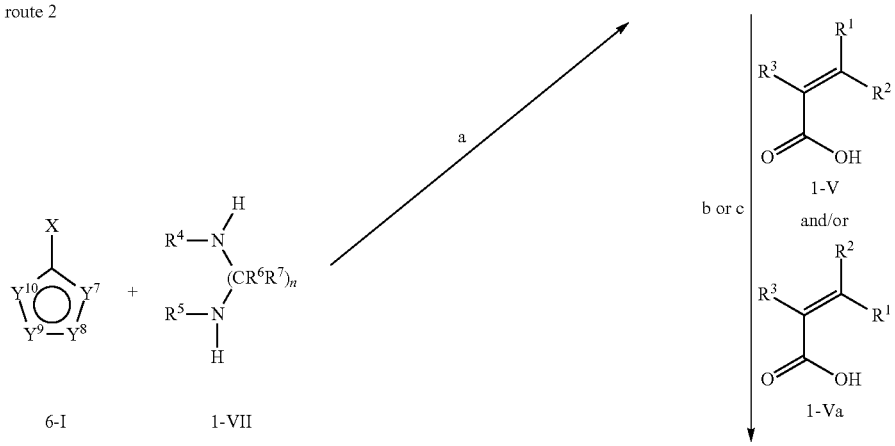

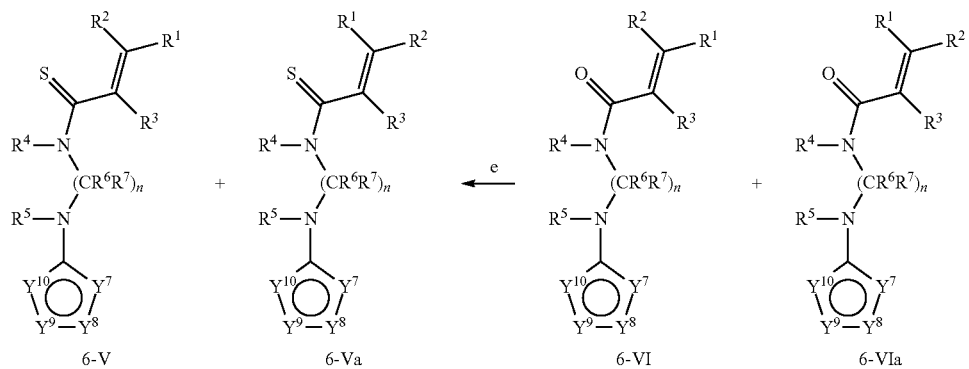

Exemplary conditions: a: $K_2CO_3$, 140° C. b: oxalyl chloride, DCM, DMF then DCM, TEA; c: HBTU, EDIPA, DMF, room temperature; d: Lawesson's reagent, THF, 130° C.

Compounds of general formula 6-VI can be synthesized as shown in scheme 6: In route 2 a heteroarylcopound 6-I is reacted with a diamine 1-VII to give 6-III. 6-I contains a suitable leaving group like chloro, bromo or a nitro group. The reaction can be carried out in a solvent like an alcohol, or a diol-derived solvent like ethylenglycolmonomethyl ether or in a solvent like dioxane or can be carried without solvent. A base might be present like, for example, potassium carbonate. The reaction is done preferably at elevated temperatures and the diamine 1-VII is used preferably in excess. The diamine can be monoprotected as 1-II (protection has been described in scheme 1) and used as described in route 1 to give 6-II. Deprotection under conditions already described in scheme 1 then gives the amino compound 6-III. Such a nucleophilic substitution of 6-I is suitable if 6-I is a pyrrol ($Y^7$ or $Y^{10}$ is N), thiophene ($Y^7$ or $Y^{10}$ is S), furane ($Y^7$ or $Y^{10}$ is O) or a benz-annulated derivative of these such as benzothiophene, benzofurane or benzopyrrol, wherein these heteroaromates are preferably substituted by electron-withdrawing substituents. Particularly suitable is such a reaction if 6-I is an imidazol ($Y^7$ and $Y^{10}$ are both N and one N is preferably substituted by preferably an alkyl group), a thiazol ($Y^7$ and $Y^{10}$ are N and S, respectively) or an oxazol ($Y^7$ and $Y^{10}$ are N and O, respectively) or a benz-annulated derivative thereof. Alternativly, the reaction between 6-I and the amine 1-II or 1-VII can be carried out under Pd-catalysis using a Pd source, a ligand like a phosphine ligand and a base as described in, for example, Hooper, M. W., et al. J. Org. Chem. 68, (2003), 2861-2873 or Charles, M. D., et al., Org. Lett. 7(18), (2005), 3965-3968. Pd-catalysis is especially useful if the heteroaromate 6-I is not activated towards nucleophilic substitution by carrying an electronwithdrawing substituent or if neither $Y^7$ nor $Y^{10}$ is a heteroatom. 6-III is then acylated by the unsaturated acid 1-V to give the amide 6-VI, as described in scheme 1. 1-V can be accompanied by the isomeric 1-Va so that a mixture of 6-VI and 6-VIa is obtained that can be separated by, for example, chromatography.

Scheme 7:

route 1

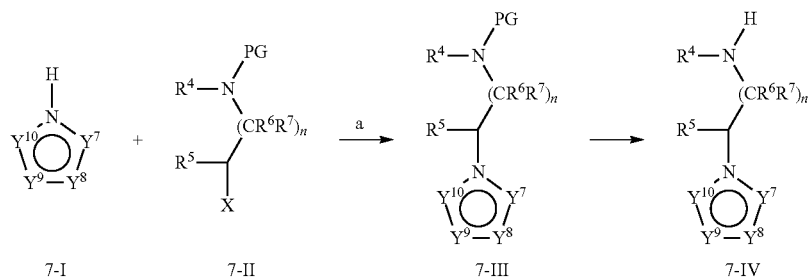

route 2

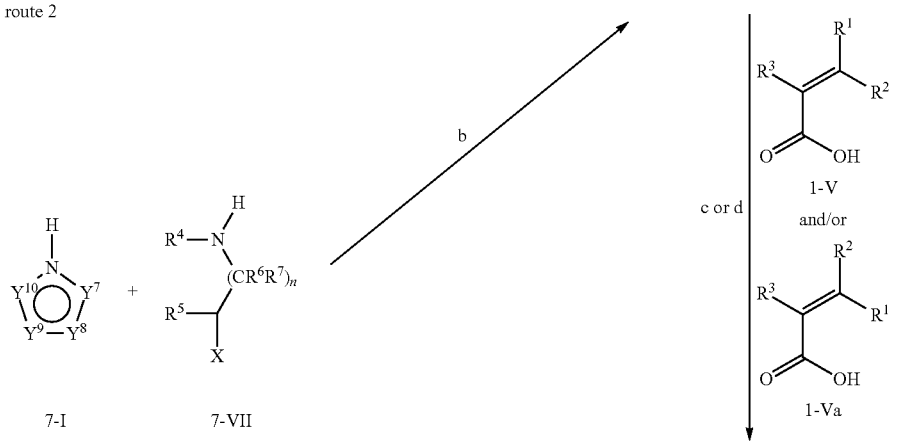

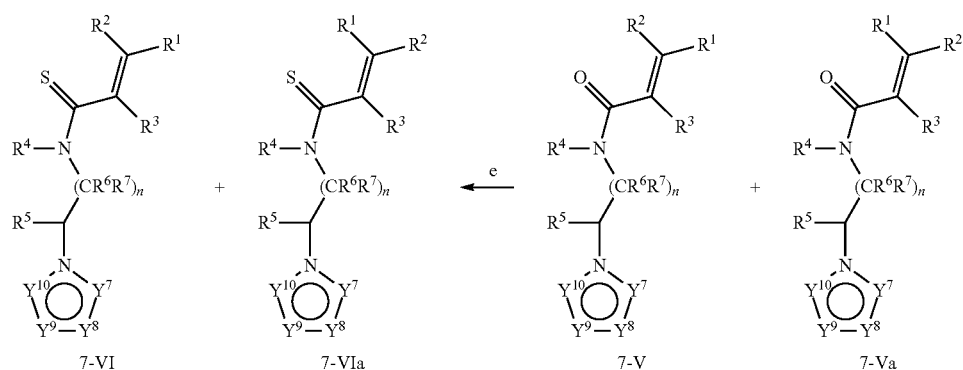

Exemplary conditions: a: NaH, DMF, 100° C.; b: acetonitrile, NaOH, tetrabutylammonium hydrogensulfate, heat; c: oxalyl chloride, DCM, DMF then DCM, TEA; c: HBTU, EDIPA, DMF, room temperature; d: Lawesson's reagent, THF, 130° C.

A compound of general formula 7-V can be obtained as described in scheme 7: the heteroarylcompound 7-I is reacted in route 1 with the alkylating agent 7-II which contains a protected nitrogen and a leaving group X which is, for example, a halogen like chloro or bromo in presence of a base like, for example, sodium hydride preferably at elevated temperatures as described in, for example, Buchholz, M., et al., *J. Med. Chem.* 49(2), (2006) 664-677. Alternatively, 7-I is alkylated with 7-VII containing an unprotected nitrogen in route 2 under, for example, phase-transfer conditions as described in, for example, He, Y. et al., *Org. Lett.* 13(17) (2011), 4490-4493, yielding 7-IV. 7-IV is then acylated as described in scheme 1 to yield 7-V which can be converted to its thioanalogue 7-VI as described in the preceding schemes.

Scheme 8:

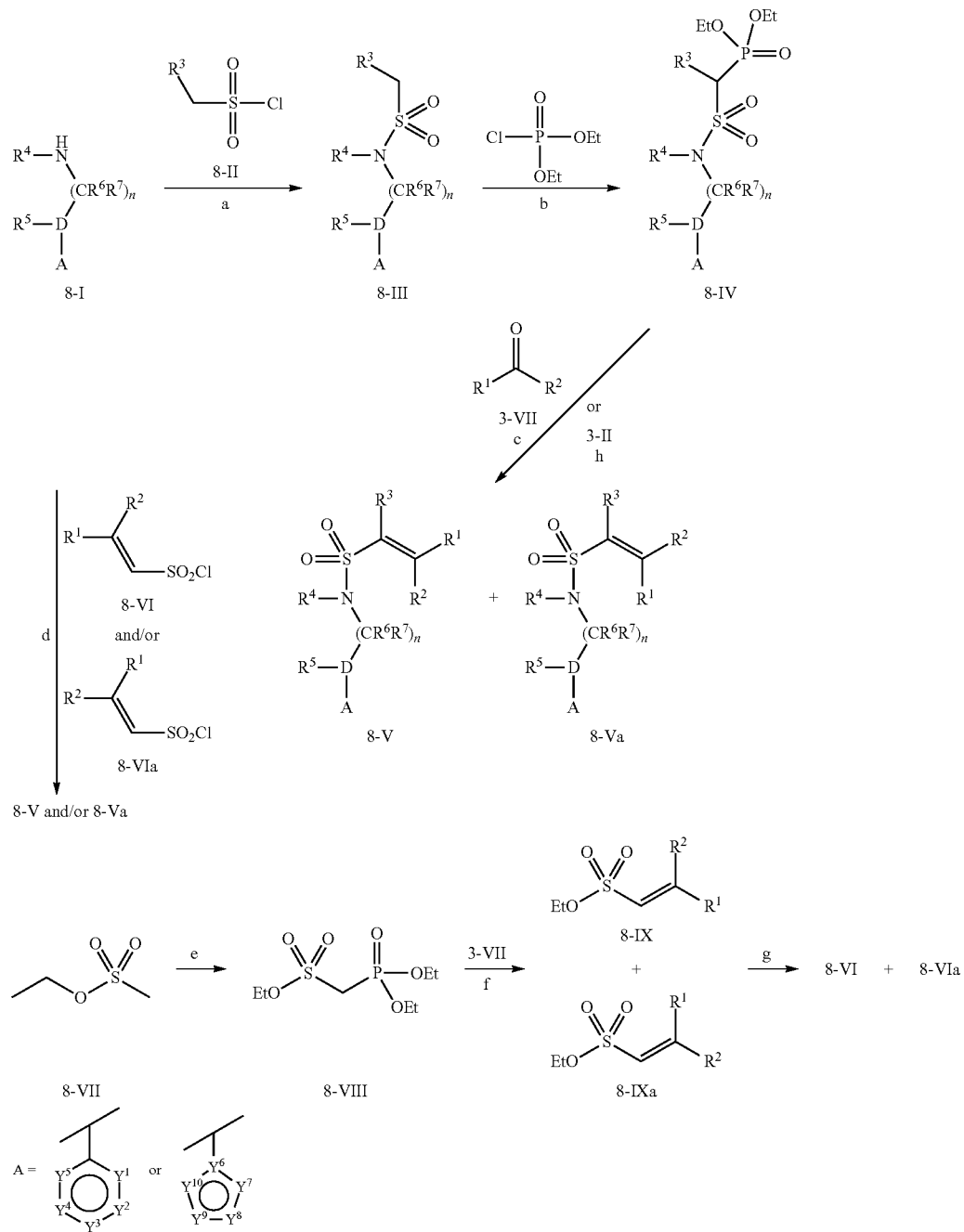

Exemplary conditions: a: DCM, TEA, 0° C.; b: LiN(Si(CH$_3$)$_3$)$_2$, THF, −78° C.; c: LiBr, DBU, THF, −10° C. to room temperature; d: TEA, DCM,; e: (EtO)$_2$POCl, n-butyllithium (n-BuLi), THF, −80° C.; f: tetrabutylammonium iodide, acetone, reflux; g: sulfuryl chloride, triphenylphosphine, DCM; h: NaH, THF, 0° C.

A compound of the general formula 8-V can be synthesized as shown in scheme 8: A compound 8-I which contains an NH-group is reacted with an alkylsulfonic acid chloride 8-II in the presence of a suitable base like triethylamine in a solvent like dichloromethane. 8-I can be synthesized, for example, according to schemes 1, 2, 4, 5, 6, or 7. The sulfonamide 8-III is deprotonated with a strong base like lithium diisopropylamide, lithium hexamethyldisilazide or n-butyllithium at low temperature like −78° C. and reacted with diethylchlorophosphate to give 8-IV. 8-IV is then reacted with a carbonylcompound 3-VII to give the final product 8-V. The last step can be carried out in the presence of lithium bromide and a strong base like 1,8-diaza-7-bicyclo[5.4.0]undecene (DBU), as described in, for example, Z. Wróbel, *Tetrahedron* 57 (2001), 7899-7907. Alternativly, the hemiacetal 3-II can be used instead of the carbonyl compound 3-VII and a strong base like sodium hydride. Depending on the nature of the radicals R$^1$, R$^2$ and R$^3$ the isomeric final products 8-V and 8-Va can be formed in differing proportions. For example, if $R^2$ is H and $R^3$ is H, then the E-isomer 8-V is formed predominantly. If a mixture of 8-V and 8-Va is formed, this can be separated by methods known to a person skilled in the art, e.g. by chromatography. Alternatively, the vinylsulfonyl chloride 8-VI can be synthesized first starting from the methanesulfonate 8-VII by deprotonation and reaction with diethylchlorophosphate, followed by deprotonation and reaction with a carbonylcompound 3-VII leading to the unsaturated sulfonate 8-IX which is converted to 8-VI. This sulfonyl chloride is then coupled to the amino compound 8-I to give the final product 8-VI.

joined together with $R^5$ to form a $C_1$-$C_3$ alkylene group can be synthesized as shown in scheme 9: A spirocyclic diamine 9-I is coupled to a heteroarylcompound 9-VIII to give 9-II. 9-I can be monoprotected by a suitable protecting group like the ones that have been described in scheme 1. The synthesis of compounds like 9-I has been described in, for example, Burckhard, J., Carreira, E. M., *Organic Lett.* 10 (2008), 3525-3526 and Burckhard, J., Guerot, C., Knust, H., Rogers-Evans, M., Carreira, E. M., *Organic Lett.* 12 (2010), 1944-1947. Pd-catalysis can be used employing a Pd-containing molecule like palladium acetate or $Pd_2(dba)_3$, a phosphorus-containing ligand like BINAP, a base like caesium carbonate or sodium tert-butoxide in a solvent like an ether-containing Scheme 9:

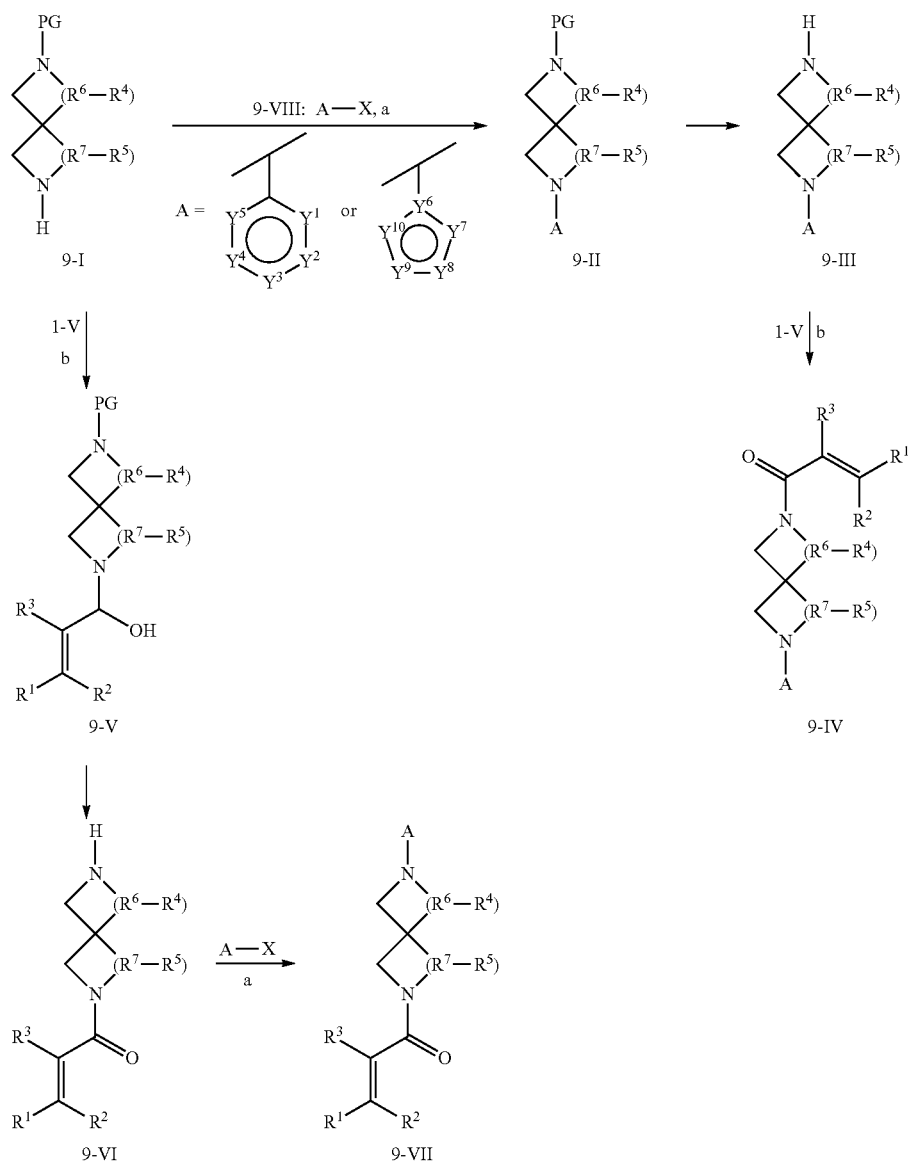

Exemplary conditions: a: $Pd_2(dba)_3$, BINAP, potassium tert.butylat, TEA, toluene, b: HBTU, diisopropylethylamine, DMF A spiro-compound that is formed when $R^6$ is joined together with $R^4$ to form a $C_1$-$C_3$ alkylene group and $R^7$ is solvent like diethylether, dioxane or tetrahydrofuran, or an inert solvent like toluene as described in, for example, Burckhard, J., Carreira, E. M., *Organic Lett.* 10 (2008), 3525-3526. Deprotection and acylation with an unsaturated acid 1-V gives the final product 9-IV. The sequence might be altered so that the spirocyclic diamine 9-I is first acylated to give 9-V. Deprotection and coupling with the heteroarylcompound 1-I gives 9-IV.

Heteroaryl compounds 1-I, 4-IX, 6-I and 7-I used as starting materials can be synthesized by several methods known to those skilled in the art. Quinoline derivatives are described in, for example, R. Kreher (editor), volume E7a of *Methods of Organic Chemistry (Houben-Weyl), Hetarenes II, part 1, 4th edition*, Georg Thieme Verlag, Stuttgart—New York, 1991; pyridine derivatives are described in, for example, R. Kreher (editor), volume E7b of *Methods of Organic Chemistry (Houben-Weyl), Hetarenes II, part 2, 4th edition*, Georg Thieme Verlag, Stuttgart—New York, 1992; pyrimidines, pyrazines, quinazolines and quinoxalines are described in, for example, E. Schaumann (editor), volume E9b of *Methods of Organic Chemistry (Houben-Weyl), Hetarenes IV, part 2a, 4th edition*, Georg Thieme Verlag, Stuttgart—New York, 1998; pyridazines and cinnolines in, for example, E. Schaumann (editor), volume E9a of *Methods of Organic Chemistry (Houben-Weyl), Hetarenes IV, part I, 4th edition*, Georg Thieme Verlag, Stuttgart—New York, 1997; 1,2-thiazoles, 1,2-benzothiazoles, 1,3-oxazoles and 1,3-benzoxazoles in, for example, E. Schaumann (editor), volume E8a of *Methods of Organic Chemistry (Houben-Weyl), Hetarenes III, part I, 4th edition*, Georg Thieme Verlag, Stuttgart—New York, 1993; 1,3-thiazoles, 1-3-benzothiazoles and pyrazoles in, for example, E. Schaumann (editor), volume E8b of *Methods of Organic Chemistry (Houben-Weyl), Hetarenes III, part 2—4th edition*, Georg Thieme Verlag, Stuttgart—New York, 1994; imidazoles, benzimidazoles and oxadiazoles in, for example, E. Schaumann (editor), volume E8c of *Methods of Organic Chemistry (Houben-Weyl), Hetarenes III, part 3, 4th edition*, Georg Thieme Verlag, Stuttgart—New York, 1994; thiadiazoles in, for example, E. Schaumann (editor), volume E8d of *Methods of Organic Chemistry (Houben-Weyl), Hetarenes III, part 4, 4th edition*, Georg Thieme Verlag, Stuttgart—New York, 1994; thiophenes, pyrroles and furanes in, for example, R. Kreher (editor), volume E6a of *Methods of Organic Chemistry (Houben-Weyl), Hetarenes I, part 1, 4th edition*, Georg Thieme Verlag, Stuttgart—New York, 1994; indoles and benzothiophenes in, for example, R. Kreher (editor), volume E6b of *Methods of Organic Chemistry (Houben-Weyl), Hetarenes I, part 2, 4th edition*, Georg Thieme Verlag, Stuttgart—New York, 1994. Many heteroaryl compounds 1-I used as starting materials are also commercially available by a large number of vendors as listed in, for example, the Symyx Available Chemicals Directory (ACD).

Amines 1-II, 1-VII, 2-I, used as starting materials are commercially available by a large number of vendors as well as carboxylic esters 3-I and 3-VIII, aldehydes 3-VIIa, ketones 4-I, halocarboxylic esters 4-X, halocarboxylic acids 4-XII, phosphonic acid derivatives 4-II and carbonyl compounds 3-VII as listed in, for example, the Symyx Available Chemicals Directory (ACD). In addition, carboxylic esters can be obtained by methods known to a person skilled in the art and described in, for example, J. Falbe (editor), volume E5 of *Methods of Organic Chemistry (Houben-Weyl), Carboxylic acids and Derivatives, part I, 4th edition*, Georg Thieme Verlag, Stuttgart—New York, 1985. Likewise, aldehydes can be obtained by methods described in, for example, J. Falbe (editor), volume E3 of *Methods of Organic Chemistry (Houben-Weyl), Aldehydes, 4th edition*, Georg Thieme Verlag, Stuttgart—New York, 1983 and ketones as described in, for example, volume VII, part 2 a-c of *Methods of Organic Chemistry (Houben-Weyl), Ketones I-III, 4th edition*, Georg Thieme Verlag, Stuttgart—New York, 1973-1977.

B. Synthesis Examples

The following examples are for illustrative purposes only and are not intended to limit the scope of the invention. The compounds were named using Symyx® draw version 3.1.Net software (Symyx Technologies, Inc.).

The methods described in the examples can be easily adapted by a person skilled in the art to make other compounds, and intermediates thereof. For instance, a person skilled in the art could replace in the examples the exemplified starting compounds by other compounds of the formulae 1-I, 1-II, 1-V, 1-VII, 1-IX, 2-I, 3-I, 3-II, 3-VII, 3-VIIa, 3-VIII, 4-I, 4-II, 4-IX, 4-X, 4-XI, 4-XII, 6-I, 7-I, 7-II, 7-VII, 8-I, 8-II, 8-VI, 8-VII (e.g. commercially available compounds), perform routine adaptions of the reaction conditions, if any, and use them for the synthesis of further compounds according to this invention.

Example 1

Synthesis of (E)-4,4,5,5,5-pentafluoro-N-[2-[(4-methyl-2-pyridyl)amino]ethyl]pent-2-enamide (A-5)

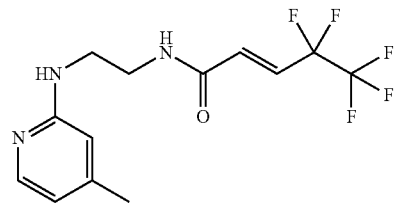 [SMILES: Cc1ccnc(NCCNC(=O)/C=C/C(F)(F)C(F)(F)F)c1]

Step A: 1-Ethoxy-2,2,3,3,3-pentafluoro-propan-1-ol

Ethyl 2,2,3,3,3-pentafluoropropionate (10.99 grams, 57.2 mmol) was dissolved in anhydrous methanol (57 ml) and cooled under argon to −60° C. Sodium borohydride (2.16 grams, 57.2 mmol) was added in four portions. After the addition was complete, stirring was continued for one hour and the temperature was held below −45° C. The mixture was cooled to −60° C. and 1M hydrochloric acid (172 ml) was added dropwise so that the temperature remained below −45° C. The mixture was slowly warmed to room temperature and extracted with diethylether (3×100 ml). The combined organic phases were washed with water (two times), dried over magnesium sulfate, the solvent was removed under reduced pressure. 9.76 g (50.3 mmol, 88%) were obtained and used directly in the next step.

Step B: 6,6,7,7,7-Pentafluoro-3-hydroxy-pentanoic acid

1-Ethoxy-2,2,3,3,3-pentafluoro-propan-1-ol (9.76 g, 50.3 mmol) was mixed with malonic acid (15.73 g, 0.15 mole), piperidine (0.611 ml) and pyridine (30 ml) and heated at 120° C. until gas evolution ceased (4 hours). The solvent was removed under reduced pressure, the residue treated with 1M hydrochloric acid and extracted with diethylether (3×). The combined organic phases were washed with water (2×), dried over magnesium sulfate, the solvent was removed under reduced pressure. 9.81 g (47.2 mmol, 94%) were obtained and used directly in the next step.

Step C: Ethyl 4,4,5,5,5-pentafluoro-3-hydroxy-pentanoate 6,6,7,7,7-Pentafluoro-3-hydroxy-pentanoic acid (9.81 g, 47.2 mmol) was dissolved in anhydrous ethanol (47 ml), concentrated sulfuric acid was added (0.534 ml) and the mixture was heated under reflux. A solution of hydrochloric acid in anhydrous methanol was added (1 M, 8 ml) and heating was continued for 3 hours. The solvent was removed under reduced pressure and 11.9 g were obtained which were used directly in the next step.

Step D: Ethyl (E)-4,4,5,5,5-pentafluoropent-2-enoate

Ethyl 4,4,5,5,5-pentafluoro-3-hydroxy-pentanoate (11.9 g from step C) was placed in a 25 ml round-bottom flask and phosphorus pentoxid was added in small portions until the educt was almost completely absorbed. The temperature was raised slowly to 140° C. until a brown sirup was obtained. The flask was connected to a distilling apparatus and the product isolated by distillation at reduced pressure (50 mbar, 50° C.). 5.5 g (25.2 mmol, 50% over 2 steps) were obtained.

Step E: (E)-4,4,5,5,5-Pentafluoropent-2-enoic acid

Ethyl (E)-4,4,5,5,5-pentafluoropent-2-enoate (5.5 g, 25.2 mmol) was suspended in 10% NaOH (14.5 ml) and heated at reflux until a homogenous solution was obtained (40 min). After cooling to room temperature the mixture was washed with diethylether (2×) and acidified under ice-cooling with concentrated sulfuric acid. The mixture was extracted with diethylether (3×), the combined organic phases were washed with water, dried over magnesium sulfate and the solvent removed under reduced pressure. 2.64 g (13.9 mmol, 55%) were obtained. MS (ES) m/z=189.0 [M-H]⁻.

Step F: (E)-4,4,5,5,5-pentafluoro-N-[2-[(4-methyl-2-pyridyl)amino]ethyl]pent-2-enamide (E)-4,4,5,5,5-Pentafluoropent-2-enoic acid (29 mg, 0.15 mmol) was dissolved in DMF (1 ml), oxalyl chloride was added (13 µl, 0.15 mmol) and the solution was stirred at room temperature for 5 minutes. To this solution was added a solution of N'-(4-methyl-2-pyridyl)ethane-1,2-diamine (19 mg, 0.1 mmol) in DMF (0.5 ml) and diisopropylethylamine (51 µl, 0.3 mmol) and the resulting mixture was stirred at room temperature for two hours. The reaction mixture was diluted with ethyl acetate, washed with sat. sodium bicarbonate solution and brine and dried over magnesium sulfate. The volatiles were removed under reduced pressure and the residue obtained was purified by preparative HPLC (Waters XBridge, gradient of water containing 0.1% NH₃ and 10% to 100% acetonitrile) to yield 18.5 mg (0.057 mmol, 57%).

Example 2

Synthesis of (E)-N-[2-[(4-ethoxy-2-pyridyl)amino]ethyl]-4,4-difluoro-pent-2-enamide (A-15)

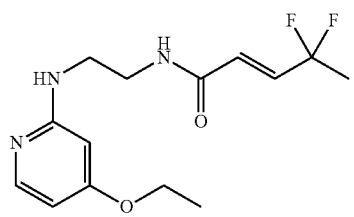 [SMILES: CCOc1ccnc(NCCNC(=O)/C=C/C(C)(F)F)c1]

Step A: Ethyl 4,4-difluoro-3-oxo-pentanoate

Lithium hexamethyldisilazide (150 ml of a 1M solution in THF, 0.15 mol) was cooled in an argon athmosphere to −78° C. and ethyl acetate (15 ml, 0.14 mol) was added dropwise with stirring. Stirring was continued for one hour at −78° C., then ethyl 2,2-difluoropropionate (12 g, 0.089 mol) was added dropwise with stirring. Stirring was continued for four hours at −78° C., then a saturated solution of ammonium chloride (175 ml) was added dropwise. The mixture was allowed to reach room temperature, acidified with 1M HCl (50 ml) and left standing overnight. The phases were separated. The aqueous phase was extracted with ethyl acetate, the combined organic phases were washed with 1M HCl, brine, dried over sodium sulfate. The solvent was removed under reduced pressure and the residue was purified by vacuum distillation (54 mbar, 130° C.) to yield 12.4 g (0.068 mmol, 77%) of a colourless liquid that was used directly in the next step.

Step B: Ethyl 4,4-difluoro-3-hydroxy-pentanoate

Ethyl 4,4-difluoro-3-oxo-pentanoate (12.4 g, 0.068 mmol) was dissolved in toluene (100 ml) and cooled to 0° C. Sodium borohydride (3.12 g, 0.083 g) was added portionwise, and the mixture was allowed to reach room temperature overnight with stirring. The mixture was then cooled to 0° C. and acidified with 1 m HCl. The phases were separated, the aqueous phase was extracted two times with ethyl acetate, the combined organic phases were dried over magnesium sulfate and the solvent was removed under reduced pressure. The residue was dissolved in a minimum amount of methanol, the resulting solution was evaporated to dryness under reduced pressure to yield 8.76 g of a residue (0.048 mol, 70%) that were used directly in the next step.

Step C: Ethyl (E)-4,4-difluoropent-2-enoate

Ethyl 4,4-difluoro-3-hydroxy-pentanoate (3.39 g, 0.0186 mol) was dissolved in THF (20 ml). Diphenyl-2-pyridylphosphin (7.37 g, 0.028 mol) was added followed after five minutes by di-$^{tert}$butylazodicarboxylate (2.83 g, 0.028 mol). The mixture was stirred for one hour at room temperature and left standing overnight. The mixture was acidified with trifluoroacetic acid (2 ml) and stirred for one hour at room temperature. The solvent was removed under reduced pressure and the residue partitioned between ethyl acetate and 4N HCl. The phases were separated, the organic phase was washed with 1M HCl (4×), dried over magnesium sulfate and evaporated to dryness. After distillation at 2 mbar 5.99 g were obtained which still contained some solvent but were used directly in the next step.

Step D: (E)-4,4-Difluoropent-2-enoic acid

The product of step C was dissolved in ethanol (24 ml), 4M NaOH was added (12 ml) and the mixture was stirred at room temperature for two hours. The mixture was acidified with 1M HCl and extracted with ethyl acetate. The organic extract was dried over magnesium sulfate, the solvent was removed under reduced pressure. 2.67 g of a colourless oil were obtained. MS(ESI) m/z=135.0 [M-1]⁻.

Step E: N-(4-Ethoxy-2-pyridyl)ethane-1,2-diamine

A mixture of 2-bromo-4-ethoxypyridine (500 mg, 2.475 mmol), ethane-1,2-diamine (9.9 ml, 150 mmol) and potassium carbonate (685 mg, 4.95 mmol) was stirred under microwave heating at 140° C. for 2 hours. The reaction mixture was filtered, the remaining solids were rinsed with ethanol and the combined filtrates were concentrated under reduced pressure and purified by flash column chromatography (silica, gradient of 2%-100% 7N NH3 in MEOH in DCM) to yield 287 mg of a solid (1.584 mmol, 64%). MS(ESI) m/z=182.0 [M+1]$^+$.

Step F: (E)-N-[2-[(4-Ethoxy-2-pyridyl)amino]ethyl]-4,4-difluoro-pent-2-enamide (E)-4,4-Difluoropent-2-enoic acid (31 mg, 0.23 mmol) was dissolved in dichloromethane (0.5 ml containing one drop of dimethyl formamide), oxalyl chloride was added (20 μl, 0.23 mmol) and the solution was stirred at room temperature for 15 minutes. This solution was added to a solution of N-(4-ethoxy-2-pyridyl)ethane-1,2-diamine (27 mg, 0.15 mmol) and diisopropylethylamine (88 μl, 0.5 mmol) dissolved in DCM (2 ml) and the resulting mixture was stirred at room temperature for three hours. The volatiles were removed under reduced pressure and the residue was purified by preparative HPLC (gradient of water containing 0.1% NH$_3$ and 10% to 100% acetonitrile) to yield 18.7 mg of a residue that was purified again by preparative HPLC (gradient of water containing 0.1% trifluoroacetic acid and 10% to 100% acetonitrile). The product obtained was converted to the free base by dissolving in DCM, washing with 1N NaOH solution, water and evaporation to dryness under reduced pressure to yield 13.2 mg of a solid (0.044 mmol, 29%).

Example 3

Synthesis of (E)-4,4,4-trifluoro-N-[2-[(6-methoxy-2-methyl-3-pyridyl)amino]ethyl]but-2-enamide (A-39)

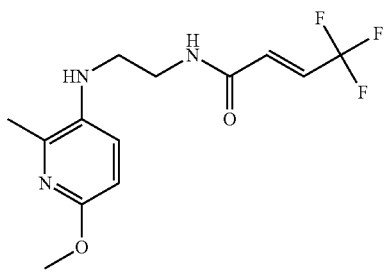 [SMILES: COc1ccc(NCCNC(=O)/C=C/C(F)(F)F)c(C)n1]

Step A:
N-(6-Methoxy-2-methyl-3-pyridyl)ethane-1,2-diamine

3-Bromo-6-methoxy-2-methylpyridine (50 mg, 0.247 mmol), ethane-1,2-diamine (0.083 ml, 1.237 mmol), sodium tert-butoxide (47.6 mg, 0.495 mmol) and dicyclohexyl-[3,6-dimethoxy-2-(2,4,6-thisopropylphenyl)phenyl]phosphane (6.64 mg, 0.012 mmol) were dissolved under argon in anhydrous 1,4-dioxane (2.5 ml). Next, Pd$_2$(DBA)$_3$ (11.33 mg, 0.012 mmol) was added and the mixture was heated in a sealed flask to 70 C overnight. The reaction mixture was filtered over kieselguhr, rinsed with EtOAc and the combined filtrates were concentrated under reduced pressure. The residue was purified by flash column chromatography (silica, gradient of 0.5% to 10% of [7N NH3 in MeOH] in DCM to yield 35 mg (0.193 mmol, 78%) of a yellow oil. MS(ESI) m/z=182.2 [M+1]$^+$.

Step B: (E)-4,4,4-Trifluoro-N-[2-[(6-methoxy-2-methyl-3-pyridyl)amino]ethyl]but-2-enamide (E)-4,4,4-Trifluorobut-2-enoic acid (33 mg, 0.23 mmol) was dissolved in DCM (1 ml containing one drop of dimethyl formamide), oxalyl chloride was added (20 μl, 0.23 mmol) and the solution was stirred at room temperature for 15 minutes. This solution was added to a solution of N-(6-methoxy-2-methyl-3-pyridyl)ethane-1,2-diamine (27 mg, 0.15 mmol) and diisopropylethylamine (88 μl, 0.5 mmol) in DCM (2 ml) and the resulting mixture was stirred at room temperature for three hours. The volatiles were removed under reduced pressure and the residue was purified by preparative HPLC (Waters XBridge, gradient of water containing 0.1% NH$_3$ and 10% to 100% acetonitrile) to yield 10.5 mg of a solid (0.035 mmol, 23%).

Example 4

Synthesis of (E)-4,4,4-trifluoro-N-[2-(2-quinolylamino)ethyl]but-2-enamide (A-42)

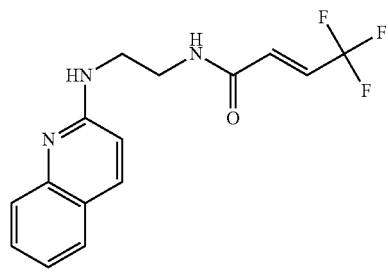 [SMILES: O=C(/C=C/C(F)(F)F)NCCNc1ccc2ccccc2n1]

Step A: tert-Butyl
N-[2-(2-quinolylamino)ethyl]carbamate

Palladium acetate (63 mg, 0.28 mmol), BINAP (250 mg, 0.4 mmol) and cesium carbonate (1.3 g, 4 mmol) were suspended in anhydrous 1,4-dioxane (9 ml) under an argon atmosphere and sonicated for 40 minutes. 2-Chloroquinoline (343 mg, 2 mmol) and tert-butyl N-(2-aminoethyl)carbamate (320 mg, 2 mmol) were added and the resulting mixture was stirred at 110° C. for three hours. The reaction mixture was diluted with ethyl acetate, the resulting precipitate was removed by centrifugation and decantation. The supernatant was evaporated to dryness under reduced pressure. The residue was dissolved in DCM, filtered through a short silica column; the product was eluted with a 1-to-1 mixture of DCM and diethylether. After evaporation of the solvent under reduced pressure 137 mg of a solid were obtained (0.44 mmol, 22%). MS(ESI) m/z=288.2 [M+1]$^+$.

Step B: N'-(2-Quinolyl)ethane-1,2-diamine
hydrochloride

Tert-butyl N-[2-(2-quinolylamino)ethyl]carbamate (137 mg, 0.44 mmol) was dissolved in a mixture of DCM (6 ml) and trifluoroacetic acid (2 ml) and left standing at room temperature for one hour. The volatiles were removed under reduced pressure, the residue was dissolved in THF and evaporated to dryness under reduced pressure. The residue was dissolved in THF and the product was precipitated by the addition of HCl in dioxane (4N). The precipitate was removed by filtration, washed several times with THF and dried under reduced pressure to yield 55 mg of a solid (0.226 mmol, 56%) that was used directly in the next step.

Step C: (E)-4,4,4-Trifluoro-N-[2-(2-quinolylamino)ethyl]but-2-enamide (E)-4,4,4-Trifluorobut-2-enoic acid (14 mg, 0.1 mmol) was dissolved in DCM (1 ml containing one drop of dimethyl formamide), oxalyl chloride was added (9 µl, 0.1 mmol) and the solution was stirred at room temperature for 10 minutes. This solution was added to a solution of N'-(2-quinolyl)ethane-1,2-diamine hydrochloride (22 mg, 0.1 mmol) in DMF (0.5 ml) followed by triethylamine (42 µl, 0.3 mmol) and the resulting mixture was stirred at room temperature for 40 minutes. Then another equivalent of the acid chloride solution (prepared from 14 mg (E)-4,4,4-trifluorobut-2-enoic acid, 1 ml DCM/DMF and 9 µl oxalyl chloride as described above) was added and stirring was continued for additional 40 minutes. The reaction mixture was diluted with ethyl acetate, washed with sat. sodium bicarbonate solution and brine and dried over magnesium sulfate. The volatiles were removed under reduced pressure and the residue obtained was purified by preparative HPLC (Waters XBridge, gradient of water containing 0.1% $NH_3$ and 5% to 100% acetonitrile) to yield 13 mg (0.042 mmol, 42%).

Example 5

Synthesis of (E)-4,4-difluoro-N-[2-[(4-methylthiazol-2-yl)amino]ethyl]pent-2-enamide (C-4)

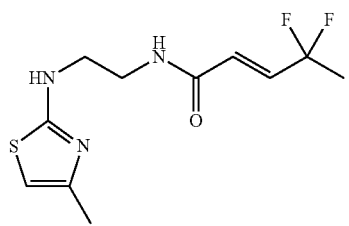 [SMILES: Cc1csc(NCCNC(=O)/C=C/C(C)(F)F)n1]

Step A: N'-(4-Methylthiazol-2-yl)ethane-1,2-diamine

A mixture of 2-bromo-4-methylthiazole (502 mg, 2.82 mmol), ethylenediamine (15 mL, 224 mmol) and potassium carbonate (780 mg, 5.64 mmol) was heated under microwave heating at 120° C. for 30 min in a closed vial. Ethanol (200 mL) was added, the resulting mixture was filtered, the solids washed with EtOH and the combined filtrates concentrated under reduced pressure. The residue was mixed with toluene and concentrated under reduced pressure; this step was repeated two times after which 620 mg of a solid was obtained that was used directly in the next step.

Step B: tert-Butyl N-[2-[(4-methylthiazol-2-yl)amino]ethyl]carbamate

To a solution of crude N'-(4-methylthiazol-2-yl)ethane-1,2-diamine (620 mg of Step A) in dichloromethane (25 mL) were added triethyl amine (785 ml, 5.65 mmol) and di-tert-butyl dicarbonate (625 mg, 2.86 mmol). The reaction mixture was stirred at room temperature for 18 hours. Saturated sodium bicarbonate solution was added, the layers were separated and the aqueous layer extracted twice with DCM. The combined organic layers were dried over sodium sulfate and concentrated under reduced pressure to yield 1.2 g of a residue that was purified by flash column chromatography (silica, gradient of 50% to 100% ethyl acetate in heptane). 435 mg of a white solid were obtained (1.69 mmol, 60% yield for two steps). MS(ESI) m/z=258.1 [M+1]$^+$.

Step C: N'-(4-Methylthiazol-2-yl)ethane-1,2-diamine hydrochloride

To a solution of tert-butyl N-[2-[(4-methylthiazol-2-yl)amino]ethyl]carbamate (435 mg, 1.69 mmol) in acetone (20 mL) was added HCl (4N in dioxane, 2.6 mL, 10.40 mmol) and the reaction mixture was stirred at room temperature overnight. The resulting precipitate was isolated by filtration, washed with acetone and diethylether and allowed to dry at ambient conditions to yield 290 mg of an off-white solid (1.497 mmol, 89%). MS(ESI) m/z=158.1 [M+1]$^+$.

Step D: (E)-4,4-Difluoro-N-[2-[(4-methylthiazol-2-yl)amino]ethyl]pent-2-enamide (E)-4,4-Difluoropent-2-enoic acid (31 mg, 0.23 mmol) was dissolved in DCM (0.5 ml containing one drop of dimethyl formamide), oxalyl chloride was added (20 µl, 0.23 mmol) and the solution was stirred at room temperature for 15 minutes. This solution was added to a solution of N'-(4-methylthiazol-2-yl)ethane-1,2-diamine hydrochloride (24 mg, 0.15 mmol) and diisopropylethylamine (88 µl, 0.5 mmol) dissolved in DCM (2 ml) and the resulting mixture was stirred at room temperature for three hours. The volatiles were removed under reduced pressure and the residue was purified by preparative HPLC (Waters XBridge, gradient of water containing 0.1% $NH_3$ and 10% to 100% acetonitrile) to yield 11 mg of a solid (0.04 mmol, 27%).

Example 6

Synthesis of (E)-4,4,4-trifluoro-N-[2-[(6-methylpyrazin-2-yl)amino]ethyl]but-2-enamide (A-80)

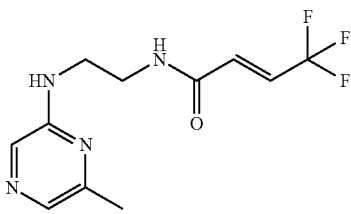 [SMILES: Cc1cncc(NCCNC(=O)/C=C/C(F)(F)F)n1]

Step A: N-(6-Methylpyrazin-2-yl)ethane-1,2-diamine

2-Bromo-6-methyl-pyrazine (220 mg, 1.44 mmol) was dissolved in ethylenediamine (2 ml) and stirred under microwave heating for 30 minutes at 150° C. in a closed vial. The reaction mixture was concentrated under reduced pressure, toluene was added and the volatiles were removed under reduced pressure. The last step was repeated two times. The remaining solid was used directly in the next step.

Step B: (E)-4,4,4-Trifluoro-N-[2-[(6-methylpyrazin-2-yl)amino]ethyl]but-2-enamide (E)-4,4,4-Trifluorobut-2-enoic acid (70 mg, 0.5 mmol) was dissolved in dichloromethane (1 ml containing one drop of dimethyl formamide), oxalyl chloride was added (42 μl, 0.5 mmol) and the solution was stirred at room temperature for 15 minutes. This solution was added to a solution of N-(6-methylpyrazin-2-yl)ethane-1,2-diamine (38 mg, 0.25 mmol) and EDIPA (175 μl, 1 mmol) in a mixture of anhydrous dichloromethane (2 ml) and anhydrous dimethylformamide (1 ml) and the resulting mixture was stirred at room temperature overnight. The reaction mixture was concentrated under reduced pressure and the resulting residue was purified by preparative HPLC (Waters XBridge, gradient of water containing 0.1% NH$_3$ and 10% to 100% acetonitrile) to yield 19.9 mg of a solid (0.07 mmol, 14.5% yield)

Example 7

Synthesis of (E)-4,4,4-trifluoro-N-[3-(4-methyl-2-pyridyl)propyl]but-2-enamide (A-120)

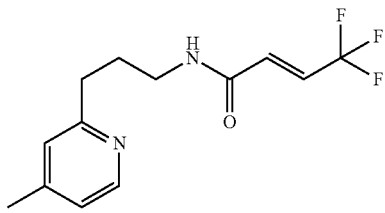 [SMILES: Cc1ccnc(CCCNC(=O)/C=C/C(F)(F)F)c1]

Step A: tert-Butyl N-[3-(4-methyl-2-pyridyl)prop-2-ynyl]carbamate

2-Bromo-4-methylpyridine (1 g, 5.81 mmol) was dissolved in anhydrous tetrahydrofurane (50 ml) and flushed with argon. N-Boc propagylamine (1.083 g, 6.98 mmol) and DABCO (1.304 g, 11.63 mmol) were added under argon followed by Pd(PPh$_3$)$_2$Cl$_2$ (0.204 g, 0.291 mmol) and copper (I) iodide (0.011 g, 0.058 mmol). The resulting mixture was stirred at room temperature for 72 hours. The mixture was filtered through kieselguhr, the filter residue was rinsed with ethyl acetate and the combined filtrates were concentrated under reduced pressure. The residue was purified by column chromatography (silica, gradient of 1 to 10% methanol containing 7N ammonia in DCM) and used directly in the next step. MS(ESI) m/z=247.2 [M+1]$^+$.

Step B: tert-Butyl N-[3-(4-methyl-2-pyridyl)propyl]carbamate

The residue of step A was dissolved in absolute ethanol (50 ml). The solution was flushed with argon, and a slurry of Pd/C (9.346 g, 0.325 mmol) in absolute ethanol (20 ml) was added. The resulting suspension was stirred in an athmosphere of hydrogen overnight. The reaction mixture was filtered and the filtrate was evaporated to dryness under reduced pressure. The residue was purified by column chromatography (silica, gradient of 1 to 5% methanol containing 7N ammonia in DCM) to yield 1.22 g (5.4 mmol, 84%, two steps). MS(ESI) m/z=251.2 [M+1]$^+$.

Step C: 3-(4-Methyl-2-pyridyl)propan-1-amine hydrochloride tert-Butyl N-[3-(4-methyl-2-pyridyl)propyl]carbamate (522 mg, 2.085 mmol) was dissolved in methanol (1 ml). A solution of HCl in methanol (4N, 41.7 mmol, 10.43 ml) was added and the mixture was stirred at room temperature for 2 hours. The mixture was concentrated under reduced pressure and triturated several times with diethyl ether. The residue was dried in vacuo to obtain a brown solid (409 mg, quantitative). MS(ESI) m/z=151.2 [M+1]$^+$.

Step D: (E)-4,4,4-Trifluoro-N-[3-(4-methyl-2-pyridyl)propyl]but-2-enamide (E)-4,4,4-Trifluorobut-2-enoic acid (64 mg, 0.46 mmol) was dissolved in dichloromethane (1 ml containing one drop of dimethyl formamide), oxalyl chloride was added (40 μl, 0.46 mmol) and the solution was stirred at room temperature for 15 minutes. This solution was added to a solution of 3-(4-methyl-2-pyridyl)propan-1-amine hydrochloride (56 mg, 0.3 mmol) and EDIPA (240 μl, 1.4 mmol) in anhydrous dichloromethane (5 ml) and the resulting mixture was stirred at room temperature for one hour. The reaction mixture was concentrated under reduced pressure and the resulting residue was purified by preparative HPLC (Waters XBridge, gradient of water containing 0.1% NH$_3$ and 10% to 100% acetonitrile) to yield 47 mg of a solid (0.17 mmol, 58% yield)

Example 8

Synthesis of (E)-4,4,4-trifluoro-N-[2-[(4-methyl-5-nitro-2-pyridyl)amino]-ethyl]but-2-enamide (A-147)

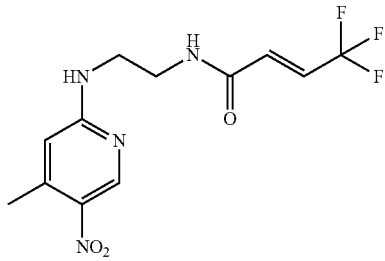 [SMILES: Cc1cc(NCCNC(=O)/C=C/C(F)(F)F)ncc1[N+](=O)[O-]]

Step A: N-(4-Methyl-5-nitro-2-pyridyl)ethane-1,2-diamine

To 2-chloro-4-methyl-5-nitro-pyridine (250 mg, 1.45 mmol) was added potassium carbonate (320 mg, 2.32 mmol) followed by ethylenediamine (4.2 g, 70 mmol). The mixture turned hot and was filtered after cooling through kieselguhr. The filtrate was concentrated under reduced pressure and purified by column chromatography (silica, gradient of 1 to 10% methanol containing 7N ammonia in DCM) to yield 205 mg (1.04 mmol, 72%) MS(ESI) m/z=197.1 [M+1]$^+$.

Step B: (E)-4,4,4-Trifluoro-N-[2-[(4-methyl-5-nitro-2-pyridyl)amino]ethyl]but-2-enamide (E)-4,4,4-Trifluorobut-2-enoic acid (32 mg, 0.23 mmol) was dissolved in dichloromethane (0.5 ml containing one drop of dimethyl formamide), oxalyl chloride was added (23 μl, 0.23 mmol) and the solution was stirred at room temperature for 15 minutes. This solution was added to a solution of N-(4-methyl-5-nitro-2-pyridyl)ethane-1,2-diamine (29 mg, 0.15 mmol) and EDIPA (70 µl, 0.5 mmol) in anhydrous dichloromethane (2 ml) and the resulting mixture was stirred at room temperature overnight. The reaction mixture was concentrated under reduced pressure and the resulting residue was purified by preparative HPLC (Waters XBridge, gradient of water containing 0.1% $NH_3$ and 10% to 100% acetonitrile) to yield 2.4 mg of a solid (0.0076 mmol, 5% yield).

Example 9

Synthesis of (E)-4,4-difluoro-N-[2-[(6-methoxy-4-methyl-2-pyridyl)amino]ethyl]pent-2-enamide (A-134)

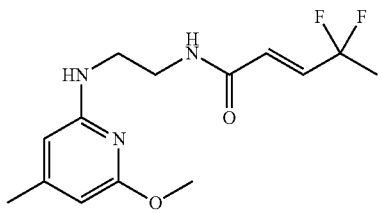 [SMILES: COc1cc(C)cc(NCCNC(=O)/C=C/C(C)(F)F)n1]

Step A:
N-(6-Bromo-4-methyl-2-pyridyl)ethane-1,2-diamine

To 2-bromo-6-fluoro-4-methyl-pyridine (380 mg, 2 mmol) was added potassium carbonate (552 mg, 4 mmol) followed by ethylenediamine (3 ml) and the resulting mixture was stirred art room temperature for two hours. The mixture was filtered through kieselguhr and the filtrate was evaporated to dryness under reduced pressure to yield 256 mg (1.11 mmol, 56%) MS(ESI) m/z=230.0 $[M+1]^+$.

Step B:
N-(6-Methoxy-4-methyl-2-pyridyl)ethane-1,2-diamine

Sodium (45 mg, 1.96 mmol) was dissolved in methanol (1.5 ml), N-(6-bromo-4-methyl-2-pyridyl)ethane-1,2-diamine (69 mg, 0.3 mmol) was added and the resulting mixture was stirred under microwave heating at 140° C. for three hours. The mixture was concentrated under reduced pressure and the residue was washed several times with ethyl acetate and acetonitrile. The washing solutions were decanted from the solid, the combined washing solutions were evaporated to dryness under reduced pressure to yield 58 mg. MS(ESI) m/z=182.0 $[M+1]^+$.

Step C: (E)-4,4-Difluoro-N-[2-[(6-methoxy-4-methyl-2-pyridyl)amino]ethyl]pent-2-enamide (E)-4,4-Difluoropent-2-enoic acid (16 mg, 0.12 mmol) was dissolved in a mixture of anhydrous dichloromethane (1 ml) and anhydrous dimethylformamide (0.5 ml), oxalyl chloride was added (11 µl, 0.12 mmol) and the solution was stirred at room temperature for 10 minutes. This solution was added to a solution of N-(6-Methoxy-4-methyl-2-pyridyl)ethane-1,2-diamine (22 mg, 0.12 mmol) and triethylamine (42 µl, 0.3 mmol) in anhydrous dimethylformamide (0.5 ml) and the resulting mixture was stirred at room temperature for thirty minutes. Another equivalent of acid chloride was prepared as described above and added, after which stirring was continued for 30 minutes. The reaction mixture was diluted with ethyl acetate, washed with saturated sodium bicarbonate solution (2 times), brine and the organic phase was dried over magnesium sulfate. After filtration and evaporation to dryness under reduced pressure the residue was purified by preparative HPLC (Waters XBridge, gradient of water containing 0.1% $NH_3$ and 10% to 100% acetonitrile) to yield 3.3 mg of a solid (0.011 mmol, 9% yield).

Example 10

Synthesis of (E)-4,4,4-Trifluoro-N-[2-[(4-methyl-2-pyridyl)amino]ethyl]pent-2-enethioamide (A-119)

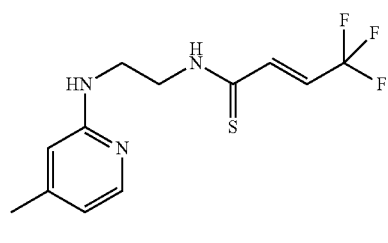 [SMILES: Cc1ccnc(NCCNC(=S)/C=C/C(F)(F)F)c1]

Step A: (E)-4,4,4-Trifluoro-N-[2-[(4-methyl-2-pyridyl)amino]ethyl]pent-2-enamide (E)-4,4,4-Trifluorobut-2-enoic acid (28 mg, 0.2 mmol) was dissolved in anhydrous dichloromethane (1.5 ml containing a drop of dimethylformamide), cooled to 0° C., oxalyl chloride was added (20 µl, 0.2 mmol) and the solution was stirred at room temperature for 10 minutes. This solution was added to a solution of N-(4-methyl-2-pyridyl)ethane-1,2-diamine (30 mg, 0.2 mmol) and triethylamine (42 µl, 0.3 mmol) in anhydrous dimethylformamide (0.5 ml) and the resulting mixture was stirred at room temperature for one hour. The reaction mixture was diluted with ethyl acetate, washed with saturated sodium bicarbonate solution and brine and the organic phase was dried over magnesium sulfate. After filtration and evaporation to dryness under reduced pressure the residue was used directly in the next step. MS(ESI) m/z=274.1 $[M+1]^+$.

Step B: (E)-4,4,4-Trifluoro-N-[2-[(4-methyl-2-pyridyl)amino]ethyl]pent-2-enethioamide (E)-4,4,4-Trifluoro-N-[2-[(4-methyl-2-pyridyl)amino]ethyl]pent-2-enamide from step A was dissolved in THF (2 ml) and combined with Lawesson's reagent (40 mg, 0.2 mmol) and stirred under microwave heating at 100° C. for 30 minutes. The mixture was evaporated to dryness under reduced pressure and purified by preparative HPLC (Waters XBridge, gradient of water containing 0.1% $NH_3$ and 10% to 100% acetonitrile) to yield 20 mg of a solid (0.069 mmol, 34% for two steps).

Example 11

Synthesis of (E)-3,3,3-trifluoro-N-[2-[(4-methyl-2-pyridyl)amino]ethyl]prop-1-ene-1-sulfonamide (A-122)

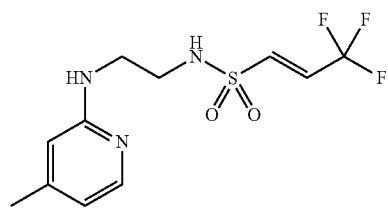 [SMILES: Cc1ccnc(NCCNS(=O)(=O)/C=C/C(F)(F)F)c1]

Step A: N-[2-[(4-Methyl-2-pyridyl)amino]ethyl]methanesulfonamide

To a cooled (0° C.) solution of N-(4-methyl-2-pyridyl)ethane-1,2-diamine (683 mg, 4.52 mmol) in dichloromethane (25 ml) were added triethyl amine (1.26 ml, 9.06 mmol) followed by methanesulfonyl chloride (370 μl, 4.78 mmol). The mixture was stirred at room temperature for two hours and washed with saturated sodium bicarbonate solution. The organic phase was dried over sodium sulfate and concentrated to give 1.04 g of a yellow oil (4.57 mmol, 95%) MS(ESI) m/z=230.1 [M+1]⁺.

Step B: tert-Butyl N-[2-[tert-butoxycarbonyl-(4-methyl-2-pyridyl)amino]ethyl]carbamate To a solution of N-[2-[(4-methyl-2-pyridyl)amino]ethyl]methanesulfonamide (1.04 g, 4.57 mmol) in dichloromethane (35 ml) were added triethyl amine (2.52 ml, 18.13 mmol) followed by tert-butoxycarbonyl tert-butyl carbonate (5.05 g, 23.14 mmol). The mixture was stirred at room temperature for 28 hours and partitioned between saturated sodium bicarbonate solution and DCM, the layers were separated, the aqueous layer was extracted twice with DCM, the combined organic layers were dried over sodium sulfate and concentrated under reduced pressure to give a residue that was purified by column chromatography (silica, gradient of 5 to 100% heptane in ethyl acetate) to yield 1.33 g of a thick colourless oil (3.1 mmol, 68%) MS(ESI) m/z=430.2[M+1]⁺.

Step C: tert-Butyl N-[2-(tert-butoxycarbonyl(diethoxyphosphorylmethylsulfonyl)amino)-ethyl]-N-(4-methyl-2-pyridyl)carbamate To a cooled solution (−78° C.) of tert-butyl N-[2-[tert-butoxycarbonyl-(4-methyl-2-pyridyl)amino]-ethyl]carbamate (1.33 g from step B, 3.1 mmol) in anhydrous THF (100 ml) was added under nitrogen a solution of lithium hexamethyldisilazide (1M in THF, 9.3 ml, 9.3 mmol) and the resulting mixture was stirred at −78° C. for two hours. Diethyl chlorophosphate (1.79 ml, 12.39 mmol) was added dropwise, stirring was continued and the mixture was allowed to reach room temperature over four hours. The reaction was quenched by the addition of a saturated solution of ammonium chloride and extracted with DCM (3 times), the combined organic layers were dried over sodium sulfate and concentrated under reduced pressure. The resulting residue was purified by column chromatography (silica, gradient of 20 to 100% heptane in ethyl acetate) to yield 0.699 g of a sticky oil (1.236 mmol, 40%) MS(ESI) m/z=566.2 [M+1]⁺.

Step D: tert-Butyl N-(4-methyl-2-pyridyl)-N-[2-[[(E)-3,3,3-trifluoroprop-1-enyl]sulfonyl-amino]ethyl]carbamate To a solution of tert-butyl N-[2-(tert-butoxycarbonyl(diethoxyphosphorylmethyl-sulfonyl)amino)-ethyl]-N-(4-methyl-2-pyridyl)carbamate (344 mg, 0.608 mmol) in anhydrous THF (30 ml) were added molsieve (4A) and sodium hydride (42.5 mg, 1.063 mmol, 60%) under nitrogen and the mixture was stirred at room temperature for 10 minutes. The mixture was cooled to 0° C. and 1-ethoxy-2,2,2-trifluoroethanol (220 mg, 1.525 mmol, 180 μl) was added. Stirring was continued for 30 minutes at 0° C. and overnight at room temperature. The mixture was filtered through kieselguhr and the filtrate was concentrated under reduced pressure. The residue was purified by column chromatography (silica, gradient of 0 to 100% heptane in ethyl acetate) to yield 98 mg of a colourless oil (0.239 mmol, 39%) MS(ESI) m/z=410.1 [M+1]⁺.

Step E: (E)-3,3,3-Trifluoro-N-[2-[(4-methyl-2-pyridyl)amino]ethyl]prop-1-ene-1-sulfonamide To a cooled solution (0° C.) of tert-butyl N-(4-methyl-2-pyridyl)-N-[2-[[(E)-3,3,3-trifluoroprop-1-enyl]sulfonylamino]ethyl]carbamate (190 mg, 0.464 mmol) in dioxane (10 ml) was added HCl (4M solution in dioxane, 3.5 ml, 14 mmol). The mixture was stirred at 0° C. for 30 minutes and then for 48 hours at room temperature. The mixture was evaporated to dryness under reduced pressure and the residue was partitioned between saturated sodium bicarbonate solution and DCM. Layers were separated and the aqueous layer was extracted with DCM (2×). The combined organic layers were dried over sodium sulfate, concentrated under reduces pressure and the residue was purified by column chromatography (silica, gradient of 10 to 100% heptane in ethyl acetate) to yield 103 mg of a white solid (0.33 mmol, 72%)

Example 12

Synthesis of (E)-N-[2-[ethyl-(4-methyl-2-pyridyl)amino]ethyl]-4,4,4-trifluoro-but-2-enamide (B-7)

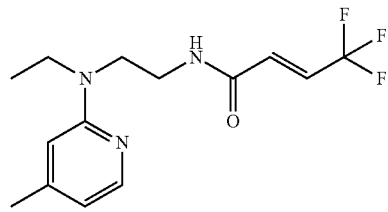 [SMILES: CCN(CCNC(=O)/C=C/C(F)(F)F)c1cc(C)ccn1]

Step A: 2-Chloro-4-methyl-pyridine 1-oxide

2-Chloro-4-methylpyridine (1 g, 7.84 mmol) was dissolved in DCM (10 ml), cooled to 0° C., mCPBA (70%, 2.32 g, 9.41 mmol) was added and the mixture was stirred at 0° C. for several hours and allowed to reach room temperature overnight. The mixture was diluted with DCM and washed with saturated Na₂S₂O₃ solution and saturated sodium bicarbonate solution. After drying (sodium sulfate) and concentration under reduced pressure, 1.0 g of a yellow oil was obtained (6.27 mmol, 80%) MS(ESI) m/z=144.0 [M+1]⁺.

Step B: tert-Butyl N-[2-[ethyl-(4-methyl-1-oxo-2-pyridyl)amino]ethyl]carbamate 2-Chloro-4-methyl-pyridine 1-oxide (200 mg, 1.393 mmol) and tert-butyl N-(2-aminoethyl)carbamate hydrochloride (783 mg, 3.48 mmol) were added to t-amyl alcohol (10 ml). Sodium carbonate (878 mg, 10.45 mmol) was added and the mixture was heated under reflux for 3 days. The mixture was concentrated under reduced pressure, the residue was partitioned between DCM and water. The layers were separated, the aqueous phase was extracted with DCM (4×), the combined organic phases were dried (sodium sulfate) and concentrated under reduced pressure to give a brown oil which was purified by column chromatography (silica, gradient of 1 to 10% methanol in DCM). 174 mg were obtained (0.59 mmol, 42%) MS(ESI) m/z=296.2 [M+1]⁺.

Step C: tert-Butyl N-[2-[ethyl-(4-methyl-2-pyridyl)amino]ethyl]carbamate tert-Butyl N-[2-[ethyl-(4-methyl-1-oxo-2-pyridyl)amino]ethyl]carbamate (174 mg, 0.59 mmol), Pd on charcoal (10%, 125 mg, 0.118 mmol) and cyclohexene (250 μl, 2.465 mmol) were added to absolute ethanol (10 ml) and the mixture was heated and stirred under reflux over night. Additional cyclohexene (250 μl) was added and heating was continued for 4 hours after which the mixture was allowed to reach room temperature overnight. The mixture was filtered through kieselguhr, concentrated under reduced pressure and purified by column chromatography (silica, gradient of 0 to 50% ethyl acetate in heptane) to yield 130 mg (0.465 mmol, 79%) MS(ESI) m/z=280.2 [M+1]$^+$.

Step D: N-Ethyl-N-(4-methyl-2-pyridyl)ethane-1,2-diamine dihydrochloride tert-Butyl N-[2-[ethyl-(4-methyl-2-pyridyl)amino]ethyl] carbamate (130 mg, 0.465 mmol) was dissolved in DCM (10 ml) and flushed with nitrogen. Hydrochloric acid (4N in dioxane, 9.31 mmol, 2.33 ml) was added and the mixture was stirred at room temperature overnight. The product was filtered off, dissolved in a mixture of acetonitrile and water and obtained by evaporation under reduced pressure to yield 58 mg (0.229 mmol, 49%) MS(ESI) m/z=180.2 [M+1]$^+$.

Step E: (E)-N-[2-[Ethyl-(4-methyl-2-pyridyl)amino] ethyl]-4,4,4-trifluoro-but-2-enamide (E)-4,4,4-Trifluorobut-2-enoic acid (32 mg, 0.23 mmol) was dissolved in dichloromethane (0.5 ml containing one drop of dimethyl formamide), oxalyl chloride was added (20 μl, 0.23 mmol) and the solution was stirred at room temperature for 15 minutes. This solution was added to a solution of N-ethyl-N-(4-methyl-2-pyridyl)ethane-1,2-diamine dihydrochloride (38 mg, 0.15 mmol) and EDIPA (128 μl, 0.8 mmol) in anhydrous dichloromethane (2 ml) and the resulting mixture was stirred at room temperature overnight. The reaction mixture was concentrated under reduced pressure and the resulting residue was purified by preparative HPLC (Waters XBridge, gradient of water containing 0.1% NH$_3$ and 10% to 100% acetonitrile) to yield 29 mg of a solid (0.096 mmol, 64% yield).

Example 13

Synthesis of (E)-4,4,4-trifluoro-1-[7-(4-methyl-2-pyridyl)-2,7-diazaspiro[4.5]decan-2-yl]but-2-en-1-one (B-1)

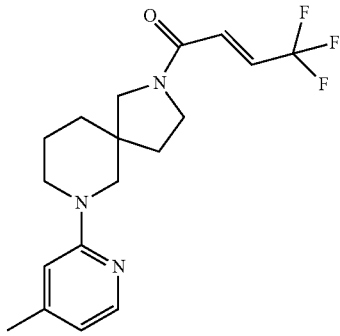 [SMILES: Cc1ccnc(N2CCCC3(CCN(C(=O)/C=C/C(F)(F)F)C3)C2)c1]

Step A: tert-Butyl 7-(4-methyl-2-pyridyl)-2,7-diazaspiro[4.5]decane-2-carboxylate 2-Bromo-4-methylpyridine (172 mg, 1 mmol) and tert-butyl 3,7-diazaspiro[4.5]decane-3-carboxylate (1 mmol, 240 mg) were dissolved in anhydrous dioxane (5 ml) under argon. Pd$_2$(dba)$_3$ (0.0165 mmol, 15 mg), Brettphos (30 mg, 0.0495 mmol), and sodium tert-butoxide (80 mg, 0.83 mmol) were added and the mixture was stirred at 100° C. overnight. Additional 2-bromo-4-methylpyridine (0.9 mmol, 100 μl) was added and stirring was continued at 100° C. overnight. The mixture was diluted with ethyl acetate, filtered through a plug of silica and concentrated under reduced pressure. The residue was purified by column chromatography (silica, gradient of 0 to 20% ethyl acetate in DCM) to yield 50 mg (0.15 mmol, 15%) MS(ESI) m/z=332.2 [M+1]$^+$.

Step B: 7-(4-Methyl-2-pyridyl)-2,7-diazaspiro[4.5]decane dihydrochloride

The residue of step A was dissolved in a mixture of methanol and hydrochloric acid (4M in dioxane, 5 ml) and stirred at room temperature overnight. The mixture was concentrated under reduced pressure to yield 79 mg of a solid (quantitive) that was used directly in the next step.

Step C: (E)-4,4,4-Trifluoro-1-[7-(4-methyl-2-pyridyl)-2,7-diazaspiro[4.5]decan-2-yl]but-2-en-1-one (E)-4,4,4-Trifluorobut-2-enoic acid (32 mg, 0.23 mmol) was dissolved in dichloromethane (0.5 ml containing one drop of dimethyl formamide), oxalyl chloride was added (20 μl, 0.23 mmol) and the solution was stirred at room temperature for 15 minutes. This solution was added to a solution of 7-(4-methyl-2-pyridyl)-2,7-diazaspiro[4.5]decane dihydrochloride (40 mg, 0.13 mmol, half of the residue from step B) and EDIPA (125 μl, 0.8 mmol) in anhydrous dichloromethane (2 ml) and the resulting mixture was stirred at room temperature overnight. The reaction mixture was concentrated under reduced pressure and the resulting residue was purified by preparative HPLC (Waters XBridge, gradient of water containing 0.1% NH$_3$ and 10% to 100% acetonitrile) to yield 10 mg of a solid (0.028 mmol, 9% yield for two steps).

Example 14

Synthesis of (E)-4,4,4-trifluoro-N-methyl-N-[2-[methyl-(5-methyl-3-pyridyl)amino]ethyl]-but-2-enamide (B-14)

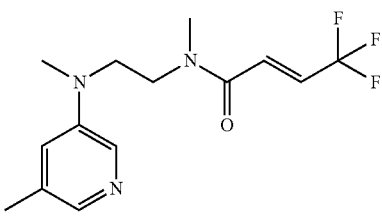 [SMILES: Cc1cncc(N(C)CCN(C)C(=O)/C=C/C(F)(F)F)c1]

Step A: tert-Butyl N-methyl-N-[2-[methyl-(5-methyl-3-pyridyl)amino]ethyl]carbamate 3-Bromo-5-methylpyridine (350 mg, 2.035 mmol), tert-butyl N-methyl-N-(2-methylaminoethyl)carbamate (686 mg, 3.05 mmol), RuPhos (47.5 mg, 0.102 mmol) and sodium tert-butoxide (489 mg, 5.09 mmol) were combined in anhydrous toluene (15 ml). The mixture was purged with argon, tris(dibenzylideneacetone)dipalladium (0) chloroform complex (105 mg, 0.102 mmol) was added and the mixture was stirred at 100° C. overnight. The mixture was filtered through kieselguhr, concentrated under reduced pressure and the residue was purified by column chromatography (silica, gradient of 10 to 50% ethyl acetate in heptane) to yield 301 mg (1.078 mmol, 53%) MS(ESI) m/z=280.2 [M+1]⁺.

Step B: N,N'-Dimethyl-N-(5-methyl-3-pyridyl)ethane-1,2-diamine dihydrochloride tert-Butyl N-methyl-N-[2-[methyl-(5-methyl-3-pyridyl)amino]ethyl]carbamate (301 mg, 1.078 mmol) was dissolved in DCM (40 ml). Hydrochloric acid (4M in dioxane, 5.4 ml) was added and the mixture was stirred at room temperature for 48 hours. The mixture was concentrated under reduced pressure, diethylether was added and the mixture was stirred at room temperature for 4 days. The solids were collected by filtration, rinsed with diethylether and dried under reduced pressure to yield 199 mg (0.789 mmol, 73%) MS(ESI) m/z=180.2 [M+1]⁺.

Step C: (E)-4,4,4-Trifluoro-N-methyl-N-[2-[methyl-(5-methyl-3-pyridyl)amino]ethyl]-but-2-enamide (E)-4,4,4-Trifluorobut-2-enoic acid (25 mg, 0.18 mmol) was dissolved in dichloromethane (1 ml containing one drop of dimethyl formamide), oxalyl chloride was added (16 µl, 0.18 mmol) and the solution was stirred at room temperature for 10 minutes. This solution was added to a solution of N,N'-dimethyl-N-(5-methyl-3-pyridyl)ethane-1,2-diamine dihydrochloride (36 mg, 0.13 mmol) and EDIPA (132 µl, 0.75 mmol) in anhydrous dichloromethane (1.5 ml) and the resulting mixture was stirred at room temperature for two hours. The reaction mixture was concentrated under reduced pressure and the resulting residue was purified by preparative HPLC (Waters XBridge, gradient of water containing 0.1% NH₃ and 10% to 100% acetonitrile) to yield 24 mg of a solid (0.08 mmol, 53%).

Example 15

Synthesis of ethyl 5-methylamino-2-[2-[[(E)-4,4,4-trifluorobut-2-enoyl]amino]ethylamino]-thiazole-4-carboxylate (C-24)

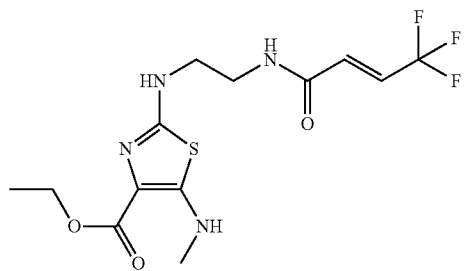 [SMILES: CCOC(=O)c1nc(NCCNC(=O)/C=C/C(F)(F)F)sc1NC]

Step A: Ethyl 2-[2-(tert-butoxycarbonylamino)ethylamino]-5-methylamino-thiazole-4-carboxylate Ethyl 2-bromo-5-methylamino-thiazole-4-carboxylate (546 mg, 2.059 mmol) and tert-butyl N-(2-aminoethyl)carbamate (1.3 g, 8.11 mmol) were combined in anhydrous 1,4-dioxane (15 ml). EDIPA (3 ml, 17.2 mmol) was added and the mixture was heated in a sealed tube for 23 hours at 100° C. The mixture was cooled to room temperature and partitioned between DCM and a saturated solution of sodium bicarbonate. Layers were separated, the aqueous phase was extracted twice with DCM and the combined organic layers were dried over sodium sulfate. The solvent was removed under reduced pressure and the residue was purified by column chromatography (silica, gradient of 30 to 100% ethyl acetate in heptane) to yield 185 mg (0.537 mmol, 26%) MS(ESI) m/z=345.2 [M+1]⁺.

Step B: Ethyl 2-(2-aminoethylamino)-5-methylamino-thiazole-4-carboxylate dihydrochloride To a solution of ethyl 2-[2-(tert-butoxycarbonylamino)ethylamino]-5-methylamino-thiazole-4-carboxylate (184 mg, 0.534 mmol) in a mixture of diethyletehr (15 ml) and anhydrous ethanol (15 ml) was added hydrochloric acid (4N in dioxane, 5 ml, 20 mmol) and the mixture was stirred at room temperature for two days. The solids were collected by filtration, washed with diethylether and dried under reduced pressure to yield 145 mg (0.457 mmol, 86%). MS(ESI) m/z=245.1 [M+1]⁺.

Step C: Ethyl 2-[2-(tert-butoxycarbonylamino)ethylamino]-5-methylamino-thiazole-4-carboxylate (E)-4,4,4-Trifluorobut-2-enoic acid (25 mg, 0.18 mmol) was dissolved in dichloromethane (1 ml containing one drop of dimethyl formamide), oxalyl chloride was added (16 µl, 0.18 mmol) and the solution was stirred at room temperature for 10 minutes. This solution was added to a solution of ethyl 2-(2-aminoethylamino)-5-methylamino-thiazole-4-carboxylate dihydrochloride (48 mg, 0.15 mmol) and EDIPA (132 µl, 0.75 mmol) in anhydrous dichloromethane (1.5 ml) and the resulting mixture was stirred at room temperature overnight. The reaction mixture was concentrated under reduced pressure and the resulting residue was purified by preparative HPLC (Waters XBridge, gradient of water containing 0.1% NH₃ and 10% to 100% acetonitrile) to yield 30 mg of a solid (0.071 mmol, 47%).

Example 16

Synthesis of (E)-N-[2-[(5-cyclopropyl-1,2,4-oxadiazol-3-yl)amino]ethyl]-4,4,4-trifluoro-but-2-enamide (C-36)

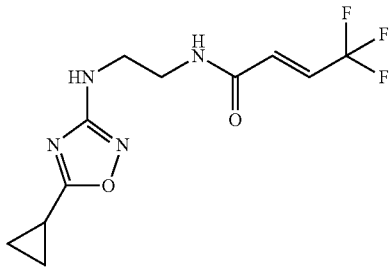 [SMILES: O=C(/C=C/C(F)(F)F)NCCNc1noc(C2CC2)n1]

Step A: N-(5-Cyclopropyl-1,2,4-oxadiazol-3-yl)ethane-1,2-diamine

3-Chloro-5-cyclopropyl-1,2,4-oxadiazol (72 mg, 0.5 mmol) and TEA (139 µl, 1 mmol) were dissolved in ethane-1,2-diamine (3 ml), placed in a sealed tube and heated at 125° C. for 2 hours. The mixture was cooled to room temperature and evaporated to dryness under reduced pressure and used directly in the next step MS(ESI) m/z=169.1 [M+1]+.

Step B: (E)-N-[2-[(5-Cyclopropyl-1,2,4-oxadiazol-3-yl)amino]ethyl]-4,4,4-trifluoro-but-2-enamide (E)-4,4,4-Trifluorobut-2-enoic acid (17 mg, 0.12 mmol) was dissolved in dichloromethane (1 ml containing one drop of dimethyl formamide), oxalyl chloride was added (11 μl, 0.12 mmol) and the solution was stirred at room temperature for 10 minutes. This solution was added to a solution of N-(5-cyclopropyl-1,2,4-oxadiazol-3-yl)ethane-1,2-diamine (17 mg, 0.1 mmol) and TEA (42 μl, 0.3 mmol) in a mixture of anhydrous dichloromethane (1 ml) and anhydrous DMF (1 ml) and the resulting mixture was stirred at room temperature. After one hour, additional acid chloride (0.12 mmol as prepared above) was added and stirring was continued for one hour. The reaction mixture was diluted with ethyl acetate, washed with saturated sodium bicarbonate solution and brine, dried (magnesium sulfate), concentrated under reduced pressure and the resulting residue was purified by preparative HPLC (Waters XBridge, gradient of water containing 0.1% NH₃ and 5% to 100% acetonitrile) to yield 8 mg of a solid (0.019 mmol, 19%).

Example 17

Synthesis of (E)-4,4,4-trifluoro-N-[2-[(4-methyl-1-oxo-2-pyridyl)amino]ethyl]but-2-enamide (D-2)

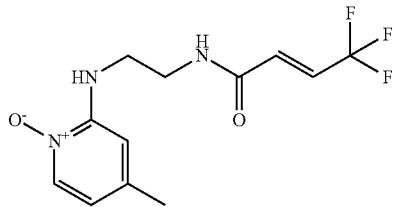 [SMILES: Cc1cc[n+]([O-])c(NCCNC(=O)/C=C/C(F)(F)F)c1]

Step A: tert-Butyl N-[2-[(4-methyl-1-oxo-2-pyridyl)amino]ethyl]carbamate

2-Chloro-4-methyl-pyridine 1-oxide (750 mg, 5.22 mmol, see example 12) was combined with tert-butyl N-(2-aminoethyl)carbamate (4.2 g, 26 mmol) in t-amylalcohol (30 ml). Sodium bicarbonate (2.19 g, 26.1 mmol) was added and the mixture was heated under reflux overnight. The mixture was concentrated under reduced pressure and the residue was partitioned between ethyl acetate and water. Layers were separated, the aqueous layer was extracted once with ethyl acetate and the combined organic phases were washed with brine, dried over sodium sulfate and concentrated under reduced pressure. The residue was purified by column chromatography (silica, gradient of 3 to 7% methanol in DCM) to yield 500 mg (1.87 mmol, 35.8%) MS(ESI) m/z=268.2 [M+1]+.

Step B: N-(4-Methyl-1-oxo-2-pyridyl)ethane-1,2-diamine hydrochloride tert-Butyl N-[2-[(4-methyl-1-oxo-2-pyridyl)amino]ethyl]carbamate (0.8 g, 2.99 mmol) was dissolved in a mixture of dioxane (10 ml), DCM (5 ml) and methanol (2 ml). Hydrochloric acid (4N in dioxane, 7.5 ml) was added slowly and the mixture was stirred at room temperature for 3 hours. Diethyl ether (20 ml) was added, the precipitate was filtered off, washed with diethyl ether and dried under reduced pressure to give 693 mg of an off-white solid (quantitative) MS(ESI) m/z=168.1 [M+1]+.

Step C: (E)-4,4,4-Trifluoro-N-[2-[(4-methyl-1-oxo-2-pyridyl)amino]ethyl]but-2-enamide N-(4-Methyl-1-oxo-2-pyridyl)ethane-1,2-diamine hydrochloride (150 mg, 0.736 mmol) was dissolved in DCM (6 ml), (E)-4,4,4-trifluorobut-2-enoic acid (103 mg, 0.736 mmol) was added followed by EDIPA (386 μl, 2.2 mmol), HOBt (30.1 mg, 0.221 mmol) and EDC (141 mg, 0.736 mmol) and the mixture was stirred at room temperature for 36 hours. The mixture was concentrated under reduced pressure and the residue was partitioned between ethyl acetate and water. Layers were separated, the aqueous layer was extracted once with ethyl acetate and the combined organic phases were washed with brine, dried over sodium sulfate and concentrated under reduced pressure. The residue was purified by column chromatography (silica, gradient of 2 to 7% methanol in DCM) to yield 53 mg (0.183 mmol, 25%).

Example 18

Synthesis of (E)-N-[2-[(5-dimethylamino-1-methyl-1,2,4-triazol-3-yl)amino]ethyl]-4,4,4-trifluoro-but-2-enamide (C-41)

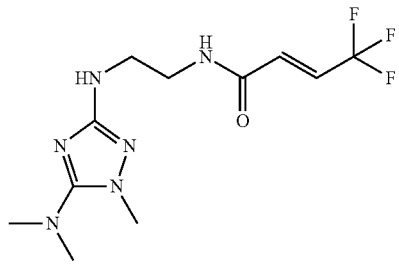 [SMILES: CN(C)c1nc(NCCNC(=O)/C=C/C(F)(F)F)nn1C]

Step A: N3-(2-aminoethyl)-N5,N5,1-trimethyl-1,2,4-triazole-3,5-diamine

5-Bromo-N,N,2-trimethyl-1,2,4-triazol-3-amine (103 mg, 0.5 mmol) and copper (I) iodide (4.8 mg, 0.025 mmol) were placed in a sealed microwave vial and flushed with argon. Then ethane-1,2-diamine (1.5 ml, 22 mmol) and triethylamine (140 μL, 1 mmol) were added via siringe. The reaction mixture was heated in a microwave oven at 80° C. for 1 h. The reaction mixture was diluted with ethyl acetate, filtered through kieselguhr and the filtrate was concentrated under reduced pressure to give 97 mg (quantitative) MS(ESI) m/z=185.1 [M+1]+.

Step B: (E)-N-[2-[(5-Dimethylamino-1-methyl-1,2,4-triazol-3-yl)amino]ethyl]-4,4,4-trifluoro-but-2-enamide (E)-4,4,4-Trifluorobut-2-enoic acid (14 mg, 0.1 mmol) was dissolved in dichloromethane (1 ml containing one drop of dimethyl formamide), oxalyl chloride was added (9 μl, 0.1 mmol) and the solution was stirred at room temperature for 5 minutes. This solution was added to a solution of N3-(2-aminoethyl)-N5,N5,1-trimethyl-1,2,4-triazole-3,5-diamine (18 mg, 0.1 mmol) and TEA (42 µl, 0.3 mmol) in a mixture of anhydrous dichloromethane (1 ml) and anhydrous DMF (1 ml) and the resulting mixture was stirred at room temperature. After one hour, the reaction mixture was diluted with ethyl acetate, washed with saturated sodium bicarbonate solution and brine, dried (magnesium sulfate), concentrated under reduced pressure and the resulting residue was purified by preparative HPLC (Waters XBridge, gradient of water containing 0.1% NH$_3$ and 5% to 100% acetonitrile) to yield 8 mg of a solid (0.026 mmol, 26%).

Example 19

Synthesis of (E)-4,4-difluoro-N-[2-[(4-methoxy-6-methyl-2-pyridyl)amino]ethyl]pent-2-enamide (A-157)

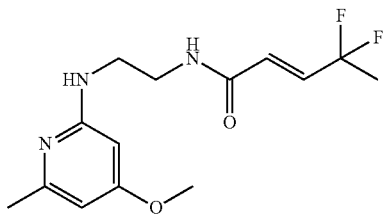 [SMILES: COc1cc(C)nc(NCCNC(=O)/C=C/C(C)(F)F)c1]

Step A: 2-Bromo-6-methyl-pyridine 1-oxide

2-Bromo-6-methylpyridine (36 g, 0.2 mol) was dissolved in acetic acid (700 ml), hydrogen peroxide (30%, 62 ml, 0.6 mol) was added and the mixture was stirred at 90° C. for 24 hours. After cooling to room temperature, the mixture was diluted with water (700 ml) and extracted with DCM (4×). The combined organic phases were washed with water, dried (sodium sulfate) and concentrated under reduced pressure to give 36 g of a red-brown liquid (0.19 mol, 94%) MS(APCI) m/z=188.0 [M+1]$^+$.

Step B: 2-Bromo-6-methyl-4-nitro-pyridine 1-oxide

To cooled nitric acid (concentrated, 168 ml) was added sulfuric acid (concentrated, 300 ml) under cooling followed by 2-bromo-6-methyl-pyridine 1-oxide (35 g, 0.186 mol). The mixture was stirred at 70° C. for 4 hours, cooled to room temperature and poored slowly on crushed ice. A stream of nitrogen was bubbled through the mixture overnight. The mixture was basified to pH 8 under cooling with NaOH (10N, ca. 1 L), diluted with water (3 L) and extracted with DCM (5×). The combined organic phases were dried (sodium sulfate) and evaporated to dryness to yield 27.6 g of a yellow crystaline solid (0.118 mol, 57%).

Step C: 2-Bromo-6-methyl-4-methoxy-pyridine 1-oxide

2-Bromo-6-methyl-4-nitro-pyridine 1-oxide (4 g, 17 mmol) was dissolved in methanol (anhydrous, 100 ml), and sodium methoxide (1.8 g, 33 mmol) was added. The mixture was stirred at room temperature for 90 minutes, diluted with water (90 ml) and concentrated under reduced pressure to half of its volume. The mixture was extracted with DCM (5×), the combined organic phases were dried (sodium sulfate) and concentrated to dryness under reduced pressure to yield 3.3 g of yellow crystals, 15 mmol, 88%) MS(APCI) m/z=217.9 [M+1]$^+$.

Step D: 2-Bromo-6-methyl-4-methoxy-pyridine

2-Bromo-6-methyl-4-methoxy-pyridine 1-oxide (3.3 g, 15 mmol) was dissolved in ethyl acetate (anhydrous, 100 ml), phosphorus trichloride (6.6 ml) was added dropwise and the mixture was stirred at room temperature for three hours. The precipitate was collected by filtration, washed with ethyl acetate and dried to yield 2.4 g of beige crystals (12 mmol, 79%) MS(APCI) m/z=203.9 [M+1]$^+$.

Step E: N-(4-Methoxy-6-methyl-2-pyridyl)ethane-1,2-diamine

2-Bromo-6-methyl-4-methoxy-pyridine (202 mg, 1 mmol) was combined with 1,2-ethylenediamine (3 ml) and triethylamin (280 µl, 2 mmol) and heated in a sealed tube at 120° C. for three hours under microwave heating. The mixture was diluted with ethyl acetate, filtered through kieselguhr and evaporated under reduced pressure. The residue was purified by preparative HPLC (Waters XBridge, gradient of water containing 0.1% NH$_3$ and 2% to 100% acetonitrile) to yield 44 mg of a solid (0.24 mmol, 24%) MS(ESI) m/z=182.1 [M+1]$^+$.

Step F: (E)-4,4-Difluoro-N-[2-[(4-methoxy-6-methyl-2-pyridyl)amino]ethyl]pent-2-enamide (E)-4,4-Drifluoropent-2-enoic acid (17 mg, 0.12 mmol) was dissolved in dichloromethane (1 ml containing one drop of dimethyl formamide), oxalyl chloride was added (11 µl, 0.12 mmol) and the solution was stirred at room temperature for 10 minutes. This solution was added to a solution of N-(4-methoxy-6-methyl-2-pyridyl)ethane-1,2-diamine (18 mg, 0.1 mmol) and TEA (42 µl, 0.3 mmol) in a mixture of anhydrous dichloromethane (1 ml) and anhydrous DMF (0.5 ml) and the resulting mixture was stirred at room temperature. After one hour, the reaction mixture was diluted with ethyl acetate, washed with saturated sodium bicarbonate solution (2×) and brine, dried (magnesium sulfate), concentrated under reduced pressure and the resulting residue was purified by preparative HPLC (Waters XBridge, gradient of water containing 0.1% NH$_3$ and 5% to 100% acetonitrile) to yield 13 mg of a solid (0.043 mmol, 43%).

C. Analytics: HPLC Methods

Method 1

HPLC-MS System:

Agilent LC/MSD Trap 1100 series composed of:

Binary pump G1312A included degasser G1379A, well plate sampler G1367A, column oven G1316A, diode array detector G1315B, and mass detector G2445D with APCI-source.

Chromatographic System:

Column: Waters Xbridge C-18, 4.6*50 mm., 2.5µ

Oven: 40° C.

Injection: 2.0 µl

Eluents:

Solvent A: water/ammonia: 99.9/0.1 vol./vol.

Solvent B: acetonitrile/ammonia: 99.9/0.1 vol./vol.

Flow: 1.0 ml/min

Gradient:

| Time [min] | Solvent A [%] | Solvent B [%] |
|---|---|---|
| 0.0 | 90 | 10 |
| 4 | 0 | 100 |
| 5 | 0 | 100 |

Run time: 7 min (equilibration included)
Detection methods:
UV at 254 nm, 210 nm
APCI/MS (80-1000 m/z), positive ions
Comment: Samples diluted in a 1 to 1 mixture of solvents A and B prior to analysis Method 2
HPLC-MS System:
Agilent LC 1290 Infinity series composed of:
Binary pump G4220A, well plate sampler G4226, thermostat G1330B, diode array detector G4212A, column thermostat G1316C, and single quadrupole mass detector 6130 with multimode ion source.
Chromatographic System:
Column: Waters Xbridge BEH C18, 2.1*50 mm., 2.5µ
Oven: 40° C.
Injection: 0.5 µl
Eluents:
Solvent A: water/ammonia: 99.9/0.1 vol./vol.
Solvent B: acetonitrile/ammonia: 99.9/0.1 vol./vol.
Flow: 0.8 ml/min
Gradient:

| Time [min] | Solvent A [%] | Solvent B [%] |
|---|---|---|
| 0.0 | 98 | 2 |
| 1.2 | 0 | 100 |
| 1.5 | 0 | 100 |

Run time: 2 min (equilibration included)
Detection methods:
UV at 254 nm, 210 nm
APCI/ES/MS (100-1000 m/z), positive ions
Comment: Samples diluted in a 1 to 1 mixture of solvents A and B prior to analysis Method 3
HPLC-MS System:
Agilent LC 1290 Infinity series composed of:
Binary pump G4220A, well plate sampler G4226, thermostat G1330B, diode array detector G4212A, column thermostat G1316C, and single quadrupole mass detector 6130 with multimode ion source.
Chromatographic System:
Column: Merck Chromolith fast gradient RP18e, 2.0*50 mm
Oven: 40° C.
Injection: 0.5 µl
Eluents:
Solvent A: water/formic acid: 99.9/0.1 vol./vol.
Solvent B: acetonitrile/formic acid: 99.9/0.1 vol./vol.
Flow: 0.8 ml/min
Gradient:

| Time [min] | Solvent A [%] | Solvent B [%] |
|---|---|---|
| 0.0 | 98 | 2 |
| 1.2 | 0 | 100 |
| 1.5 | 0 | 100 |

Run time: 2 min (equilibration included)
Detection methods:
UV at 254 nm, 210 nm
APCI/ES/MS (100-1000 m/z), positive and negative ions
Comment: Samples diluted in a 1 to 1 mixture of solvents A and B prior to analysis D. Specific Compounds Table A below provides for each of the exemplified compounds of the formula (A) the structure, the calculated molecular weight (MW) (gram/mol), the observed MS signal (m/z), the HPLC retention time (Rt) in minutes and the number of the HPLC-method as described in paragraphe C above ("Analytics: HPLC-Methods") used for analysis. From compound A-205 until the end of Table A the methods by which the compounds are synthesized are identified by referring to the synthetic steps described in the synthesis examples of paragraph B above ("Synthesis Examples").

TABLE A

Formula (A)

(Y³ = C)

| No. | R¹ | R² | R³ | X | n | D | Y¹ | Y² | Y⁴ | Y⁵ | R⁹ᵃ | R⁹ᵇ | R¹⁰ | R⁹ᶜ | R⁹ᵈ | HPLC | Rt | m/z | MW |
|---|---|---|---|---|---|---|---|---|---|---|---|---|---|---|---|---|---|---|---|
| A-1 | CF₃ | H | H | CO | 2 | N | C | N | C | C | H | — | H | H | H | 1 | 2.89 | 260.1 | 259.2 |
| A-2 | CF₃ | H | H | CO | 2 | N | N | C | C | C | — | H | H | CH₃ | H | 1 | 3.34 | 274.1 | 273.3 |
| A-3 | CHF₂ | H | H | CO | 2 | N | N | C | C | C | — | H | H | CH₃ | H | 1 | 3.00 | 256.1 | 255.3 |
| A-4 | CF₂CHF₂ | H | H | CO | 2 | N | N | C | C | C | — | H | H | CH₃ | H | 1 | 3.36 | 306.2 | 305.3 |
| A-5 | CF₂CF₃ | H | H | CO | 2 | N | N | C | C | C | — | H | H | CH₃ | H | 1 | 3.67 | 324.2 | 323.3 |
| A-6 | CF₂CH₃ | H | H | CO | 2 | N | N | C | C | C | — | H | H | CH₃ | H | 1 | 3.19 | 270.1 | 269.3 |
| A-7 | CF₂CHF₂ | H | H | CO | 2 | N | C | C | C | C | H | H | H | H | H | 1 | 2.93 | 292.1 | 291.2 |
| A-8 | CF₂CF₃ | H | H | CO | 2 | N | C | C | C | C | H | H | H | H | H | 1 | 3.26 | 310.1 | 309.2 |
| A-9 | CF₂CH₃ | H | H | CO | 2 | N | C | N | C | C | H | — | H | H | H | 1 | 2.73 | 256.1 | 255.3 |
| A-10 | CHF₂ | H | H | CO | 2 | N | C | N | C | C | H | — | H | H | H | 1 | 2.49 | 242.1 | 241.2 |
| A-11 | CF₃ | H | H | CO | 2 | N | N | C | C | C | — | CH₃ | H | CH₃ | H | 1 | 3.41 | 274.1 | 273.3 |
| A-12 | CF₃ | H | H | CO | 3 | N | N | C | C | C | — | H | H | OCH₂CH₃ | H | 1 | 3.39 | 288.2 | 287.3 |
| A-13 | CF₃ | H | H | CO | 3 | N | N | C | C | C | — | H | H | OCH₂CH₃ | H | 1 | 3.48 | 318.2 | 317.3 |
| A-14 | CF₃ | H | H | CO | 3 | N | N | C | C | C | — | H | H | OCH₂CH₃ | H | 1 | 3.42 | 304.2 | 303.3 |
| A-15 | CF₂CH₃ | H | H | CO | 3 | N | N | C | C | C | — | H | H | OCH₂CH₃ | H | 1 | 3.35 | 314.2 | 313.3 |
| A-16 | CF₂CH₃ | H | H | CO | 2 | N | C | C | N | C | — | H | H | H | H | 1 | 3.29 | 300.2 | 299.3 |
| A-17 | CF₂CH₃ | H | H | CO | 2 | N | N | C | C | C | — | H | H | H | H | 1 | 3.27 | 270.1 | 269.3 |
| A-18 | CF₃ | H | H | CO | 3 | N | N | C | C | C | — | H | H | CH₃ | H | 1 | 3.27 | 284.2 | 283.3 |
| A-19 | CF₃ | H | H | CO | 2 | N | C | N | C | C | H | H | H | H | H | 1 | 3.29 | 290.1 | 289.3 |
| A-20 | CF₃ | H | H | CO | 2 | N | C | C | C | C | CH₃ | H | OCH₃ | H | OCH₃ | 1 | 3.22 | 304.2 | 303.3 |
| A-21 | CF₃ | H | H | CO | 2 | N | C | N | C | C | CH₃ | — | CH₃ | H | H | 1 | 2.97 | 274.1 | 273.3 |
| A-22 | CF₃ | H | H | CO | 2 | N | N | C | C | C | OCH₃ | CH₃ | H | H | H | 1 | 3.13 | 288.2 | 287.3 |
| A-23 | CF₃ | H | H | CO | 3 | N | C | N | C | C | — | H | CH₃ | H | H | 1 | 3.60 | 288.2 | 287.3 |
| A-24 | CF₃ | H | H | CO | 2 | N | C | C | N | C | OCH₃ | — | H | H | H | 1 | 3.33 | 290.1 | 289.3 |
| A-25 | CF₂CH₃ | H | H | CO | 2 | N | N | C | C | C | — | H | OCH₃ | H | OCH₃ | 1 | 3.15 | 286.2 | 285.3 |
| A-26 | CF₂CH₃ | H | H | CO | 3 | N | N | C | C | C | — | H | CH₃ | H | H | 1 | 3.09 | 300.2 | 299.3 |
| A-27 | CF₂CH₃ | H | H | CO | 2 | N | C | N | C | C | OCH₃ | — | CH₃ | H | H | 1 | 3.54 | 300.2 | 299.3 |
| A-28 | CF₂CH₃ | H | H | CO | 2 | N | C | N | C | C | H | — | CH₃ | H | H | 1 | 2.87 | 270.2 | 269.3 |

TABLE A-continued

Formula (A)

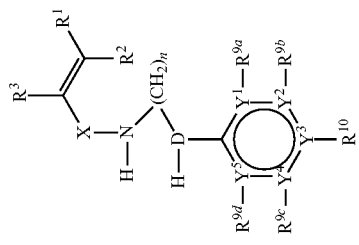

| | | | | | | | | | | | | | | | | | |
|---|---|---|---|---|---|---|---|---|---|---|---|---|---|---|---|---|---|
| A-29 | CF₂CH₃ | H | CO | 2 | N | C | C | CH₃ | | | H | H | 1 | 2.85 | 270.2 | 269.3 |
| A-30 | CF₂CH₃ | H | CO | 2 | N | C | C | CH₃ | | CH₃ | H | 1 | 2.99 | 284.2 | 283.3 |
| A-31 | CF₂CH₃ | H | CO | 2 | N | C | C | OCH₃ | | — | CH₃ | 1 | 3.47 | 284.2 | 285.3 |
| A-32 | CF₂CH₃ | H | CO | 2 | N | C | C | H | | CH₃ | H | 1 | 3.18 | 286.2 | 285.3 |
| A-33 | CF₃ | H | CO | 2 | N | N | C | — | | H | H | 1 | 2.70 | 261.3 | 260.2 |
| A-34 | CF₃ | H | CO | 2 | N | C | C | — | | OCH₂CH₃ | H | 1 | 3.36 | 304.2 | 303.3 |
| A-35 | CF₂CH₃ | H | CO | 2 | N | C | N | — | | OCH₂CH₃ | H | 1 | 3.06 | 286.2 | 285.3 |
| A-36 | CF₂CH₃ | H | CO | 2 | C | C | N | H | | OCH₃ | H | 1 | 3.03 | 286.2 | 285.3 |
| A-37 | CF₃ | H | CO | 2 | N | N | C | — | | OCH₃ | H | 1 | 3.26 | 300.2 | 299.3 |
| A-38 | CF₃ | H | CO | 2 | N | N | C | — | | OCH₃ | H | 1 | 2.79 | 290.2 | 289.3 |
| A-39 | CF₃ | H | CO | 2 | N | C | C | CH₃ | | OCH₃ | H | 1 | 3.34 | 304.2 | 303.3 |
| A-40 | CF₃ | H | CO | 2 | N | C | C | CH₃ | | H | H | 1 | 3.21 | 290.2 | 289.3 |
| A-41 | CF₃ | H | CO | 2 | N | C | C | H | Y²—CH=CH—CH=CH—Y³ | OCH₃ | H | 1 | 3.71 | 310.2 | 309.3 |
| A-42 | CF₃ | H | CO | 2 | N | N | C | — | Y³—CH=CH—CH=CH—Y⁴ | H | 1 | 3.74 | 310.2 | 309.3 |
| A-43 | CF₃ | H | CO | 2 | N | C | C | — | Y⁴—CH=CH—CH=CH—Y⁵ | H | 1 | 3.69 | 310.2 | 309.3 |
| A-44 | CF₂CH₃ | H | CO | 2 | N | C | C | CH₃ | | CH₃ | CH₃ | 1 | 3.08 | 284.2 | 283.3 |
| A-45 | CF₃ | H | CO | 2 | N | C | C | CH₃ | CH₃ | H | — | 2 | 0.81 | 275.0 | 274.2 |
| A-46 | CF₃ | H | CO | 2 | N | N | C | — | OCH₃ | H | — | 2 | 0.80 | 291.0 | 290.2 |
| A-47 | CF₃ | H | CO | 2 | N | C | C | — | CH₃ | CH₃ | H | 2 | 0.87 | 289.0 | 288.3 |
| A-48 | Cl | H | CO | 2 | N | C | C | H | H | H | H | 2 | 0.81 | 240.1 | 239.7 |
| A-49 | H | Cl | CO | 2 | N | C | C | — | H | H | H | 2 | 0.75 | 240.0 | 239.7 |
| A-50 | OCH₂CH₃ | H | CO | 2 | N | C | C | — | H | H | H | 2 | 0.80 | 250.1 | 249.3 |
| A-51 | SCH₃ | H | CO | 2 | N | N | C | — | — | H | H | 2 | 0.80 | 252.1 | 251.4 |
| A-52 | (E)-CH═CHCH₃ | H | CO | 2 | N | N | C | — | — | H | H | 2 | 0.87 | 246.1 | 245.3 |
| A-53 | H | H | CO | 2 | N | C | C | — | H | CH₃ | H | 2 | 0.73 | 248.1 | 247.3 |
| A-54 | COCH₃ | H | CO | 2 | N | C | C | — | CH₃ | CH₃ | H | 2 | 0.83 | 278.0 | 277.3 |
| A-55 | CO₂C₂H₅ | H | CO | 2 | N | C | C | — | OCH₃ | CH₃ | H | 2 | 0.97 | 262.1 | 261.4 |
| A-56 | CH(CH₃)₂ | CH₃ | CO | 2 | N | C | C | — | CH₃ | CH₃ | H | 2 | 0.83 | 246.1 | 245.3 |
| A-57 | cyclopropyl | H | CO | 2 | N | C | C | — | H | CH₃ | H | 2 | 0.84 | 258.1 | 257.3 |
| A-58 | (CH₂)₂CCH | H | CO | 2 | N | C | C | — | H | CH₃ | H | 2 | 0.86 | 280.0 | 279.4 |
| A-59 | (CH₂)₂SCH₃ | H | CO | 2 | N | C | C | — | H | CH₃ | H | 2 | 0.95 | 288.0 | 287.3 |
| A-60 | CF₃ | CH₃ | CO | 2 | N | C | C | — | H | CH₃ | H | 2 | 0.96 | 332.0 | 331.3 |
| A-61 | SF₅ | H | CO | 2 | N | C | C | — | H | CH₃ | H | 2 | 0.93 | 290.7 | 289.7 |
| A-62 | CF₂Cl | H | CO | 2 | N | C | C | — | H | CH₃ | H | 2 | 0.90 | 288.0 | 287.4 |
| | thiophen-2-yl | | | | | | | | | | | | | | |

TABLE A-continued

Formula (A):

| No. | R³ | R² | X | n | Y¹ | Y² | Y³ | Y⁵ | R⁹ᵈ | R⁹ᵃ | R⁹ᵇ | R⁹ᶜ | R¹⁰ | col | RT | M+H | MW |
|---|---|---|---|---|---|---|---|---|---|---|---|---|---|---|---|---|---|
| A-63 | imidazol-4-yl | H | CO | 2 | N | N | C | C | — | H | H | CH₃ | H | 2 | 0.67 | 272.1 | 271.3 |
| A-64 | furan-2-yl | H | CO | 2 | N | N | C | C | — | H | H | CH₃ | H | 2 | 0.86 | 272.0 | 271.3 |
| A-65 | H | CH₃ | CO | 2 | N | N | C | C | — | H | H | CH₃ | H | 2 | 0.71 | 206.1 | 205.3 |
| A-66 | CH₃ | H | CO | 2 | N | N | C | C | — | H | H | CH₃ | H | 2 | 0.83 | 234.1 | 233.3 |
| A-67 | phenyl | H | CO | 2 | N | N | C | C | — | H | H | OCH₂CH₃ | H | 2 | 0.92 | 282.0 | 281.4 |
| A-68 | CF₂CHF₂ | H | CO | 2 | N | N | C | C | — | H | H | OCH₂CH₃ | H | 2 | 0.93 | 336.1 | 335.3 |
| A-69 | CF₂CF₃ | H | CO | 2 | N | N | C | C | — | H | H | OCH₂CH₃ | H | 2 | 1.00 | 354.1 | 353.3 |
| A-70 | CHF₂ | H | CO | 2 | N | N | C | C | — | H | H | OCH₂CH₃ | H | 2 | 0.84 | 286.1 | 285.3 |
| A-71 | CF₂Cl | H | CO | 2 | N | N | C | C | — | H | H | H | H | 2 | 0.95 | 320.0 | 319.7 |
| A-72 | CF₂CHF₂ | H | CO | 2 | N | C | C | C | CH₃ | CH₃ | H | H | H | 2 | 0.82 | 306.1 | 305.3 |
| A-73 | CF₂CF₃ | H | CO | 2 | C | C | C | C | CH₃ | H | H | H | H | 2 | 0.91 | 324.0 | 323.3 |
| A-74 | CHF₂ | H | CO | 2 | C | C | C | C | CH₃ | H | H | H | H | 2 | 0.72 | 256.0 | 255.3 |
| A-75 | CF₂Cl | H | CO | 2 | C | C | C | C | CH₃ | H | H | CH₃ | H | 2 | 0.85 | 290.0 | 289.7 |
| A-76 | CF₂CHF₂ | H | CO | 2 | N | N | C | C | — | CH₃ | H | CH₃ | H | 2 | 0.97 | 320.1 | 319.3 |
| A-77 | CF₂CF₃ | H | CO | 2 | N | N | C | C | — | CH₃ | H | CH₃ | H | 2 | 1.06 | 338.1 | 337.3 |
| A-78 | CHF₂ | H | CO | 2 | N | N | C | C | — | CH₃ | H | CH₃ | H | 2 | 0.89 | 270.1 | 269.3 |
| A-79 | CF₂Cl | H | CO | 2 | N | N | C | C | — | CH₃ | H | CH₃ | H | 2 | 1.01 | 304.0 | 303.7 |
| A-80 | CF₃ | H | CO | 2 | N | N | C | C | — | H | CH₃ | — | H | 2 | 0.80 | 275.1 | 274.2 |
| A-81 | CF₃ | H | CO | 2 | N | C | N | C | — | H | H | — | H | 2 | 0.78 | 275.1 | 274.2 |
| A-82 | CF₂CHF₂ | H | CO | 2 | N | N | C | C | — | H | H | OCH₃ | H | 2 | 0.87 | 322.1 | 321.3 |
| A-83 | CF₂CF₃ | H | CO | 2 | N | N | C | C | — | H | CH₃ | OCH₃ | H | 2 | 0.95 | 340.0 | 339.3 |
| A-84 | CHF₂ | H | CO | 2 | N | N | C | C | — | H | H | OCH₃ | H | 2 | 0.78 | 272.1 | 271.3 |
| A-85 | CF₂Cl | H | CO | 2 | N | N | C | C | — | H | H | OCH₃ | H | 2 | 0.90 | 306.0 | 305.7 |
| A-86 | CF₃ | H | CO | 2 | N | N | C | C | CH₃ | H | H | H | H | 2 | 0.84 | 289.0 | 288.3 |
| A-87 | CF₂CHF₂ | H | CO | 2 | N | N | C | C | CH₃ | H | H | H | H | 2 | 0.93 | 306.1 | 305.3 |
| A-88 | CF₂CF₃ | H | CO | 2 | N | N | C | C | CH₃ | H | H | H | H | 2 | 1.01 | 324.1 | 323.3 |
| A-89 | CHF₂ | H | CO | 2 | N | N | C | C | CH₃ | H | H | H | H | 2 | 0.83 | 256.1 | 255.3 |
| A-90 | CF₂Cl | H | CO | 2 | N | N | C | C | CH₃ | H | H | H | H | 2 | 0.95 | 290.0 | 289.7 |
| A-91 | CF₃ | H | CO | 2 | N | C | C | C | CH(CH₃)₂ | H | H | H | H | 1 | 4.05 | 302.2 | 301.3 |
| A-92 | CF₃ | H | CO | 2 | N | C | C | C | OCH₃ | H | H | OCH₃ | H | 1 | 0.96 | 290.0 | 289.3 |
| A-93 | CF₃ | H | CO | 2 | N | C | C | N | CH₃ | H | H | CH₃ | OCH₃ | 1 | 3.68 | 304.2 | 303.3 |
| A-94 | CF₃ | H | CO | 2 | N | C | C | C | OCH₂CH₃ | H | H | OCH₃ | H | 1 | 3.80 | 304.2 | 303.3 |
| A-95 | CF₃ | H | CO | 2 | N | N | C | C | — | H | H | CH₃ | OCH₃ | 1 | 3.08 | 274.1 | 273.3 |
| A-96 | CF₃ | H | CO | 2 | N | C | N | C | H | H | CH₃ | H | H | 1 | 2.94 | 290.2 | 289.3 |
| A-97 | CF₃ | H | CO | 2 | N | N | C | C | — | H | CH₃ | H | H | 1 | 3.36 | 274.1 | 273.3 |

TABLE A-continued

Formula (A) structure: R³-C(X)=C(R²)(R¹) connected via X-NH-(CH₂)ₙ-D to aromatic ring with Y¹-Y⁵ positions bearing R⁹ᵃ-R⁹ᵈ and R¹⁰ substituents.

| No. | R³ | R² | R¹ | X | n | Y¹ | Y² | Y³ | R¹⁰ | R⁹ᵈ | R⁹ᶜ | R⁹ᵇ | R⁹ᵃ | n' | t | [M+1] | [M] |
|---|---|---|---|---|---|---|---|---|---|---|---|---|---|---|---|---|---|
| A-98 | CF₃ | H | H | CO | 2 | N | N | C | CH₃ | — | — | — | H | CH₃ | 1 | 3.02 | 288.2 | 287.3 |
| A-99 | CF₂CH₃ | H | H | CO | 2 | N | N | C | — | CH(CH₃)₂ | — | H | CH₃ | H | 1 | 3.50 | 284.2 | 283.3 |
| A-100 | CF₂CH₃ | H | H | CO | 2 | N | N | C | — | OCH₃ | — | H | H | H | 1 | 3.91 | 298.2 | 297.3 |
| A-101 | CF₂CH₃ | H | H | CO | 2 | N | N | C | — | OCH₃ | — | H | OCH₃ | H | 1 | 3.42 | 286.2 | 285.3 |
| A-102 | CF₂CH₃ | H | H | CO | 2 | N | N | C | — | OCH₂CH₃ | — | H | H | H | 1 | 3.54 | 300.2 | 299.3 |
| A-103 | CF₂CH₃ | H | H | CO | 2 | C | N | C | H | CH₃ | H | H | CH₃ | H | 1 | 3.66 | 300.2 | 299.3 |
| A-104 | CF₂CH₃ | H | H | CO | 2 | C | N | C | H | OCH₃ | H | H | OCH₃ | H | 1 | 2.96 | 270.2 | 269.3 |
| A-105 | CF₂CH₃ | H | H | CO | 2 | N | N | C | — | — | — | H | H | H | 1 | 2.84 | 286.2 | 285.3 |
| A-106 | CH(CH₃)₂ | H | H | CO | 2 | N | N | C | — | CH(CH₃)₂ | — | H | CH₃ | H | 1 | 3.24 | 270.2 | 269.3 |
| A-107 | CH(CH₃)₂ | H | H | CO | 2 | N | N | C | — | CH₃ | — | CH₃ | H | H | 1 | 3.62 | 262.2 | 261.4 |
| A-108 | CH(CH₃)₂ | H | H | CO | 2 | N | N | C | — | OCH₃ | — | CH₃ | H | H | 1 | 4.05 | 276.2 | 275.4 |
| A-109 | CH(CH₃)₂ | H | H | CO | 2 | N | N | C | — | CH(CH₃)₂ | — | H | OCH₃ | H | 1 | 3.54 | 264.2 | 263.3 |
| A-110 | CH(CH₃)₂ | H | H | CO | 2 | N | N | C | — | OCH₃ | — | H | CH₃ | H | 1 | 3.68 | 278.2 | 277.4 |
| A-111 | CH(CH₃)₂ | H | H | CO | 2 | C | N | C | H | CH₃ | H | H | CH₃ | H | 1 | 3.78 | 278.2 | 277.4 |
| A-112 | CH(CH₃)₂ | H | H | CO | 2 | C | N | C | H | OCH₃ | H | H | OCH₃ | H | 1 | 3.09 | 248.2 | 247.3 |
| A-113 | CH(CH₃)₂ | H | H | CS | 2 | N | N | C | — | CH₃ | — | H | H | H | 1 | 2.95 | 264.2 | 263.3 |
| A-114 | CH(CH₃)₂ | H | H | CO | 2 | C | N | C | H | OCH₂CH₃ | H | H | OCH₃ | H | 1 | 3.35 | 248.2 | 247.3 |
| A-115 | CH(CH₃)₂ | H | H | CO | 2 | N | N | C | — | — | — | CH₃ | H | H | 1 | 3.00 | 262.2 | 261.4 |
| A-116 | CF₃ | H | H | CO | 2 | N | N | C | — | H | — | CH₃ | CH₃ | H | 1 | 3.63 | 288.2 | 287.3 |
| A-117 | CF₃ | H | H | CO | 2 | N | N | C | — | CH₃ | — | CH₃ | H | H | 2 | 0.85 | 273.1 | 272.3 |
| A-118 | CF₃ | OCH₂CH₃ | H | CO | 2 | N | N | C | — | H | — | H | H | H | 2 | 0.98 | 318.2 | 317.3 |
| A-119 | CF₃ | H | H | SO₂ | 2 | N | N | C | — | H | — | H | H | H | 2 | 1.09 | 290.1 | 289.3 |
| A-120 | CF₃ | H | H | SO₂ | 2 | CH | N | C | H | H | H | H | H | H | 2 | 0.91 | 273.1 | 272.3 |
| A-121 | CH(CH₃)₂ | H | H | CO | 2 | N | N | C | — | H | — | CH₃ | H | H | 2 | 3.09 | 270.1 | 269.4 |
| A-122 | CF₃ | H | H | SO₂ | 2 | CH | N | C | H | H | H | CH₃ | H | H | 2 | 0.94 | 310.0 | 309.3 |
| A-123 | CF₃ | H | H | CO | 2 | N | N | C | — | CH₃ | — | H | OCH₂CH₃ | H | 2 | 0.87 | 304.1 | 303.3 |
| A-124 | CF₃ | H | H | SO₂ | 2 | N | N | C | — | H | — | CH₃ | OCH₂CH₃ | H | 2 | 1.06 | 318.1 | 317.3 |
| A-125 | CH(CH₃)₂ | H | H | SO₂ | 2 | N | N | C | — | CH₃ | — | H | H | H | 1 | 3.55 | 284.2 | 283.4 |
| A-126 | CF₃ | H | H | CO | 2 | N | N | C | — | H | — | CH₃ | OCH₂CH₃ | H | 2 | 0.78 | 296.0 | 295.3 |
| A-127 | CF₂Cl | H | H | CO | 2 | N | N | C | — | CH₃ | — | CH₃ | H | H | 1 | 1.03 | 314.1 | 313.3 |
| A-128 | CF₃ | H | H | CO | 2 | N | N | C | — | CH₃ | — | H | H | CH₃ | 1 | 3.79 | 304.2 | 303.7 |
| A-129 | CF₃ | H | H | CO | 2 | N | N | C | — | Br | — | H | H | CH₃ | 1 | 3.99 | 352.1 | 352.2 |
| A-130 | CF₂CH₃ | H | H | CO | 2 | N | N | C | — | OCH₂CH₃ | — | H | H | CH₃ | 3 | 0.94 | 318.1 | 317.3 |
| A-131 | CF₃ | H | H | CO | 2 | N | N | C | — | OCH₂CH₃ | — | H | H | CH₃ | 3 | 0.88 | 314.1 | 313.3 |
| A-132 | CF₂Cl | H | H | CO | 2 | N | N | C | — | OCH₂CH₃ | — | H | H | CH₃ | 3 | 1.02 | 334.0 | 333.8 |

TABLE A-continued

Formula (A)

| ID | R | R³ | X | n | | | | D | | | | | | | | | | val1 | val2 | val3 |
|---|---|---|---|---|---|---|---|---|---|---|---|---|---|---|---|---|---|---|---|---|
| A-133 | CF₃ | H | CO | 2 | N | N | C | C | — | OCH₃ | H | | | | CH₃ | H | 3 | 0.85 | 304.0 | 303.3 |
| A-134 | CF₂CH₃ | H | CO | 2 | N | N | C | C | — | OCH₃ | H | | | | CH₃ | H | 3 | 0.79 | 300.1 | 299.3 |
| A-135 | CF₂Cl | H | CO | 2 | N | N | C | C | — | OCH₃ | H | | | | CH₃ | H | 3 | 0.92 | 320.0 | 319.7 |
| A-136 | CH(CH₃)₂ | H | CO | 2 | N | N | C | C | — | — | CH₃ | | | | H | H | 2 | 0.74 | 249.2 | 248.3 |
| A-137 | CF₃ | H | CO | 2 | N | N | C | C | — | CH₂CH₃ | CH₃ | | | | H | H | 2 | 0.73 | 275.1 | 274.2 |
| A-138 | CF₃ | H | CO | 2 | N | N | C | C | — | (CH₂)₂CH₃ | H | | | | H | H | 2 | 1.01 | 288.1 | 287.3 |
| A-139 | CF₃ | H | CO | 2 | N | N | C | C | — | H | CN | | | | H | H | 2 | 1.07 | 302.1 | 301.3 |
| A-140 | CF₃ | H | CO | 2 | N | N | C | C | — | N-pyrrolidinyl | H | | | | CH₃ | H | 2 | 0.89 | 299.1 | 298.3 |
| A-141 | CF₃ | H | CO | 2 | N | N | C | C | — | H | SO₂CH₃ | | | | H | H | 2 | 1.10 | 329.1 | 328.3 |
| A-142 | CF₃ | H | CO | 2 | N | N | C | C | — | CH₃ | H | | | | H | H | 2 | 0.77 | 338.0 | 337.3 |
| A-143 | CF₃ | H | CO | 2 | N | N | C | C | — | H | H | | | | CH₃ | CN | 2 | 1.07 | 327.1 | 326.3 |
| A-144 | CF₃ | H | CO | 2 | N | N | C | C | — | H | H | | | | SCH(CH₃)₂ | H | 2 | 0.88 | 306.1 | 305.3 |
| A-145 | CF₃ | H | CO | 2 | N | N | C | C | — | H | NO₂ | | | | CH₃ | NO₂ | 2 | 1.02 | 302.1 | 301.3 |
| A-146 | CF₃ | H | CO | 2 | N | N | C | C | — | H | H | | | | CH₃ | H | 2 | 0.99 | 319.0 | 318.3 |
| A-147 | CF₃ | H | CO | 2 | N | C | C | C | — | H | SCH₃ | | | | H | H | 2 | 0.93 | 319.0 | 318.3 |
| A-148 | CF₃ | H | CO | 2 | N | N | C | C | — | Y²—CH₂—CH₂—CH₂—CH₂—Y³ | | | | | H | H | 2 | 0.95 | 306.0 | 305.3 |
| A-149 | CF₃ | H | CO | 2 | N | N | C | C | — | N-morpholinyl | H | | | | CH₃ | H | 2 | 1.05 | 314.1 | 313.3 |
| A-150 | CF₃ | H | CO | 2 | N | N | C | C | — | H | N-morpholinyl | | | | H | H | 1 | 0.95 | 345.1 | 344.3 |
| A-151 | CF₃ | H | CO | 2 | N | C | C | C | CH₃ | H | H | | | | CH₃ | H | 2 | 3.20 | 288.1 | 287.3 |
| A-152 | CF₃ | H | CO | 2 | N | N | C | C | H | SCH₃ | H | | | | H | H | 1 | 3.99 | 345.2 | 344.3 |
| A-153 | CF₃ | H | CO | 2 | N | N | C | C | — | H | CON(CH₃)₂ | | | | H | H | 1 | 3.82 | 306.1 | 305.3 |
| A-154 | CF₃ | H | CO | 2 | N | N | C | C | — | C(CH₃)₃ | H | | | | H | H | 1 | 2.78 | 331.2 | 330.3 |
| A-155 | CF₃ | H | CO | 2 | N | N | C | C | — | CH₃ | H | | | | C(CH₃)₃ | H | 1 | 4.39 | 316.2 | 315.3 |
| A-156 | CF₃ | H | CO | 2 | N | N | C | C | — | CH₃ | H | | | | OCH₃ | H | 2 | 0.94 | 304.1 | 303.3 |
| A-157 | CF₂CH₃ | H | CO | 2 | N | N | C | C | — | CH₃ | H | | | | OCH₃ | H | 2 | 0.90 | 300.1 | 299.3 |
| A-158 | CF₃ | H | CO | 2 | N | N | C | C | — | CH₃ | H | | | | OCH₂CH₃ | H | 1 | 3.70 | 318.2 | 317.3 |
| A-159 | CF₂CH₃ | H | CO | 2 | N | N | C | C | — | CH₃ | H | | | | OCH₂CH₃ | H | 1 | 3.57 | 314.2 | 313.3 |
| A-160 | CF₂Cl | H | CO | 2 | N | N | C | C | — | CH₃ | H | | | | OCH₂CH₃ | H | 1 | 3.81 | 334.2 | 333.8 |
| A-161 | CF₃ | H | CO | 2 | N | N | C | C | — | CH₃ | CF₃ | | | | H | H | 2 | 1.01 | 328.0 | 327.2 |
| A-162 | CF₃ | H | CO | 2 | N | N | C | C | — | CH₃ | H | | | | H | CF₃ | 2 | 1.02 | 328.1 | 327.2 |
| A-163 | CF₃ | H | CO | 2 | N | N | C | C | — | CH₃ | CN | | | | H | H | 2 | 0.84 | 285.1 | 284.2 |
| A-164 | CF₃ | H | CO | 2 | N | N | C | C | — | CH₃ | CO₂CH₃ | | | | H | H | 2 | 0.86 | 318.1 | 317.3 |
| A-165 | CF₃ | H | CO | 2 | N | N | C | C | — | CH₃ | H | | | | H | CH₂CH₃ | 2 | 0.95 | 300.1 | 299.3 |
| A-166 | CF₃ | H | CO | 2 | N | N | C | C | — | CH₃ | H | | | | cyclopropyl | H | 2 | 0.98 | 288.1 | 287.3 |
| A-167 | CF₃ | H | CO | 2 | N | N | C | C | — | Cl | H | | | | CH₃ | CONH₂ | 2 | 0.88 | 351.0 | 350.7 |

TABLE A-continued

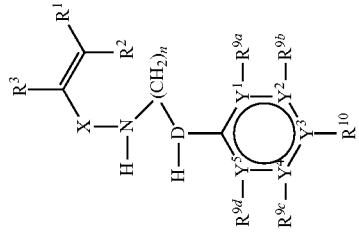

Formula (A)

| | | | | | | | | | | | | | | | | |
|---|---|---|---|---|---|---|---|---|---|---|---|---|---|---|---|---|
| A-168 | CF₃ | H | H | CO | 2 | N | N | C | — | CH₃ | Cl | CH₃ | CN | 2 | 1.14 | 347.1 346.7 |
| A-169 | CF₃ | H | H | CO | 2 | N | N | C | — | H | SO₂NH₂ | H | H | 2 | 0.69 | 339.0 338.3 |
| A-170 | CF₃ | H | H | CO | 2 | N | N | C | — | H | H | phenyl | H | 2 | 1.04 | 336.2 335.3 |
| A-171 | CF₃ | H | H | CO | 2 | N | N | C | — | H | H | CH₂CH₃ | H | 2 | 0.95 | 288.1 287.3 |
| A-172 | CF₃ | H | H | CO | 2 | N | C | C | H | CH₃ | N-piperidinyl | CH₃ | CONH₂ | 2 | 0.82 | 331.2 330.3 |
| A-173 | CF₂Br | H | H | CO | 2 | N | N | C | — | H | H | H | H | 2 | 0.98 | 343.2 342.4 |
| A-174 | CF₂Br | H | H | CO | 2 | N | N | C | — | H | COCH₃ | CH₃ | H | 2 | 0.95 | 334.0 334.2 |
| A-175 | CF₃ | H | H | CO | 2 | N | N | C | — | H | H | OCH₂CH₃ | H | 2 | 0.97 | 364.0 364.2 |
| A-176 | CF₃ | H | H | CO | 2 | N | N | C | — | H | H | H | NH₂ | 2 | 0.80 | 302.2 301.3 |
| A-177 | CF₃ | H | H | CO | 2 | N | N | C | — | H | CH₃ | CH₃ | NH₂ | 2 | 0.82 | 289.2 288.3 |
| A-178 | CF₃ | H | H | CO | 2 | N | N | C | — | CH₃ | CH₃ | CH₃ | H | 2 | 0.92 | 303.2 302.3 |
| A-179 | CF₃ | H | H | CO | 2 | N | N | C | — | CH₃ | H | CO₂CH₃ | H | 2 | 0.95 | 332.1 331.3 |
| A-180 | CF₂Cl | H | H | CO | 2 | N | N | C | — | CH₂CH₃ | H | H | H | 2 | 1.04 | 304.1 303.7 |
| A-181 | CF₂Br | H | H | CO | 2 | N | N | C | — | CH₂CH₃ | H | H | H | 2 | 1.04 | 350.1 348.2 |
| A-182 | CF₂CHF₂ | H | H | CO | 2 | N | N | C | — | CH₂CH₃ | H | H | H | 2 | 1.00 | 320.1 319.3 |
| A-183 | CF₂CH₃ | H | H | CO | 2 | N | N | C | — | (CH₂)₂CH₃ | H | H | H | 2 | 1.03 | 298.2 297.3 |
| A-184 | CF₂Cl | H | H | CO | 2 | N | N | C | — | (CH₂)₂CH₃ | H | H | H | 2 | 1.10 | 318.1 317.8 |
| A-185 | CF₂Br | H | H | CO | 2 | N | N | C | — | (CH₂)₂CH₃ | H | H | H | 2 | 1.11 | 362.0 362.2 |
| A-186 | CF₂CHF₂ | H | H | CO | 2 | N | N | C | — | (CH₂)₂CH₃ | H | H | H | 2 | 1.06 | 334.2 333.3 |
| A-187 | CF₂CH₃ | H | H | CO | 2 | N | N | C | — | CH₂CH₃ | H | H | H | 2 | 0.97 | 284.2 283.3 |
| A-188 | CF₂Br | H | H | CO | 2 | N | N | C | — | H | CH₃ | H | H | 2 | 0.80 | 224.1 223.3 |
| A-189 | CF₂CHF₂ | H | H | CO | 2 | N | N | C | — | H | CONHC₂H₅ | CONHCH₃ | H | 1 | 0.87 | 274.1 273.3 |
| A-190 | CF₂CH₃ | H | H | CO | 2 | N | N | C | — | N(CH₃)₂ | H | H | H | 2 | 2.85 | 331.2 330.3 |
| A-191 | CF₂Cl | H | H | CO | 2 | N | N | C | — | H | H | SO₂CH₃ | H | 2 | 0.73 | 317.1 316.3 |
| A-192 | CF₂Br | H | H | CO | 2 | N | N | C | — | H | NHCOCH₃ | H | H | 2 | 1.04 | 303.1 302.3 |
| A-193 | CF₂CHF₂ | H | H | CO | 2 | N | N | C | — | — | — | H | CON(CH₃)₂ | 2 | 0.77 | 338.1 337.3 |
| A-194 | CF₂CH₃ | H | H | CO | 2 | N | N | C | — | — | — | H | NHCOC(CH₃)₃ | 2 | 0.81 | 331.1 330.3 |
| A-195 | H | F | H | CO | 2 | N | N | C | — | — | SCH₃ | H | H | 2 | 1.00 | 359.2 358.4 |
| A-196 | H | CF₃ | H | CO | 2 | N | N | C | — | H | H | H | SO₂NH₂ | 2 | 0.72 | 317.1 316.6 |
| A-197 | CF₃ | H | H | CO | 2 | N | C | C | H | N-piperidinyl | H | H | H | 2 | 0.68 | 339.0 338.3 |
| A-198 | CF₃ | H | H | CO | 2 | N | N | C | — | — | H | CH₃ | H | 2 | 0.89 | 306.1 305.3 |
| A-199 | CF₃ | H | H | CO | 2 | N | N | N | H | — | — | H | H | 2 | 0.75 | 343.1 342.4 |
| A-200 | CF₃ | H | H | CO | 2 | N | C | C | — | H | Y²—CH=N—N=Y³ | H | H | 1 | 0.88 | 290.1 289.7 |
| A-201 | CF₃ | H | H | CO | 2 | N | N | C | — | H | H | H | H | 1 | 2.57 | 301.1 300.2 |
| A-202 | CF₃ | H | H | CO | 2 | N | N | C | — | H | H | Phenyl | H | 1 | 3.84 | 336.2 335.3 |

TABLE A-continued

Formula (A) structure: 
R¹, R², R³ attached to C=X-N(H)-(CH₂)ₙ-D(H)- linked to phenyl ring with Y¹-Y⁵ positions bearing R⁹ᵃ, R⁹ᵇ, R⁹ᶜ, R⁹ᵈ, R¹⁰ substituents.

| | R¹ | R² | R³ | Y¹ | Y² | Y⁴ | Y⁵ | R⁹ᵃ | R⁹ᵇ | R¹⁰ | R⁹ᶜ | R⁹ᵈ | RT | [M+H] found | [M+H] calc | Synth. method |
|---|---|---|---|---|---|---|---|---|---|---|---|---|---|---|---|---|
| A-203 | CF₃ | H | H | CO | 2 | N | N | — | H | H | COCH₃ | H | 0.85 | 302.1 | 301.3 | |
| A-204 | CF₃ | H | H | CO | 2 | N | N | — | Y²–C(CH₃)=N–N=Y³ | H | H | H | 0.72 | 315.1 | 314.3 | |

(Y³ = C, X = CO, n = 2, D = N)

| | R¹ | R² | R³ | Y¹ | Y² | Y⁴ | Y⁵ | R⁹ᵃ | R⁹ᵇ | R¹⁰ | R⁹ᶜ | R⁹ᵈ | Synth. method |
|---|---|---|---|---|---|---|---|---|---|---|---|---|---|
| A-205 | CHF₂ | H | H | N | C | C | C | — | H | H | C₂H₅ | H | 3A; 6B |
| A-206 | CF₂CH₃ | H | H | N | C | C | C | — | H | H | C₂H₅ | H | 3A; 6B |
| A-207 | CF₂Cl | H | H | N | C | C | C | — | H | H | C₂H₅ | H | 3A; 6B |
| A-208 | CF₂Br | H | H | N | C | C | C | — | H | H | C₂H₅ | H | 3A; 6B |
| A-209 | CF₂CHF₂ | H | H | N | C | C | C | — | H | H | C₂H₅ | H | 3A; 6B |
| A-210 | CF₂CF₃ | H | H | N | C | C | C | — | H | H | C₂H₅ | H | 3A; 6B |
| A-211 | CF₂Br | H | H | N | C | C | C | — | H | H | OCH₃ | H | 3A; 6B |
| A-212 | CHF₂ | H | H | N | C | C | C | — | CH₃ | H | H | H | 3A; 6B |
| A-213 | CF₂CF₃ | H | H | N | C | C | C | — | C₂H₅ | H | H | H | 3A; 6B |
| A-214 | CF₂Br | H | H | N | C | C | C | — | C₂H₅ | H | H | H | 3A; 6B |
| A-215 | CHF₂ | H | H | N | C | C | C | — | CH₃ | H | CH₃ | H | 3A; 6B |
| A-217 | CF₂CHF₂ | H | H | N | C | C | C | — | H | H | H | H | 3A; 6B |
| A-218 | CF₂CF₃ | H | H | N | C | C | C | — | H | H | H | H | 3A; 6B |
| A-219 | CF₂Cl | H | H | N | C | C | C | — | H | H | H | H | 3A; 6B |
| A-220 | CF₂Br | H | H | N | C | C | C | — | H | CH₃ | H | H | 3A; 6B |
| A-221 | CHF₂ | H | H | N | C | C | C | — | CH₃ | CH₃ | H | H | 3A; 6B |
| A-222 | CF₂CHF₂ | H | H | N | C | C | C | — | CH₃ | CH₃ | H | H | 3A; 6B |
| A-223 | CF₂CF₃ | H | H | N | C | C | C | — | CH₃ | CH₃ | H | H | 3A; 6B |
| A-224 | CHF₂ | H | H | N | C | C | C | — | CH₃ | CH₃ | H | H | 3A; 6B |
| A-225 | CF₂Cl | H | H | N | C | C | C | — | CH₃ | H | OCH₃ | H | 19A-E; 6B |
| A-226 | CF₂Br | H | H | N | C | C | C | — | CH₃ | H | OCH₃ | H | 19A-E; 6B |
| A-227 | CF₂CHF₂ | H | H | N | C | C | C | — | CH₃ | H | OCH₃ | H | 19A-E; 6B |
| A-228 | CF₂CF₃ | H | H | N | C | C | C | — | CH₃ | H | OCH₃ | H | 19A-E; 6B |
| A-229 | CHF₂ | H | H | N | C | C | C | — | CH₃ | H | OCH₃ | H | 19A-E; 6B |
| A-230 | CF₂Br | H | H | N | C | C | C | — | CH₃ | H | OCH₂CH₃ | H | 19A-E; 6B |
| A-231 | CF₂CHF₂ | H | H | N | C | C | C | — | CH₃ | H | OCH₂CH₃ | H | 19A-E; 6B |
| A-232 | CF₂CF₃ | H | H | N | C | C | C | — | CH₃ | H | OCH₂CH₃ | H | 19A-E; 6B |

TABLE A-continued

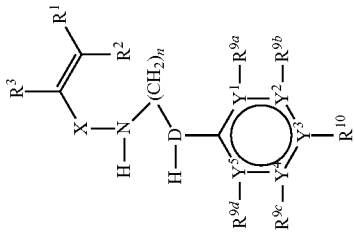

Formula (A)

| No. | | | | | | | | | | | | Formula |
|---|---|---|---|---|---|---|---|---|---|---|---|---|
| A-233 | CF$_2$CF$_3$ | H | H | N | C | C | — | CH$_3$ | H | OCH$_2$CH$_3$ | H | 19A-E; 6B |
| A-234 | CHF$_2$ | H | H | N | C | C | — | (CH$_2$)$_2$CH$_3$ | H | H | H | 3A; 6B |
| A-235 | CF$_2$CF$_3$ | H | H | N | C | C | — | (CH$_2$)$_2$CH$_3$ | H | H | H | 3A; 6B |
| A-236 | CHF$_2$ | H | H | N | C | C | — | CH(CH$_3$)$_2$ | H | H | H | 3A; 6B |
| A-237 | CF$_2$Cl | H | H | N | C | C | — | CH(CH$_3$)$_2$ | H | H | H | 3A; 6B |
| A-238 | CF$_2$Br | H | H | N | C | C | — | CH(CH$_3$)$_2$ | H | H | H | 3A; 6B |
| A-239 | CF$_2$CHF$_2$ | H | H | N | C | C | — | CH(CH$_3$)$_2$ | H | H | H | 3A; 6B |
| A-240 | CF$_2$CF$_3$ | H | H | N | C | C | — | CH(CH$_3$)$_2$ | H | H | H | 3A; 6B |
| A-241 | CHF$_2$ | H | H | N | C | C | — | H | H | CH(CH$_3$)$_2$ | H | 3A; 6B |
| A-242 | CF$_2$Cl | H | H | N | C | C | — | H | H | CH(CH$_3$)$_2$ | H | 3A; 6B |
| A-243 | CF$_2$Br | H | H | N | C | C | — | H | H | CH(CH$_3$)$_2$ | H | 3A; 6B |
| A-244 | CF$_2$CH$_3$ | H | H | N | C | C | — | H | H | CH(CH$_3$)$_2$ | H | 3A; 6B |
| A-245 | CF$_2$CHF$_2$ | H | H | N | C | C | — | H | H | CH(CH$_3$)$_2$ | H | 3A; 6B |
| A-246 | CF$_2$CF$_3$ | H | H | N | C | C | — | H | H | CH(CH$_3$)$_2$ | H | 3A; 6B |
| A-247 | CF$_3$ | H | H | N | C | C | — | H | H | (CH$_2$)$_2$CH$_3$ | H | 3A; 6B |
| A-248 | CHF$_2$ | H | H | N | C | C | — | H | H | (CH$_2$)$_2$CH$_3$ | H | 3A; 6B |
| A-249 | CF$_2$Cl | H | H | N | C | C | — | H | H | (CH$_2$)$_2$CH$_3$ | H | 3A; 6B |
| A-250 | CF$_2$Br | H | H | N | C | C | — | H | H | (CH$_2$)$_2$CH$_3$ | H | 3A; 6B |
| A-251 | CF$_2$CH$_3$ | H | H | N | C | C | — | H | H | (CH$_2$)$_2$CH$_3$ | H | 3A; 6B |
| A-252 | CF$_2$CHF$_2$ | H | H | N | C | C | — | H | H | (CH$_2$)$_2$CH$_3$ | H | 3A; 6B |
| A-253 | CF$_2$CF$_3$ | H | H | N | C | C | — | H | H | (CH$_2$)$_2$CH$_3$ | H | 3A; 6B |
| A-254 | CHF$_2$ | H | H | N | C | C | — | H | H | cyclopropyl | H | 3A; 6B |
| A-255 | CF$_2$Cl | H | H | N | C | C | — | cyclopropyl | H | cyclopropyl | H | 3A; 6B |
| A-256 | CF$_2$Br | H | H | N | C | C | — | cyclopropyl | H | cyclopropyl | H | 3A; 6B |
| A-257 | CF$_2$CH$_3$ | H | H | N | C | C | — | cyclopropyl | H | cyclopropyl | H | 3A; 6B |
| A-258 | CF$_2$CHF$_2$ | H | H | N | C | C | — | cyclopropyl | H | cyclopropyl | H | 3A; 6B |
| A-259 | CF$_2$CF$_3$ | H | H | N | C | C | — | cyclopropyl | H | cyclopropyl | H | 3A; 6B |
| A-260 | CF$_3$ | H | H | N | C | C | — | cyclopropyl | H | — | H | 3A; 6B |
| A-261 | CHF$_2$ | H | H | N | C | C | — | H | H | H | H | 3A; 6B |
| A-262 | CF$_2$Cl | H | H | N | C | C | — | H | H | H | H | 3A; 6B |
| A-263 | CF$_2$Br | H | H | N | C | C | — | H | H | H | H | 3A; 6B |
| A-264 | CF$_2$CH$_3$ | H | H | N | C | C | — | H | H | H | H | 3A; 6B |
| A-265 | CF$_2$CHF$_2$ | H | H | N | C | C | — | H | H | H | H | 3A; 6B |
| A-266 | CF$_2$CF$_3$ | H | H | C | N | C | — | H | H | H | H | 3A; 6B |
| A-267 | CHF$_2$ | H | H | N | C | C | CH$_3$ | H | H | CH$_3$ | H | 3A; 6B |

TABLE A-continued

| No. | R³ | | | X | | | | | | | Formula (A) |
|---|---|---|---|---|---|---|---|---|---|---|---|
| A-268 | CF₂Cl | H | H | N | C | CH₃ | — | H | CH₃ | H | 3A; 6B |
| A-269 | CF₂Br | H | H | N | C | CH₃ | — | H | CH₃ | H | 3A; 6B |
| A-270 | CF₂CH₃ | H | H | N | C | CH₃ | — | H | CH₃ | H | 3A; 6B |
| A-271 | CF₂CF₃ | H | H | N | C | CH₃ | — | H | CH₃ | H | 3A; 6B |
| A-272 | CHF₂ | H | H | N | C | H | — | H | H | CH₃ | 3A; 6B |
| A-273 | CF₂Cl | H | H | N | C | H | — | H | H | CH₃ | 3A; 6B |
| A-274 | CF₂Br | H | H | N | C | H | — | H | H | CH₃ | 3A; 6B |
| A-275 | CF₂CHF₂ | H | H | N | C | H | — | H | H | CH₃ | 3A; 6B |
| A-276 | CF₂CF₃ | H | H | N | C | H | — | H | H | CH₃ | 3A; 6B |
| A-277 | CF₃ | H | H | N | C | H | — | H | CH₃ | H | 3A; 6B |
| A-278 | CHF₂ | H | H | N | C | H | — | H | CH₃ | H | 3A; 6B |
| A-279 | CF₂Cl | H | H | N | C | H | — | H | CH₃ | H | 3A; 6B |
| A-280 | CF₂Br | H | H | N | C | H | — | H | CH₃ | H | 3A; 6B |
| A-281 | CF₂CHF₂ | H | H | N | C | H | — | H | CH₃ | H | 3A; 6B |
| A-282 | CF₂CF₃ | H | H | N | C | H | — | H | CH₃ | H | 3A; 6B |
| A-283 | CF₂CH₃ | H | H | N | C | CH₃ | — | H | CH₃ | H | 3A; 6B |
| A-284 | CF₃ | H | H | N | C | CH₃ | — | H | H | H | 3A; 6B |
| A-285 | CHF₂ | H | H | N | C | H | — | H | H | H | 3A; 6B |
| A-286 | CF₂Cl | H | H | N | C | H | — | H | H | C₂H₅ | 3A; 6B |
| A-287 | CF₂Br | H | H | N | C | H | — | H | H | C₂H₅ | 3A; 6B |
| A-288 | CF₂CHF₂ | H | H | N | C | H | — | H | H | C₂H₅ | 3A; 6B |
| A-289 | CF₂CF₃ | H | H | N | C | H | — | H | H | C₂H₅ | 3A; 6B |
| A-290 | CF₂CH₃ | H | H | N | C | H | — | H | H | C₂H₅ | 3A; 6B |
| A-291 | CF₃ | H | H | N | C | H | — | H | H | C₂H₅ | 3A; 6B |
| A-292 | CHF₂ | H | H | N | C | H | — | C₂H₅ | H | H | 3A; 6B |
| A-293 | CF₂Cl | H | H | N | C | H | — | C₂H₅ | H | H | 3A; 6B |
| A-294 | CF₂Br | H | H | N | C | H | — | C₂H₅ | H | H | 3A; 6B |
| A-295 | CF₂CHF₂ | H | H | N | C | H | — | C₂H₅ | H | H | 3A; 6B |
| A-296 | CF₂CF₃ | H | H | N | C | H | — | C₂H₅ | H | H | 3A; 6B |
| A-297 | CF₂CH₃ | H | H | N | C | H | — | C₂H₅ | H | H | 3A; 6B |
| A-298 | CF₂Br | H | H | N | C | H | — | C₂H₅ | H | H | 3A; 6B |
| A-299 | CF₂CH₃ | H | H | N | C | CH₃ | — | H | H | H | 3A; 6B |
| A-300 | CHF₂ | H | H | N | C | CH₃ | — | CH₃ | H | H | 3A; 6B |
| A-301 | CF₂Br | H | H | N | C | CH₃ | — | CH₃ | H | H | 3A; 6B |
| A-302 | CF₂Cl | H | H | N | C | CH₃ | — | CH₃ | H | H | 3A; 6B |

TABLE A-continued

| | | | | | | | | | | | Formula (A) |
|---|---|---|---|---|---|---|---|---|---|---|---|
| A-303 | CF₂CHF₂ | H | H | N | C | C | CH₃ | CH₃ | H | H | 3A; 6B |
| A-304 | CF₂CF₃ | H | H | N | C | C | CH₃ | CH₃ | H | H | 3A; 6B |
| A-305 | CF₃ | H | H | N | C | C | H | CH₃ | H | H | 3A; 6B |
| A-306 | CF₂Br | H | H | N | C | C | H | CH₃ | H | H | 3A; 6B |
| A-307 | CHF₂ | H | H | N | C | C | H | CH₃ | H | H | 3A; 6B |
| A-308 | CF₂Cl | H | H | N | C | C | H | CH₃ | H | H | 3A; 6B |
| A-309 | CF₂CHF₂ | H | H | N | C | C | H | CH₃ | H | H | 3A; 6B |
| A-310 | CF₂CF₃ | H | H | N | C | C | H | CH₃ | H | H | 3A; 6B |
| A-311 | CF₃ | H | H | N | C | C | H | CH₃ | CH₃ | CH₃ | 3A; 6B |
| A-312 | CHF₂ | H | H | N | C | C | H | CH₃ | CH₃ | CH₃ | 3A; 6B |
| A-313 | CF₂Cl | H | H | N | C | C | H | CH₃ | CH₃ | CH₃ | 3A; 6B |
| A-314 | CF₂Br | H | H | N | C | C | H | CH₃ | CH₃ | CH₃ | 3A; 6B |
| A-315 | CF₂CH₃ | H | H | N | C | C | H | CH₃ | CH₃ | CH₃ | 3A; 6B |
| A-316 | CF₂CHF₂ | H | H | N | C | C | H | CH₃ | CH₃ | CH₃ | 3A; 6B |
| A-317 | CF₂CF₃ | H | H | N | C | C | H | CH₃ | CH₃ | CH₃ | 3A; 6B |
| A-318 | CF₃ | H | H | N | C | C | H | CH₃ | CH₃ | H | 3A; 6B |
| A-319 | CHF₂ | H | H | N | C | C | H | CH₃ | H | H | 3A; 6B |
| A-320 | CF₂Cl | H | H | N | C | C | H | CH₃ | H | H | 3A; 6B |
| A-321 | CF₂Br | H | H | N | C | C | H | CH₃ | H | H | 3A; 6B |
| A-322 | CF₂CH₃ | H | H | N | C | C | H | CH₃ | H | H | 3A; 6B |
| A-323 | CF₂CHF₂ | H | H | N | C | C | H | CH₃ | H | H | 3A; 6B |
| A-324 | CF₂CF₃ | H | H | N | C | C | CH₃ | H | H | H | 3A; 6B |
| A-325 | CHF₂ | H | H | N | C | C | CH₃ | H | H | H | 3A; 6B |
| A-326 | CF₂Cl | H | H | N | C | C | CH₃ | H | H | H | 3A; 6B |
| A-327 | CF₂Br | H | H | N | C | C | CH₃ | H | H | H | 3A; 6B |
| A-328 | CF₂CHF₂ | H | H | N | C | C | CH₃ | H | H | H | 3A; 6B |
| A-329 | CF₂CF₃ | H | H | N | C | C | CH₃ | H | H | H | 3A; 6B |
| A-330 | CF₃ | H | H | N | C | C | C₂H₅ | H | H | H | 3A; 6B |
| A-331 | CHF₂ | H | H | N | C | C | C₂H₅ | H | H | H | 3A; 6B |
| A-332 | CF₂Cl | H | H | N | C | C | C₂H₅ | H | H | H | 3A; 6B |
| A-333 | CF₂Br | H | H | N | C | C | C₂H₅ | H | H | H | 3A; 6B |
| A-334 | CF₂CH₃ | H | H | N | C | C | C₂H₅ | H | H | H | 3A; 6B |
| A-335 | CF₂CHF₂ | H | H | N | C | C | C₂H₅ | H | H | H | 3A; 6B |
| A-336 | CF₂CF₃ | H | H | N | C | C | C₂H₅ | H | H | H | 3A; 6B |
| A-337 | CF₃ | H | H | N | C | C | CH(CH₃)₂ | H | H | H | 3A; 6B |

TABLE A-continued

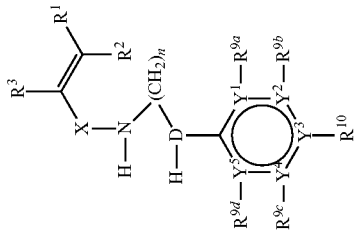

| | | | | | | | | | | | | Formula (A) |
|---|---|---|---|---|---|---|---|---|---|---|---|---|
| A-338 | CHF$_2$ | H | H | C | N | C | CH(CH$_3$)$_2$ | — | H | H | H | 3A; 6B |
| A-339 | CF$_2$Cl | H | H | C | N | C | CH(CH$_3$)$_2$ | — | H | H | H | 3A; 6B |
| A-340 | CF$_2$Br | H | H | C | N | C | CH(CH$_3$)$_2$ | — | H | H | H | 3A; 6B |
| A-341 | CF$_2$CH$_3$ | H | H | C | N | C | CH(CH$_3$)$_2$ | — | H | H | H | 3A; 6B |
| A-342 | CF$_2$CHF$_2$ | H | H | C | N | C | CH(CH$_3$)$_2$ | — | H | H | H | 3A; 6B |
| A-343 | CF$_2$CF$_3$ | H | H | C | N | C | CH(CH$_3$)$_2$ | — | H | H | H | 3A; 6B |
| A-344 | CF$_3$ | H | H | C | N | C | H | — | H | H | SCH$_3$ | 3A; 6B |
| A-345 | CHF$_2$ | H | H | C | N | C | H | — | H | H | SCH$_3$ | 3A; 6B |
| A-346 | CF$_2$Cl | H | H | C | N | C | H | — | H | H | SCH$_3$ | 3A; 6B |
| A-347 | CF$_2$Br | H | H | C | N | C | H | — | H | H | SCH$_3$ | 3A; 6B |
| A-348 | CF$_2$CH$_3$ | H | H | C | N | C | H | — | H | H | SCH$_3$ | 3A; 6B |
| A-349 | CF$_2$CHF$_2$ | H | H | C | N | C | H | — | H | H | SCH$_3$ | 3A; 6B |
| A-350 | CF$_2$CF$_3$ | H | H | C | N | C | H | — | H | H | SCH$_3$ | 3A; 6B |
| A-351 | CF$_3$ | H | H | C | N | C | H | — | H | H | SC$_2$H$_5$ | 3A; 6B |
| A-352 | CHF$_2$ | H | H | C | N | C | H | — | H | H | SC$_2$H$_5$ | 3A; 6B |
| A-353 | CF$_2$Cl | H | H | C | N | C | H | — | H | H | SC$_2$H$_5$ | 3A; 6B |
| A-354 | CF$_2$Br | H | H | C | N | C | H | — | H | H | SC$_2$H$_5$ | 3A; 6B |
| A-355 | CF$_2$CH$_3$ | H | H | C | N | C | H | — | H | H | SC$_2$H$_5$ | 3A; 6B |
| A-356 | CF$_2$CHF$_2$ | H | H | C | N | C | H | — | H | H | SC$_2$H$_5$ | 3A; 6B |
| A-357 | CF$_2$CF$_3$ | H | H | C | N | C | H | — | H | H | SC$_2$H$_5$ | 3A; 6B |
| A-358 | CF$_3$ | H | H | C | N | C | CH$_3$ | — | H | H | SCH$_3$ | 3A; 6B |
| A-359 | CHF$_2$ | H | H | C | N | C | CH$_3$ | — | H | H | SCH$_3$ | 3A; 6B |
| A-360 | CF$_2$Cl | H | H | C | N | C | CH$_3$ | — | H | H | SCH$_3$ | 3A; 6B |
| A-361 | CF$_2$Br | H | H | C | N | C | CH$_3$ | — | H | H | SCH$_3$ | 3A; 6B |
| A-362 | CF$_2$CH$_3$ | H | H | C | N | C | CH$_3$ | — | H | H | SCH$_3$ | 3A; 6B |
| A-363 | CF$_2$CHF$_2$ | H | H | C | N | C | CH$_3$ | — | H | H | SCH$_3$ | 3A; 6B |
| A-364 | CF$_2$CF$_3$ | H | H | C | N | C | CH$_3$ | — | H | H | SCH$_3$ | 3A; 6B |
| A-365 | CF$_3$ | H | H | C | N | C | CH$_3$ | — | H | H | SC$_2$H$_5$ | 3A; 6B |
| A-366 | CHF$_2$ | H | H | C | N | C | CH$_3$ | — | H | H | SC$_2$H$_5$ | 3A; 6B |
| A-367 | CF$_2$Cl | H | H | C | N | C | CH$_3$ | — | H | H | SC$_2$H$_5$ | 3A; 6B |
| A-368 | CF$_2$Br | H | H | C | N | C | CH$_3$ | — | H | H | SC$_2$H$_5$ | 3A; 6B |
| A-369 | CF$_2$CH$_3$ | H | H | C | N | C | CH$_3$ | — | H | H | SC$_2$H$_5$ | 3A; 6B |
| A-370 | CF$_2$CHF$_2$ | H | H | C | N | C | CH$_3$ | — | H | H | SC$_2$H$_5$ | 3A; 6B |
| A-371 | CF$_2$CF$_3$ | H | H | C | N | C | CH$_3$ | — | H | H | SC$_2$H$_5$ | 3A; 6B |
| A-372 | CF$_3$ | H | H | C | N | C | CH$_3$ | — | H | H | OCH$_3$ | 3A; 6B |

TABLE A-continued

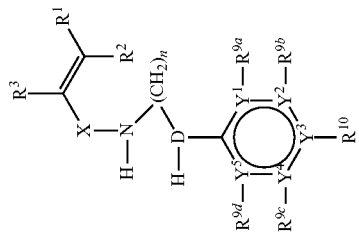

| | | | | | | | | | | | | | Formula (A) |
|---|---|---|---|---|---|---|---|---|---|---|---|---|---|
| A-373 | CHF$_2$ | H | H | C | C | C | CH$_3$ | — | H | H | OCH$_3$ | 3A; 6B |
| A-374 | CF$_2$Cl | H | H | C | N | C | CH$_3$ | — | H | H | OCH$_3$ | 3A; 6B |
| A-375 | CF$_2$Br | H | H | C | N | C | CH$_3$ | — | H | H | OCH$_3$ | 3A; 6B |
| A-376 | CF$_2$CH$_3$ | H | H | C | N | C | CH$_3$ | — | H | H | OCH$_3$ | 3A; 6B |
| A-377 | CF$_2$CHF$_2$ | H | H | C | N | C | CH$_3$ | — | H | H | OCH$_3$ | 3A; 6B |
| A-378 | CF$_2$CF$_3$ | H | H | C | N | C | CH$_3$ | — | H | H | OCH$_3$ | 3A; 6B |
| A-379 | CF$_3$ | H | H | C | N | C | CH$_3$ | — | H | H | OC$_2$H$_5$ | 3A; 6B |
| A-380 | CHF$_2$ | H | H | C | N | C | CH$_3$ | — | H | H | OC$_2$H$_5$ | 3A; 6B |
| A-381 | CF$_2$Cl | H | H | C | N | C | CH$_3$ | — | H | H | OC$_2$H$_5$ | 3A; 6B |
| A-382 | CF$_2$Br | H | H | C | N | C | CH$_3$ | — | H | H | OC$_2$H$_5$ | 3A; 6B |
| A-383 | CF$_2$CH$_3$ | H | H | C | N | C | CH$_3$ | — | H | H | OC$_2$H$_5$ | 3A; 6B |
| A-384 | CF$_2$CHF$_2$ | H | H | C | N | C | CH$_3$ | — | H | H | OC$_2$H$_5$ | 3A; 6B |
| A-385 | CF$_2$CF$_3$ | H | H | C | N | C | CH$_3$ | — | H | H | OC$_2$H$_5$ | 3A; 6B |
| A-386 | CF$_3$ | H | H | C | C | C | — | H | H | SCH$_3$ | H | 19A-E; 6B |
| A-387 | CHF$_2$ | H | H | C | N | C | — | H | H | SCH$_3$ | H | 19A-E; 6B |
| A-388 | CF$_2$Cl | H | H | C | N | C | — | H | H | SCH$_3$ | H | 19A-E; 6B |
| A-389 | CF$_2$Br | H | H | C | N | C | — | H | H | SCH$_3$ | H | 19A-E; 6B |
| A-390 | CF$_2$CH$_3$ | H | H | C | N | C | — | H | H | SCH$_3$ | H | 19A-E; 6B |
| A-391 | CF$_2$CHF$_2$ | H | H | C | N | C | — | H | H | SCH$_3$ | H | 19A-E; 6B |
| A-392 | CF$_2$CF$_3$ | H | H | C | N | C | — | H | H | SC$_2$H$_5$ | H | 19A-E; 6B |
| A-393 | CF$_3$ | H | H | C | N | C | — | H | H | SC$_2$H$_5$ | H | 19A-E; 6B |
| A-394 | CHF$_2$ | H | H | C | N | C | — | H | H | SC$_2$H$_5$ | H | 19A-E; 6B |
| A-395 | CF$_2$Cl | H | H | C | N | C | — | H | H | SC$_2$H$_5$ | H | 19A-E; 6B |
| A-396 | CF$_2$Br | H | H | C | N | C | — | H | H | SCH$_3$ | H | 19A-E; 6B |
| A-397 | CF$_2$CH$_3$ | H | H | C | N | C | — | H | H | SCH$_3$ | H | 19A-E; 6B |
| A-398 | CF$_2$CHF$_2$ | H | H | C | N | C | — | H | H | SCH$_3$ | H | 19A-E; 6B |
| A-399 | CF$_2$CF$_3$ | H | H | C | N | C | — | H | H | SCH$_3$ | H | 19A-E; 6B |
| A-400 | CF$_3$ | H | H | C | C | C | — | CH$_3$ | H | SCH$_3$ | H | 19A-E; 6B |
| A-401 | CHF$_2$ | H | H | C | N | C | — | CH$_3$ | H | SCH$_3$ | H | 19A-E; 6B |
| A-402 | CF$_2$Cl | H | H | C | N | C | — | CH$_3$ | H | SCH$_3$ | H | 19A-E; 6B |
| A-403 | CF$_2$Br | H | H | C | N | C | — | CH$_3$ | H | SCH$_3$ | H | 19A-E; 6B |
| A-404 | CF$_2$CH$_3$ | H | H | C | N | C | — | CH$_3$ | H | SCH$_3$ | H | 19A-E; 6B |
| A-405 | CF$_2$CHF$_2$ | H | H | C | N | C | — | CH$_3$ | H | SCH$_3$ | H | 19A-E; 6B |
| A-406 | CF$_2$CF$_3$ | H | H | C | N | C | — | CH$_3$ | H | SCH$_3$ | H | 19A-E; 6B |
| A-407 | CF$_3$ | H | H | C | N | C | — | CH$_3$ | H | SC$_2$H$_5$ | H | 19A-E; 6B |

TABLE A-continued

Formula (A)

| | | | | | | | | | | | | | | Formula |
|---|---|---|---|---|---|---|---|---|---|---|---|---|---|---|
| A-408 | CHF$_2$ | H | H | N | C | C | C | — | CH$_3$ | H | SC$_2$H$_5$ | H | | 19A-E; 6B |
| A-409 | CF$_2$Cl | H | H | N | C | C | C | — | CH$_3$ | H | SC$_2$H$_5$ | H | | 19A-E; 6B |
| A-410 | CF$_2$Br | H | H | N | C | C | C | — | CH$_3$ | H | SC$_2$H$_5$ | H | | 19A-E; 6B |
| A-411 | CF$_2$CH$_3$ | H | H | N | C | C | C | — | CH$_3$ | H | SC$_2$H$_5$ | H | | 19A-E; 6B |
| A-412 | CF$_2$CHF$_2$ | H | H | N | C | C | C | — | CH$_3$ | H | SC$_2$H$_5$ | H | | 19A-E; 6B |
| A-413 | CF$_2$CF$_3$ | H | H | N | C | C | C | — | CH$_3$ | H | SC$_2$H$_5$ | H | | 19A-E; 6B |
| A-414 | CF$_3$ | H | H | N | C | C | C | — | CH$_3$ | H | H | CH$_3$ | | 3A; 6B |
| A-415 | CHF$_2$ | H | H | N | C | C | C | — | CH$_3$ | H | H | CH$_3$ | | 3A; 6B |
| A-416 | CF$_2$Cl | H | H | N | C | C | C | — | CH$_3$ | H | H | CH$_3$ | | 3A; 6B |
| A-417 | CF$_2$Br | H | H | N | C | C | C | — | CH$_3$ | H | H | CH$_3$ | | 3A; 6B |
| A-418 | CF$_2$CH$_3$ | H | H | N | C | C | C | — | CH$_3$ | H | H | CH$_3$ | | 3A; 6B |
| A-419 | CF$_2$CHF$_2$ | H | H | N | C | C | C | — | CH$_3$ | H | H | CH$_3$ | | 3A; 6B |
| A-420 | CF$_2$CF$_3$ | H | H | N | C | C | C | — | CH$_3$ | H | H | H | | 3A; 6B |
| A-421 | CF$_3$ | H | H | N | C | C | C | — | (CH$_2$)$_3$CH$_3$ | H | H | H | | 3A; 6B |
| A-422 | CHF$_2$ | H | H | N | C | C | C | — | (CH$_2$)$_3$CH$_3$ | H | H | H | | 3A; 6B |
| A-423 | CF$_2$Cl | H | H | N | C | C | C | — | (CH$_2$)$_3$CH$_3$ | H | H | H | | 3A; 6B |
| A-424 | CF$_2$Br | H | H | N | C | C | C | — | (CH$_2$)$_3$CH$_3$ | H | H | H | | 3A; 6B |
| A-425 | CF$_2$CH$_3$ | H | H | N | C | C | C | — | (CH$_2$)$_3$CH$_3$ | H | H | H | | 3A; 6B |
| A-426 | CF$_2$CHF$_2$ | H | H | N | C | C | C | — | (CH$_2$)$_3$CH$_3$ | H | H | H | | 3A; 6B |
| A-427 | CF$_2$CF$_3$ | H | H | N | C | C | C | — | (CH$_2$)$_3$CH$_3$ | H | H | H | | 3A; 6B |
| A-428 | CF$_3$ | H | H | N | C | C | C | — | H | H | (CH$_2$)$_3$CH$_3$ | H | | 3A; 6B |
| A-429 | CHF$_2$ | H | H | N | C | C | C | — | H | H | (CH$_2$)$_3$CH$_3$ | H | | 3A; 6B |
| A-430 | CF$_2$Cl | H | H | N | C | C | C | — | H | H | (CH$_2$)$_3$CH$_3$ | H | | 3A; 6B |
| A-431 | CF$_2$Br | H | H | N | C | C | C | — | H | H | (CH$_2$)$_3$CH$_3$ | H | | 3A; 6B |
| A-432 | CF$_2$CH$_3$ | H | H | N | C | C | C | — | H | H | (CH$_2$)$_3$CH$_3$ | H | | 3A; 6B |
| A-433 | CF$_2$CHF$_2$ | H | H | N | C | C | C | — | H | H | (CH$_2$)$_3$CH$_3$ | H | | 3A; 6B |
| A-434 | CF$_2$CF$_3$ | H | H | N | C | C | C | — | H | H | (CH$_2$)$_3$CH$_3$ | H | | 3A; 6B |
| A-435 | CH$_2$OCH$_3$ | H | H | N | C | C | C | — | H | H | CH$_3$ | H | | 6B |

Table B below provides for each of the exemplified compounds of the formula (A) the structure, the calculated molecular weight (MW) (gram/mol), the observed MS signal (m/z), the HPLC retention time (Rt) in minutes and the number of the HPLC-method as described in paragraph C above ("Analytics: HPLC-Methods") used for analysis. If a compound contains a chiral center, the racemate is present.

TABLE B

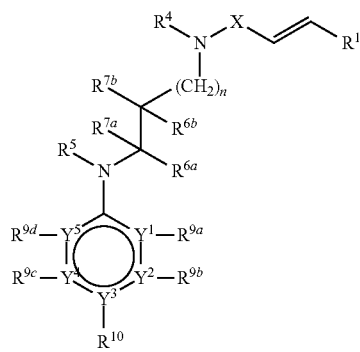

Formula (B)

($R^{7a}$ = H, X = CO)

| No | $R^1$ | n | $R^{6a}$ | $R^4$ | $R^{6b}$ | $R^{7b}$ | $R^5$ | $Y^1$ | $Y^2$ | $Y^3$ | $Y^4$ | $Y^5$ | $R^{9a}$ | $R^{9b}$ | $R^{10}$ | $R^{9c}$ | $R^{9d}$ | HPLC | RT | m/z | MW |
|---|---|---|---|---|---|---|---|---|---|---|---|---|---|---|---|---|---|---|---|---|---|
| B-1 | $CF_3$ | 1 | H | —$(CH_2)_2$— | | —$(CH_2)_3$— | | N | C | C | C | C | — | H | H | $CH_3$ | H | 2 | 1.10 | 354.1 | 353.4 |
| B-2 | $CH(CH_3)_2$ | 1 | H | —$(CH_2)_2$— | | —$(CH_2)_3$— | | N | C | C | C | C | — | H | H | $CH_3$ | H | 2 | 1.12 | 328.2 | 327.5 |
| B-3 | $CF_3$ | 0 | H | $CH_2CH_3$ | H | H | H | N | C | C | C | C | — | H | H | $CH_3$ | H | 2 | 1.00 | 302.1 | 301.3 |
| B-4 | $CF_3$ | 0 | H | $CH_3$ | H | H | $CH_3$ | N | C | C | C | C | — | H | H | $CH_3$ | H | 2 | 1.03 | 302.1 | 301.3 |
| B-5 | $CF_3$ | 0 | H | H | H | H | $CH_3$ | N | C | C | C | C | — | H | H | $CH_3$ | H | 2 | 0.99 | 288.1 | 287.3 |
| B-6 | $CF_3$ | 0 | H | H | benzyl | H | H | N | C | C | C | C | — | H | H | $CH_3$ | H | 2 | 1.10 | 364.1 | 363.4 |
| B-7 | $CF_3$ | 0 | H | H | H | H | $CH_2CH_3$ | N | C | C | C | C | — | H | H | $CH_3$ | H | 2 | 1.06 | 302.1 | 301.3 |
| B-8 | $CF_3$ | 0 | H | H | phenyl | H | H | N | C | C | C | C | — | H | H | $CH_3$ | H | 2 | 1.09 | 350.1 | 349.4 |
| B-9 | $CF_3$ | 0 | $CH_3$ | H | H | H | H | N | C | C | C | C | — | H | H | $CH_3$ | H | 2 | 0.95 | 288.0 | 287.3 |
| B-10 | $CF_3$ | 0 | H | $CH_3$ | H | H | H | N | C | C | C | C | — | H | H | $CH_3$ | H | 2 | 0.93 | 288.1 | 287.3 |
| B-11 | $CF_3$ | 0 | H | $CH_2CH_3$ | H | H | H | C | N | C | C | C | H | — | H | $CH_3$ | H | 2 | 0.90 | 302.2 | 301.3 |
| B-12 | $CF_3$ | 0 | H | H | H | H | $CH_3$ | C | N | C | C | C | H | — | H | $CH_3$ | H | 2 | 0.88 | 288.1 | 287.3 |
| B-13 | $CF_3$ | 0 | H | H | H | H | $CH_2CH_3$ | C | N | C | C | C | H | — | H | $CH_3$ | H | 2 | 0.94 | 302.2 | 301.3 |
| B-14 | $CF_3$ | 0 | H | $CH_3$ | H | H | $CH_3$ | C | N | C | C | C | H | — | H | $CH_3$ | H | 2 | 0.89 | 302.2 | 301.3 |
| B-15 | $CF_3$ | 0 | H | $CH_3$ | H | H | H | C | N | C | C | C | H | — | H | $CH_3$ | H | 2 | 0.84 | 288.2 | 287.3 |
| B-16 | $CF_3$ | 0 | H | H | H | H | $COCH_3$ | N | C | C | C | C | — | H | H | $CH_3$ | H | 2 | 0.82 | 316.1 | 315.3 |

Table C below provides for each of the exemplified compounds of the formula (A) the structure, the calculated molecular weight (MW) (gram/mol), the observed MS signal (m/z), the HPLC retention time (Rt) in minutes and the number of the HPLC-method as described in paragraph C above ("Analytics: HPLC-Methods") used for analysis. From compound C-43 until the end of Table A the methods by which the compounds are synthesized are identified by referring to the synthetic steps described in the synthesis examples of paragraph B above ("Synthesis Examples").

TABLE C

Formula (C)

(R4 = H, X = CO)

| No | R¹ | D | R⁵ | n | Y⁶ | Y⁷ | Y⁸ | Y⁹ | Y¹⁰ | R¹¹ᵃ | R¹¹ᵇ | R¹¹ᶜ | R¹¹ᵈ | HPLC | Rt | m/z | MW |
|---|---|---|---|---|---|---|---|---|---|---|---|---|---|---|---|---|---|
| C-1 | $CF_3$ | N | H | 2 | C | S | C | C | N | — | H | H | — | 1 | 2.96 | 266.1 | 265.3 |
| C-2 | $CF_3$ | N | H | 2 | C | S | C | C | N | — | H | $CH_3$ | — | 1 | 3.18 | 280.1 | 279.3 |
| C-3 | $CF_2CH_3$ | N | H | 2 | C | S | C | C | N | — | H | H | — | 1 | 2.84 | 262.1 | 261.3 |
| C-4 | $CF_2CH_3$ | N | H | 2 | C | S | C | C | N | — | H | $CH_3$ | — | 1 | 3.06 | 276.1 | 275.3 |
| C-5 | $CF_3$ | CH | H | 3 | N | C | N | C | C | H | — | H | H | 1 | 2.79 | 262.1 | 261.2 |
| C-6 | $CF_3$ | CH | H | 1 | C | N | C | S | C | — | $CH_3$ | — | H | 1 | 3.16 | 265.1 | 264.3 |
| C-7 | $CF_3$ | N | H | 2 | C | N | C | C | N | $CH_3$ | H | H | — | 2 | 0.75 | 263.1 | 262.2 |
| C-8 | $CF_3$ | CH | H | 2 | N | C | N | C | C | $CH(CH_3)_2$ | — | H | H | 1 | 3.07 | 290.1 | 289.3 |
| C-9 | $CF_3$ | CH | H | 2 | N | C | N | C | C | $CH_2CH_3$ | — | H | H | 1 | 2.90 | 276.1 | 275.3 |
| C-10 | $CF_3$ | CH | H | 2 | N | N | N | C | C | — | — | $Y^9$—CH=CH—CH=$Y^{10}$ | | 1 | 3.31 | 299.1 | 298.3 |
| C-11 | $CF_3$ | CH | H | 2 | N | N | N | C | C | — | — | H | H | 1 | 2.61 | 249.1 | 248.2 |
| C-12 | $CF_3$ | CH | H | 2 | C | S | C | C | N | — | $CH_3$ | $CH_3$ | — | 1 | 3.59 | 293.1 | 292.3 |
| C-13 | $CF_3$ | CH | H | 2 | C | N | C | S | C | — | $CH_3$ | — | H | 1 | 2.97 | 280.0 | 279.3 |
| C-14 | $CF_3$ | CH | $CH_3$ | 2 | N | C | N | C | C | H | — | H | H | 2 | 0.77 | 262.1 | 261.2 |
| C-15 | $CF_3$ | N | H | 2 | C | S | C | C | N | — | H | $CONH_2$ | — | 2 | 0.71 | 309.0 | 308.3 |
| C-16 | $CF_3$ | N | H | 2 | C | S | C | C | N | — | CN | H | — | 3 | 0.86 | 291.0 | 290.3 |
| C-17 | $CF_3$ | N | H | 2 | C | S | N | C | N | — | — | N-morpholinyl | — | 1 | 3.00 | 352.1 | 351.4 |
| C-18 | $CF_3$ | CH | H | 2 | N | C | N | C | C | H | — | H | H | 2 | 0.72 | 248.1 | 247.2 |
| C-19 | $CF_3$ | CH | H | 2 | N | C | N | C | C | $CH_3$ | — | H | H | 2 | 0.74 | 262.1 | 261.2 |
| C-20 | $CF_3$ | CH | H | 2 | N | C | N | C | C | H | — | $Y^9$—CH=CH—CH=$Y^{10}$ | | 2 | 0.86 | 298.1 | 297.3 |
| C-21 | $CF_3$ | CH | H | 3 | N | C | N | C | C | $CH_3$ | — | H | H | 2 | 0.78 | 276.1 | 275.3 |
| C-22 | $CF_3$ | N | H | 2 | C | S | C | C | N | — | $CH_2CH_3$ | $CO_2CH_3$ | — | 2 | 0.95 | 352.1 | 351.3 |
| C-23 | $CF_3$ | N | H | 2 | C | S | C | C | N | — | $SO_2NH_2$ | H | — | 2 | 0.52 | 345.1 | 344.3 |
| C-24 | $CF_3$ | N | H | 2 | C | S | C | C | N | — | $NHCH_3$ | $CO_2CH_2CH_3$ | — | 2 | 0.63 | 367.1 | 366.4 |
| C-25 | $CF_3$ | N | H | 2 | C | N | N | C | N | — | $CH_3$ | N-morpholinyl | — | 2 | 0.73 | 349.1 | 348.3 |
| C-26 | $CF_2CHF_2$ | CH | H | 2 | N | C | N | C | C | $CH_2CH_3$ | — | H | H | 2 | 0.79 | 308.2 | 307.3 |
| C-27 | $CF_2CH_3$ | CH | H | 2 | N | C | N | C | C | $CH_2CH_3$ | — | H | H | 2 | 0.74 | 272.1 | 271.3 |
| C-28 | $CF_2Br$ | CH | H | 2 | N | C | N | C | C | $CH_2CH_3$ | — | H | H | 2 | 0.83 | 336.1 | 336.2 |
| C-29 | $CF_2Cl$ | CH | H | 2 | N | C | N | C | C | $CH_2CH_3$ | — | H | H | 2 | 0.82 | 292.1 | 291.7 |
| C-30 | $CF_2CF_3$ | CH | H | 2 | N | C | N | C | C | $CH_2CH_3$ | — | H | H | 2 | 0.88 | 326.1 | 325.3 |
| C-31 | $CF_2CHF_2$ | CH | H | 2 | N | C | N | C | C | $CH(CH_3)_2$ | — | H | H | 2 | 0.83 | 322.1 | 321.3 |
| C-32 | $CF_2CH_3$ | CH | H | 2 | N | C | N | C | C | $CH(CH_3)_2$ | — | H | H | 2 | 0.79 | 286.2 | 285.3 |
| C-33 | $CF_2Br$ | CH | H | 2 | N | C | N | C | C | $CH(CH_3)_2$ | — | H | H | 2 | 0.87 | 352.0 | 350.2 |
| C-34 | $CF_2Cl$ | CH | H | 2 | N | C | N | C | C | $CH(CH_3)_2$ | — | H | H | 2 | 0.86 | 306.1 | 305.8 |
| C-35 | $CF_2CF_3$ | CH | H | 2 | N | C | N | C | C | $CH(CH_3)_2$ | — | H | H | 2 | 0.92 | 340.1 | 339.3 |
| C-36 | $CF_3$ | N | H | 2 | C | N | O | C | N | — | — | cyclopropyl | — | 3 | 0.84 | 291.0 | 290.2 |
| C-37 | $CF_3$ | N | H | 2 | C | N | N | C | N | $CH_3$ | — | $CH_3$ | — | 2 | 0.68 | 278.1 | 277.2 |
| C-38 | $CF_3$ | N | H | 2 | C | N | N | C | N | — | $CH_3$ | N-piperidinyl | — | 2 | 0.88 | 347.2 | 346.4 |
| C-39 | $CF_3$ | N | H | 2 | C | S | C | C | N | — | H | phenyl | — | 2 | 1.05 | 342.1 | 341.4 |
| C-40 | $CF_3$ | N | H | 2 | C | S | C | C | C | — | $SO_2C_2H_5$ | H | H | 2 | 0.88 | 356.4 | 357.0 |
| C-41 | $CF_3$ | N | H | 2 | C | N | N | C | N | — | $CH_3$ | $N(CH_3)_2$ | — | 2 | 0.74 | 306.3 | 307.1 |
| C-42 | $CF_3$ | N | H | 2 | C | N | N | C | N | — | — | $SC_2H_5$ | H | 2 | 0.74 | 310.1 | 309.3 |

(X = CO, R⁴ = H, R⁵ = H)

| No | R¹ | D | n | Y⁶ | Y⁷ | Y⁸ | Y⁹ | Y¹⁰ | R¹¹ᵃ | R¹¹ᵇ | R¹¹ᶜ | R¹¹ᵈ | synth. method |
|---|---|---|---|---|---|---|---|---|---|---|---|---|---|
| C-43 | $CF_3$ | CH | 2 | C | N | N | C | C | $CH_3$ | — | H | H | 7A-C; 6B |
| C-44 | $CHF_2$ | CH | 2 | C | N | N | C | C | $CH_3$ | — | H | H | 7A-C; 2A-D; 6B |
| C-45 | $CF_2Cl$ | CH | 2 | C | N | N | C | C | $CH_3$ | — | H | H | 7A-C; 2A-D; 6B |
| C-46 | $CF_2CH_3$ | CH | 2 | C | N | N | C | C | $CH_3$ | — | H | H | 7A-C; 2A-D; 6B |
| C-47 | $CF_2CHF_2$ | CH | 2 | C | N | N | C | C | $CH_3$ | — | H | H | 7A-C; 2A-D; 6B |
| C-48 | $CF_2CF_3$ | CH | 2 | C | N | N | C | C | $CH_3$ | — | H | H | 7A-C; 2A-D; 6B |
| C-49 | $CF_2Br$ | CH | 2 | C | N | N | C | C | $CH_3$ | — | H | H | 7A-C; 2A-D; 6B |
| C-50 | $CF_3$ | CH | 2 | C | N | N | C | C | $C_2H_5$ | — | H | H | 7A-C; 6B |
| C-51 | $CHF_2$ | CH | 2 | C | N | N | C | C | $C2H_5$ | — | H | H | 7A-C; 2A-D; 6B |
| C-52 | $CF_2Cl$ | CH | 2 | C | N | N | C | C | $C_2H_5$ | — | H | H | 7A-C; 2A-D; 6B |
| C-53 | $CF_2CH_3$ | CH | 2 | C | N | N | C | C | $C_2H_5$ | — | H | H | 7A-C; 2A-D; 6B |
| C-54 | $CF_2CHF_2$ | CH | 2 | C | N | N | C | C | $C_2H_5$ | — | H | H | 7A-C; 2A-D; 6B |

TABLE C-continued

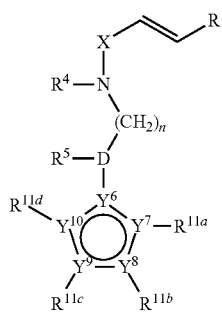

Formula (C)

| | | | | | | | | | | | | | |
|---|---|---|---|---|---|---|---|---|---|---|---|---|---|
| C-55 | CF$_2$CF$_3$ | CH | 2 | C | N | N | C | C | C$_2$H$_5$ | — | H | H | 7A-C; 2A-D; 6B |
| C-56 | CF$_2$Br | CH | 2 | C | N | N | C | C | C$_2$H5 | — | H | H | 7A-C; 2A-D; 6B |
| C-57 | CF$_3$ | CH | 2 | C | N | N | C | C | CH(CH$_3$)$_2$ | — | H | H | 7A-C; 6B |
| C-58 | CHF$_2$ | CH | 2 | C | N | N | C | C | CH(CH$_3$)$_2$ | — | H | H | 7A-C; 2A-D; 6B |
| C-59 | CF$_2$Cl | CH | 2 | C | N | N | C | C | CH(CH$_3$)$_2$ | — | H | H | 7A-C; 2A-D; 6B |
| C-60 | CF$_2$CH$_3$ | CH | 2 | C | N | N | C | C | CH(CH$_3$)$_2$ | — | H | H | 7A-C; 2A-D; 6B |
| C-61 | CF$_2$CHF$_2$ | CH | 2 | C | N | N | C | C | CH(CH$_3$)$_2$ | — | H | H | 7A-C; 2A-D; 6B |
| C-62 | CF$_2$CF$_3$ | CH | 2 | C | N | N | C | C | CH(CH$_3$)$_2$ | — | H | H | 7A-C; 2A-D; 6B |
| C-63 | CF$_2$Br | CH | 2 | C | N | N | C | C | CH(CH$_3$)$_2$ | — | H | H | 7A-C; 2A-D; 6B |
| C-64 | CF$_3$ | CH | 2 | C | N | N | C | C | (CH$_2$)$_2$CH$_3$ | — | H | H | 7A-C; 6B |
| C-65 | CHF$_2$ | CH | 2 | C | N | N | C | C | (CH$_2$)$_2$CH$_3$ | — | H | H | 7A-C; 2A-D; 6B |
| C-66 | CF$_2$Cl | CH | 2 | C | N | N | C | C | (CH$_2$)$_2$CH3 | — | H | H | 7A-C; 2A-D; 6B |
| C-67 | CF$_2$CH$_3$ | CH | 2 | C | N | N | C | C | (CH$_2$)$_2$CH$_3$ | — | H | H | 7A-C; 2A-D; 6B |
| C-68 | CF$_2$CHF$_2$ | CH | 2 | C | N | N | C | C | (CH$_2$)$_2$CH$_3$ | — | H | H | 7A-C; 2A-D; 6B |
| C-69 | CF$_2$CF$_3$ | CH | 2 | C | N | N | C | C | (CH$_2$)$_2$CH$_3$ | — | H | H | 7A-C; 2A-D; 6B |
| C-70 | CF$_2$Br | CH | 2 | C | N | N | C | C | (CH$_2$)$_2$CH$_3$ | — | H | H | 7A-C; 2A-D; 6B |
| C-71 | CF$_3$ | N | 2 | C | N | N | C | C | CH$_3$ | — | H | H | 5A-C; 6B |
| C-72 | CHF$_2$ | N | 2 | C | N | N | C | C | CH$_3$ | — | H | H | 5A-C; 2A-D; 6B |
| C-73 | CF$_2$Cl | N | 2 | C | N | N | C | C | CH$_3$ | — | H | H | 5A-C; 2A-D; 6B |
| C-74 | CF$_2$CH$_3$ | N | 2 | C | N | N | C | C | CH$_3$ | — | H | H | 5A-C; 2A-D; 6B |
| C-75 | CF$_2$CHF$_2$ | N | 2 | C | N | N | C | C | CH$_3$ | — | H | H | 5A-C; 2A-D; 6B |
| C-76 | CF$_2$CF$_3$ | N | 2 | C | N | N | C | C | CH$_3$ | — | H | H | 5A-C; 2A-D; 6B |
| C-77 | CF$_2$Br | N | 2 | C | N | N | C | C | CH$_3$ | — | H | H | 5A-C; 2A-D; 6B |
| C-78 | CF$_3$ | N | 2 | C | N | N | C | C | C$_2$H$_5$ | — | H | H | 5A-C; 6B |
| C-79 | CHF$_2$ | N | 2 | C | N | N | C | C | C$_2$H$_5$ | — | H | H | 5A-C; 2A-D; 6B |
| C-80 | CF$_2$Cl | N | 2 | C | N | N | C | C | C$_2$H$_5$ | — | H | H | 5A-C; 2A-D; 6B |
| C-81 | CF$_2$CH$_3$ | N | 2 | C | N | N | C | C | C$_2$H$_5$ | — | H | H | 5A-C; 2A-D; 6B |
| C-82 | CF$_2$CHF$_2$ | N | 2 | C | N | N | C | C | C$_2$H$_5$ | — | H | H | 5A-C; 2A-D; 6B |
| C-83 | CF$_2$CF$_3$ | N | 2 | C | N | N | C | C | C$_2$H$_5$ | — | H | H | 5A-C; 2A-D; 6B |
| C-84 | CF$_2$Br | N | 2 | C | N | N | C | C | C$_2$H$_5$ | — | H | H | 5A-C; 2A-D; 6B |
| C-85 | CF$_3$ | N | 2 | C | N | N | C | C | CH(CH$_3$)$_2$ | — | H | H | 5A-C; 6B |
| C-86 | CHF$_2$ | N | 2 | C | N | N | C | C | CH(CH$_3$)$_2$ | — | H | H | 5A-C; 2A-D; 6B |
| C-87 | CF$_2$Cl | N | 2 | C | N | N | C | C | CH(CH$_3$)$_2$ | — | H | H | 5A-C; 2A-D; 6B |
| C-88 | CF$_2$CH$_3$ | N | 2 | C | N | N | C | C | CH(CH$_3$)$_2$ | — | H | H | 5A-C; 2A-D; 6B |
| C-89 | CF$_2$CHF$_2$ | N | 2 | C | N | N | C | C | CH(CH$_3$)$_2$ | — | H | H | 5A-C; 2A-D; 6B |
| C-90 | CF$_2$CF$_3$ | N | 2 | C | N | N | C | C | CH(CH$_3$)$_2$ | — | H | H | 5A-C; 2A-D; 6B |
| C-91 | CF$_2$Br | N | 2 | C | N | N | C | C | CH(CH$_3$)$_2$ | — | H | H | 5A-C; 2A-D; 6B |
| C-92 | CF$_3$ | N | 2 | C | N | N | C | C | (CH$_2$)$_2$CH$_3$ | — | H | H | 5A-C; 6B |
| C-93 | CHF$_2$ | N | 2 | C | N | N | C | C | (CH$_2$)$_2$CH$_3$ | — | H | H | 5A-C; 2A-D; 6B |
| C-94 | CF$_2$Cl | N | 2 | C | N | N | C | C | (CH$_2$)$_2$CH$_3$ | — | H | H | 5A-C; 2A-D; 6B |
| C-95 | CF$_2$CH$_3$ | N | 2 | C | N | N | C | C | (CH$_2$)$_2$CH$_3$ | — | H | H | 5A-C; 2A-D; 6B |
| C-96 | CF$_2$CHF$_2$ | N | 2 | C | N | N | C | C | (CH$_2$)$_2$CH$_3$ | — | H | H | 5A-C; 2A-D; 6B |
| C-97 | CF$_2$CF$_3$ | N | 2 | C | N | N | C | C | (CH$_2$)$_2$CH$_3$ | — | H | H | 5A-C; 2A-D; 6B |
| C-98 | CF$_2$Br | N | 2 | C | N | N | C | C | (CH$_2$)$_2$CH$_3$ | — | H | H | 5A-C; 2A-D; 6B |
| C-99 | CF$_3$ | CH | 3 | C | N | N | C | C | CH$_3$ | — | H | H | 7A-C; 6B |
| C-100 | CHF$_2$ | CH | 3 | C | N | N | C | C | CH$_3$ | — | H | H | 7A-C; 2A-D; 6B |
| C-101 | CF$_2$Cl | CH | 3 | C | N | N | C | C | CH$_3$ | — | H | H | 7A-C; 2A-D; 6B |
| C-102 | CF$_2$CH$_3$ | CH | 3 | C | N | N | C | C | CH$_3$ | — | H | H | 7A-C; 2A-D; 6B |
| C-103 | CF$_2$CHF$_2$ | CH | 3 | C | N | N | C | C | CH$_3$ | — | H | H | 7A-C; 2A-D; 6B |
| C-104 | CF$_2$CF$_3$ | CH | 3 | C | N | N | C | C | CH$_3$ | — | H | H | 7A-C; 2A-D; 6B |
| C-105 | CF$_2$Br | CH | 3 | C | N | N | C | C | CH$_3$ | — | H | H | 7A-C; 2A-D; 6B |
| C-106 | CF$_3$ | CH | 3 | C | N | N | C | C | C$_2$H$_5$ | — | H | H | 7A-C; 6B |
| C-107 | CHF$_2$ | CH | 3 | C | N | N | C | C | C$_2$H$_5$ | — | H | H | 7A-C; 2A-D; 6B |
| C-108 | CF$_2$Cl | CH | 3 | C | N | N | C | C | C$_2$H$_5$ | — | H | H | 7A-C; 2A-D; 6B |
| C-109 | CF$_2$CH$_3$ | CH | 3 | C | N | N | C | C | C$_2$H$_5$ | — | H | H | 7A-C; 2A-D; 6B |
| C-110 | CF$_2$CHF$_2$ | CH | 3 | C | N | N | C | C | C$_2$H$_5$ | — | H | H | 7A-C; 2A-D; 6B |
| C-111 | CF$_2$CF$_3$ | CH | 3 | C | N | N | C | C | C$_2$H$_5$ | — | H | H | 7A-C; 2A-D; 6B |

TABLE C-continued

Formula (C)

| | | | | | | | | | | | | | |
|---|---|---|---|---|---|---|---|---|---|---|---|---|---|
| C-112 | CF₂Br | CH | 3 | C | N | N | C | C | C₂H₅ | — | H | H | 7A-C; 2A-D; 6B |
| C-113 | CF₃ | CH | 3 | C | N | N | C | C | CH(CH₃)₂ | — | H | H | 7A-C; 6B |
| C-114 | CHF₂ | CH | 3 | C | N | N | C | C | CH(CH₃)₂ | — | H | H | 7A-C; 2A-D; 6B |
| C-115 | CF₂Cl | CH | 3 | C | N | N | C | C | CH(CH₃)₂ | — | H | H | 7A-C; 2A-D; 6B |
| C-116 | CF₂CH₃ | CH | 3 | C | N | N | C | C | CH(CH₃)₂ | — | H | H | 7A-C; 2A-D; 6B |
| C-117 | CF₂CHF₂ | CH | 3 | C | N | N | C | C | CH(CH₃)₂ | — | H | H | 7A-C; 2A-D; 6B |
| C-11 | CF₂CF₃ | CH | 3 | C | N | N | C | C | CH(CH₃)₂ | — | H | H | 7A-C; 2A-D; 6B |
| C-119 | CF₂Br | CH | 3 | C | N | N | C | C | CH(CH₃)₂ | — | H | H | 7A-C; 2A-D; 6B |
| C-120 | CF₃ | CH | 3 | C | N | N | C | C | (CH₂)₂CH₃ | — | H | H | 7A-C; 6B |
| C-121 | CHF₂ | CH | 3 | C | N | N | C | C | (CH₂)₂CH₃ | — | H | H | 7A-C; 2A-D; 6B |
| C-122 | CF₂Cl | CH | 3 | C | N | N | C | C | (CH₂)CH3 | — | H | H | 7A-C; 2A-D; 6B |
| C-123 | CF₂CH₃ | CH | 3 | C | N | N | C | C | (CH₂)₂CH₃ | — | H | H | 7A-C; 2A-D; 6B |
| C-124 | CF₂CHF₂ | CH | 3 | C | N | N | C | C | (CH₂)₂CH₃ | — | H | H | 7A-C; 2A-D; 6B |
| C-125 | CF₂CF₃ | CH | 3 | C | N | N | C | C | (CH₂)₂CH₃ | — | H | H | 7A-C; 2A-D; 6B |
| C-126 | CF₂Br | CH | 3 | C | N | N | C | C | (CH₂)₂CH₃ | — | H | H | 7A-C; 21A-D; 6B |
| C-127 | CF₃ | N | 3 | C | N | N | C | C | CH₃ | — | H | H | 5A-C; 6B |
| C-128 | CHF₂ | N | 3 | C | N | N | C | C | CH₃ | — | H | H | 5A-C; 2A-D; 6B |
| C-129 | CF₂Cl | N | 3 | C | N | N | C | C | CH₃ | — | H | H | 5A-C; 2A-D; 6B |
| C-130 | CF₂CH₃ | N | 3 | C | N | N | C | C | CH₃ | — | H | H | 5A-C; 2A-D; 6B |
| C-131 | CF₂CHF₂ | N | 3 | C | N | N | C | C | CH₃ | — | H | H | 5A-C; 2A-D; 6B |
| C-132 | CF₂CF₃ | N | 3 | C | N | N | C | C | CH₃ | — | H | H | 5A-C; 2A-D; 6B |
| C-133 | CF₂Br | N | 3 | C | N | N | C | C | CH₃ | — | H | H | 5A-C; 2A-D; 6B |
| C-134 | CF₃ | N | 3 | C | N | N | C | C | C₂H₅ | — | H | H | 5A-C; 6B |
| C-135 | CHF₂ | N | 3 | C | N | N | C | C | C₂H₅ | — | H | H | 5A-C; 2A-D; 6B |
| C-136 | CF₂Cl | N | 3 | C | N | N | C | C | C₂H₅ | — | H | H | 5A-C; 2A-D; 6B |
| C-137 | CF₂CH₃ | N | 3 | C | N | N | C | C | C₂H₅ | — | H | H | 5A-C; 2A-D; 6B |
| C-138 | CF₂CHF₂ | N | 3 | C | N | N | C | C | C₂H₅ | — | H | H | 5A-C; 2A-D; 6B |
| C-139 | CF₂CF₃ | N | 3 | C | N | N | C | C | C₂H₅ | — | H | H | 5A-C; 2A-D; 6B |
| C-140 | CF₂Br | N | 3 | C | N | N | C | C | C₂H₅ | — | H | H | 5A-C; 2A-D; 6B |
| C-141 | CF₃ | N | 3 | C | N | N | C | C | CH(CH₃)₂ | — | H | H | 5A-C; 6B |
| C-142 | CHF₂ | N | 3 | C | N | N | C | C | CH(CH₃)₂ | — | H | H | 5A-C; 2A-D; 6B |
| C-143 | CF₂Cl | N | 3 | C | N | N | C | C | CH(CH₃)₂ | — | H | H | 5A-C; 2A-D; 6B |
| C-144 | CF₂CH₃ | N | 3 | C | N | N | C | C | CH(CH₃)₂ | — | H | H | 5A-C; 2A-D; 6B |
| C-145 | CF2CHF₂ | N | 3 | C | N | N | C | C | CH(CH₃)₂ | — | H | H | 5A-C; 2A-D; 6B |
| C-146 | CF₂CF₃ | N | 3 | C | N | N | C | C | CH(CH₃)₂ | — | H | H | 5A-C; 2A-D; 6B |
| C-147 | CF₂Br | N | 3 | C | N | N | C | C | CH(CH₃)₂ | — | H | H | 5A-C; 2A-D; 6B |
| C-148 | CF₃ | N | 3 | C | N | N | C | C | (CH₂)₂CH₃ | — | H | H | 5A-C; 6B |
| C-149 | CHF₂ | N | 3 | C | N | N | C | C | (CH₂)₂CH₃ | — | H | H | 5A-C; 2A-D; 6B |
| C-150 | CF₂Cl | N | 3 | C | N | N | C | C | (CH₂)₂CH₃ | — | H | H | 5A-C; 2A-D; 6B |
| C-151 | CF₂CH₃ | N | 3 | C | N | N | C | C | (CH₂)₂CH₃ | — | H | H | 5A-C; 2A-D; 6B |
| C-152 | CF₂CHF₂ | N | 3 | C | N | N | C | C | (CH₂)₂CH₃ | — | H | H | 5A-C; 2A-D; 6B |
| C-153 | CF₂CF₃ | N | 3 | C | N | N | C | C | (CH₂)₂CH₃ | — | H | H | 5A-C; 2A-D; 6B |
| C-154 | CF₂Br | N | 3 | C | N | N | C | C | (CH₂)₂CH₃ | — | H | H | 5A-C; 2A-D; 6B |
| C-155 | CF₃ | CH | 1 | C | N | N | C | C | CH₃ | — | H | H | 6B |
| C-156 | CHF₂ | CH | 1 | C | N | N | C | C | CH₃ | — | H | H | 2A-D; 6B |
| C-157 | CF₂Cl | CH | 1 | C | N | N | C | C | CH₃ | — | H | H | 2A-D; 6B |
| C-158 | CF₂CH₃ | CH | 1 | C | N | N | C | C | CH₃ | — | H | H | 2A-D; 6B |
| C-159 | CF₂CHF₂ | CH | 1 | C | N | N | C | C | CH₃ | — | H | H | 2A-D; 6B |
| C-160 | CF₂CF₃ | CH | 1 | C | N | N | C | C | CH₃ | — | H | H | 2A-D; 6B |
| C-161 | CF₂Br | CH | 1 | C | N | N | C | C | CH₃ | — | H | H | 2A-D; 6B |
| C-162 | CF₃ | CH | 1 | C | N | N | C | C | C₂H₅ | — | H | H | 6B |
| C-163 | CHF₂ | CH | 1 | C | N | N | C | C | C₂H₅ | — | H | H | 2A-D; 6B |
| C-164 | CF₂Cl | CH | 1 | C | N | N | C | C | C₂H₅ | — | H | H | 2A-D; 6B |
| C-165 | CF₂CH₃ | CH | 1 | C | N | N | C | C | C₂H₅ | — | H | H | 2A-D; 6B |
| C-166 | CF₂CHF₂ | CH | 1 | C | N | N | C | C | C₂H₅ | — | H | H | 2A-D; 6B |
| C-167 | CF₂CF₃ | CH | 1 | C | N | N | C | C | C₂H₅ | — | H | H | 2A-D; 6B |
| C-168 | CF₂Br | CH | 1 | C | N | N | C | C | C₂H₅ | — | H | H | 2A-D; 6B |
| C-169 | CF₃ | CH | 1 | C | N | N | C | C | CH(CH₃)₂ | — | H | H | 6B |
| C-170 | CHF₂ | CH | 1 | C | N | N | C | C | CH(CH₃)₂ | — | H | H | 2A-D; 6B |
| C-171 | CF₂Cl | CH | 1 | C | N | N | C | C | CH(CH₃)₂ | — | H | H | 2A-D; 6B |

TABLE C-continued

Formula (C)

| | | | | | | | | | | | | |
|---|---|---|---|---|---|---|---|---|---|---|---|---|
| C-172 | CF$_2$CH$_3$ | CH | 1 | C | N | N | C | C | CH(CH$_3$)$_2$ | — | H | H | 2A-D; 6B |
| C-173 | CF$_2$CHF$_2$ | CH | 1 | C | N | N | C | C | CH(CH$_3$)$_2$ | — | H | H | 2A-D; 6B |
| C-174 | CF$_2$CF$_3$ | CH | 1 | C | N | N | C | C | CH(CH$_3$)$_2$ | — | H | H | 2A-D; 6B |
| C-175 | CF$_2$Br | CH | 1 | C | N | N | C | C | CH(CH$_3$)$_2$ | — | H | H | 2A-D; 6B |
| C-176 | CF$_3$ | CH | 1 | C | N | N | C | C | (CH$_2$)$_2$CH$_3$ | — | H | H | 6B |
| C-177 | CHF$_2$ | CH | 1 | C | N | N | C | C | (CH$_2$)$_2$CH$_3$ | — | H | H | 2A-D; 6B |
| C-178 | CF$_2$Cl | CH | 1 | C | N | N | C | C | (CH$_2$)$_2$CH$_3$ | — | H | H | 2A-D; 6B |
| C-179 | CF2CH$_3$ | CH | 1 | C | N | N | C | C | (CH$_2$)$_2$CH$_3$ | — | H | H | 2A-D; 6B |
| C-180 | CF$_2$CHF$_2$ | CH | 1 | C | N | N | C | C | (CH$_2$)$_2$CH$_3$ | — | H | H | 2A-D; 6B |
| C-181 | CF$_2$CF$_3$ | CH | 1 | C | N | N | C | C | (CH$_2$)$_2$CH$_3$ | — | H | H | 2A-D; 6B |
| C-182 | CF$_2$Br | CH | 1 | C | N | N | C | C | (CH$_2$)$_2$CH$_3$ | — | H | H | 2A-D; 6B |
| C-183 | CF$_3$ | N | 1 | C | N | N | C | C | CH$_3$ | — | H | H | 5A-C; 6B |
| C-184 | CHF$_2$ | N | 1 | C | N | N | C | C | CH$_3$ | — | H | H | 5A-C; 2A-D; 6B |
| C-185 | CF$_2$Cl | N | 1 | C | N | N | C | C | CH$_3$ | — | H | H | 5A-C; 2A-D; 6B |
| C-186 | CF$_2$CH$_3$ | N | 1 | C | N | N | C | C | CH$_3$ | — | H | H | 5A-C; 2A-D; 6B |
| C-187 | CF$_2$CHF$_2$ | N | 1 | C | N | N | C | C | CH$_3$ | — | H | H | 5A-C; 2A-D; 6B |
| C-188 | CF$_2$CF$_3$ | N | 1 | C | N | N | C | C | CH$_3$ | — | H | H | 5A-C; 2A-D; 6B |
| C-189 | CF$_2$Br | N | 1 | C | N | N | C | C | CH$_3$ | — | H | H | 5A-C; 2A-D; 6B |
| C-190 | CF$_3$ | N | 1 | C | N | N | C | C | C$_2$H$_5$ | — | H | H | 5A-C; 6B |
| C-191 | CHF$_2$ | N | 1 | C | N | N | C | C | C$_2$H$_5$ | — | H | H | 5A-C; 2A-D; 6B |
| C-192 | CF$_2$Cl | N | 1 | C | N | N | C | C | C$_2$H$_5$ | — | H | H | 5A-C; 2A-D; 6B |
| C-193 | CF$_2$CH$_3$ | N | 1 | C | N | N | C | C | C$_2$H$_5$ | — | H | H | 5A-C; 2A-D; 6B |
| C-194 | CF$_2$CHF$_2$ | N | 1 | C | N | N | C | C | C$_2$H$_5$ | — | H | H | 5A-C; 2A-D; 6B |
| C-195 | CF$_2$CF$_3$ | N | 1 | C | N | N | C | C | C$_2$H$_5$ | — | H | H | 5A-C; 2A-D; 6B |
| C-196 | CF$_2$Br | N | 1 | C | N | N | C | C | C$_2$H$_5$ | — | H | H | 5A-C; 2A-D; 6B |
| C-197 | CF$_3$ | N | 1 | C | N | N | C | C | CH(CH$_3$)$_2$ | — | H | H | 5A-C; 6B |
| C-198 | CHF$_2$ | N | 1 | C | N | N | C | C | CH(CH$_3$)$_2$ | — | H | H | 5A-C; 2A-D; 6B |
| C-199 | CF$_2$Cl | N | 1 | C | N | N | C | C | CH(CH$_3$)$_2$ | — | H | H | 5A-C; 2A-D; 6B |
| C-200 | CF$_2$CH$_3$ | N | 1 | C | N | N | C | C | CH(CH$_3$)$_2$ | — | H | H | 5A-C; 2A-D; 6B |
| C-201 | CF$_2$CHF$_2$ | N | 1 | C | N | N | C | C | CH(CH$_3$)$_2$ | — | H | H | 5A-C; 2A-D; 6B |
| C-202 | CF$_2$CF$_3$ | N | 1 | C | N | N | C | C | CH(CH$_3$)$_2$ | — | H | H | 5A-C; 2A-D; 6B |
| C-203 | CF$_2$Br | N | 1 | C | N | N | C | C | CH(CH$_3$)$_2$ | — | H | H | 5A-C; 2A-D; 6B |
| C-204 | CF$_3$ | N | 1 | C | N | N | C | C | (CH2)$_2$CH$_3$ | — | H | H | 5A-C; 6B |
| C-205 | CHF$_2$ | N | 1 | C | N | N | C | C | (CH$_2$)$_2$CH$_3$ | — | H | H | 5A-C; 2A-D; 6B |
| C-206 | CF$_2$Cl | N | 1 | C | N | N | C | C | (CH$_2$)$_2$CH$_3$ | — | H | H | 5A-C; 2A-D; 6B |
| C-207 | CF$_2$CH$_3$ | N | 1 | C | N | N | C | C | (CH$_2$)$_2$CH$_3$ | — | H | H | 5A-C; 2A-D; 6B |
| C-208 | CF$_2$CHF$_2$ | N | 1 | C | N | N | C | C | (CH$_2$)$_2$CH$_3$ | — | H | H | 5A-C; 2A-D; 6B |
| C-209 | CF$_2$CF3 | N | 1 | C | N | N | C | C | (CH$_2$)$_2$CH$_3$ | — | H | H | 5A-C; 2A-D; 6B |
| C-210 | CF$_2$Br | N | 1 | C | N | N | C | C | (CH$_2$)$_2$CH$_3$ | — | H | H | 5A-C; 2A-D; 6B |
| C-211 | CHF$_2$ | CH | 2 | N | C | N | C | C | CH$_3$ | — | H | H | 2A-D; 6B |
| C-212 | CHF$_2$ | CH | 2 | N | C | N | C | C | C$_2$H$_5$ | — | H | H | 2A-D; 6B |
| C-213 | CHF$_2$ | CH | 2 | N | C | N | C | C | CH(CH$_3$)$_2$ | — | H | H | 2A-D; 6B |
| C-214 | CHF$_2$ | CH | 2 | N | C | N | C | C | (CH$_2$)$_2$CH$_3$ | — | H | H | 2A-D; 6B |
| C-215 | CF$_3$ | CH | 2 | N | C | N | C | C | (CH$_2$)$_3$CH$_3$ | — | H | H | 6B |
| C-216 | CHF$_2$ | CH | 2 | N | C | N | C | C | (CH$_2$)$_3$CH$_3$ | — | H | H | 2A-D; 6B |
| C-217 | CF$_2$Cl | CH | 2 | N | C | N | C | C | (CH$_2$)$_3$CH$_3$ | — | H | H | 2A-D; 6B |
| C-218 | CF$_2$CH$_3$ | CH | 2 | N | C | N | C | C | (CH$_2$)$_3$CH$_3$ | — | H | H | 2A-D; 6B |
| C-219 | CF$_2$CHF$_2$ | CH | 2 | N | C | N | C | C | (CH$_2$)$_3$CH$_3$ | — | H | H | 2A-D; 6B |
| C-220 | CF$_2$CF$_3$ | CH | 2 | N | C | N | C | C | (CH$_2$)$_3$CH$_3$ | — | H | H | 2A-D; 6B |
| C-221 | CF$_2$Br | CH | 2 | N | C | N | C | C | (CH$_2$)$_3$CH$_3$ | — | H | H | 2A-D; 6B |
| C-222 | CF$_3$ | CH | 2 | N | C | N | C | C | CH(CH$_3$)C$_2$H$_5$ | — | H | H | 6B |
| C-223 | CHF$_2$ | CH | 2 | N | C | N | C | C | CH(CH$_3$)C$_2$H$_5$ | — | H | H | 2A-D; 6B |
| C-224 | CF$_2$Cl | CH | 2 | N | C | N | C | C | CH(CH$_3$)C$_2$H$_5$ | — | H | H | 2A-D; 6B |
| C-225 | CF$_2$CH$_3$ | CH | 2 | N | C | N | C | C | CH(CH$_3$)C$_2$H$_5$ | — | H | H | 2A-D; 6B |
| C-226 | CF$_2$CHF$_2$ | CH | 2 | N | C | N | C | C | CH(CH$_3$)C$_2$H$_5$ | — | H | H | 2A-D; 6B |
| C-227 | CF$_2$CF$_3$ | CH | 2 | N | C | N | C | C | CH(CH$_3$)C$_2$H$_5$ | — | H | H | 2A-D; 6B |
| C-228 | CF$_2$Br | CH | 2 | N | C | N | C | C | CH(CH$_3$)C$_2$H$_5$ | — | H | H | 2A-D; 6B |
| C-229 | CF$_3$ | CH | 3 | N | C | N | C | C | CH$_3$ | — | H | H | 6B |
| C-230 | CHF$_2$ | CH | 3 | N | C | N | C | C | CH$_3$ | — | H | H | 2A-D; 6B |
| C-231 | CF$_2$Cl | CH | 3 | N | C | N | C | C | CH$_3$ | — | H | H | 2A-D; 6B |

TABLE C-continued

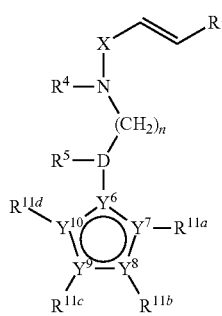

Formula (C)

| | | | | | | | | | | | | | |
|---|---|---|---|---|---|---|---|---|---|---|---|---|---|
| C-232 | CF$_2$CH$_3$ | CH | 3 | N | C | N | C | C | CH$_3$ | — | H | H | 2A-D; 6B |
| C-233 | CF$_2$CHF$_2$ | CH | 3 | N | C | N | C | C | CH$_3$ | — | H | H | 2A-D; 6B |
| C-234 | CF$_2$CF$_3$ | CH | 3 | N | C | N | C | C | CH$_3$ | — | H | H | 2A-D; 6B |
| C-235 | CF$_2$Br | CH | 3 | N | C | N | C | C | CH$_3$ | — | H | H | 2A-D; 6B |
| C-236 | CF$_3$ | CH | 3 | N | C | N | C | C | C$_2$H$_5$ | — | H | H | 6B |
| C-237 | CHF$_2$ | CH | 3 | N | C | N | C | C | C$_2$H$_5$ | — | H | H | 2A-D; 6B |
| C-238 | CF$_2$Cl | CH | 3 | N | C | N | C | C | C$_2$H$_5$ | — | H | H | 2A-D; 6B |
| C-239 | CF$_2$CH$_3$ | CH | 3 | N | C | N | C | C | C$_2$H$_5$ | — | H | H | 2A-D; 6B |
| C-240 | CF$_2$CHF$_2$ | CH | 3 | N | C | N | C | C | C$_2$H$_5$ | — | H | H | 2A-D; 6B |
| C-241 | CF$_2$CF$_3$ | CH | 3 | N | C | N | C | C | C$_2$H$_5$ | — | H | H | 2A-D; 6B |
| C-242 | CF$_2$Br | CH | 3 | N | C | N | C | C | C$_2$H$_5$ | — | H | H | 2A-D; 6B |
| C-243 | CF$_3$ | CH | 3 | N | C | N | C | C | CH(CH$_3$)$_2$ | — | H | H | 6B |
| C-244 | CHF$_2$ | CH | 3 | N | C | N | C | C | CH(CH$_3$)$_2$ | — | H | H | 2A-D; 6B |
| C-245 | CF$_2$Cl | CH | 3 | N | C | N | C | C | CH(CH$_3$)$_2$ | — | H | H | 2A-D; 6B |
| C-246 | CF$_2$CH$_3$ | CH | 3 | N | C | N | C | C | CH(CH3)$_2$ | — | H | H | 2A-D; 6B |
| C-247 | CF$_2$CHF$_2$ | CH | 3 | N | C | N | C | C | CH(CH$_3$)$_2$ | — | H | H | 2A-D; 6B |
| C-248 | CF$_2$CF$_3$ | CH | 3 | N | C | N | C | C | CH(CH$_3$)$_2$ | — | H | H | 2A-D; 6B |
| C-249 | CF$_2$Br | CH | 3 | N | C | N | C | C | CH(CH$_3$)$_2$ | — | H | H | 2A-D; 6B |
| C-250 | CF$_3$ | CH | 3 | N | C | N | C | C | (CH$_2$)$_2$CH$_3$ | — | H | H | 6B |
| C-251 | CHF$_2$ | CH | 3 | N | C | N | C | C | (CH$_2$)$_2$CH$_3$ | — | H | H | 2A-D; 6B |
| C-252 | CF$_2$Cl | CH | 3 | N | C | N | C | C | (CH$_2$)$_2$CH$_3$ | — | H | H | 2A-D; 6B |
| C-253 | CF$_2$CH$_3$ | CH | 3 | N | C | N | C | C | (CH$_2$)$_2$CH$_3$ | — | H | H | 2A-D; 6B |
| C-254 | CF$_2$CHF$_2$ | CH | 3 | N | C | N | C | C | (CH$_2$)$_2$CH$_3$ | — | H | H | 2A-D; 6B |
| C-255 | CF$_2$CF$_3$ | CH | 3 | N | C | N | C | C | (CH$_2$)$_2$CH$_3$ | — | H | H | 2A-D; 6B |
| C-256 | CF$_2$Br | CH | 3 | N | C | N | C | C | (CH$_2$)$_2$CH$_3$ | — | H | H | 2A-D; 6B |
| C-257 | CF$_3$ | CH | 1 | N | C | N | C | C | CH(CH$_3$)C$_2$H$_5$ | — | H | H | 6B |
| C-258 | CHF$_2$ | CH | 1 | N | C | N | C | C | CH(CH$_3$)C$_2$H$_5$ | — | H | H | 2A-D; 6B |
| C-259 | CF$_2$Cl | CH | 1 | N | C | N | C | C | CH(CH$_3$)C$_2$H$_5$ | — | H | H | 2A-D; 6B |
| C-260 | CF$_2$CH$_3$ | CH | 1 | N | C | N | C | C | CH(CH$_3$)C$_2$H$_5$ | — | H | H | 2A-D; 6B |
| C-261 | CF$_2$CHF$_2$ | CH | 1 | N | C | N | C | C | CH(CH$_3$)C$_2$H$_5$ | — | H | H | 2A-D; 6B |
| C-262 | CF$_2$CF$_3$ | CH | 1 | N | C | N | C | C | CH(CH$_3$)C$_2$H$_5$ | — | H | H | 2A-D; 6B |
| C-263 | CF$_2$Br | CH | 1 | N | C | N | C | C | CH(CH$_3$)C$_2$H$_5$ | — | H | H | 2A-D; 6B |
| C-264 | CF$_3$ | CH | 2 | N | C | N | C | C | CH(CH$_3$)C$_2$H$_5$ | — | H | H | 6B |
| C-265 | CHF$_2$ | CH | 2 | N | C | N | C | C | CH(CH$_3$)C$_2$H$_5$ | — | H | H | 2A-D; 6B |
| C-266 | CF$_2$Cl | CH | 2 | N | C | N | C | C | CH(CH$_3$)C$_2$H$_5$ | — | H | H | 2A-D; 6B |
| C-267 | CF$_2$CH$_3$ | CH | 2 | N | C | N | C | C | CH(CH$_3$)C$_2$H$_5$ | — | H | H | 2A-D; 6B |
| C-268 | CF$_2$CHF$_2$ | CH | 2 | N | C | N | C | C | CH(CH$_3$)C$_2$H$_5$ | — | H | H | 2A-D; 6B |
| C-269 | CF$_2$CF$_3$ | CH | 2 | N | C | N | C | C | CH(CH$_3$)C$_2$H$_5$ | — | H | H | 2A-D; 6B |
| C-270 | CF$_2$Br | CH | 2 | N | C | N | C | C | CH(CH$_3$)C$_2$H$_5$ | — | H | H | 2A-D; 6B |
| C-271 | CF$_3$ | CH | 3 | N | C | N | C | C | CH(CH$_3$)C$_2$H$_5$ | — | H | H | 6B |
| C-272 | CHF$_2$ | CH | 3 | N | C | N | C | C | CH(CH$_3$)C$_2$H$_5$ | — | H | H | 2A-D; 6B |
| C-273 | CF$_2$Cl | CH | 3 | N | C | N | C | C | CH(CH$_3$)C$_2$H$_5$ | — | H | H | 2A-D; 6B |
| C-274 | CF$_2$CH$_3$ | CH | 3 | N | C | N | C | C | CH(CH$_3$)C$_2$H$_5$ | — | H | H | 2A-D; 6B |
| C-275 | CF$_2$CHF$_2$ | CH | 3 | N | C | N | C | C | CH(CH$_3$)C$_2$H$_5$ | — | H | H | 2A-D; 6B |
| C-276 | CF$_2$CF$_3$ | CH | 3 | N | C | N | C | C | CH(CH$_3$)C$_2$H$_5$ | — | H | H | 2A-D; 6B |
| C-277 | CF$_2$Br | CH | 3 | N | C | N | C | C | CH(CH$_3$)C$_2$H$_5$ | — | H | H | 2A-D; 6B |
| C-278 | CF$_3$ | CH | 2 | N | C | N | C | C | CH$_3$ | — | CH3 | H | 6B |
| C-279 | CHF$_2$ | CH | 2 | N | C | N | C | C | CH$_3$ | — | CH3 | H | 2A-D; 6B |
| C-280 | CF$_2$Cl | CH | 2 | N | C | N | C | C | CH$_3$ | — | CH3 | H | 2A-D; 6B |
| C-281 | CF$_2$CH$_3$ | CH | 2 | N | C | N | C | C | CH$_3$ | — | CH3 | H | 2A-D; 6B |
| C-282 | CF$_2$CHF$_2$ | CH | 2 | N | C | N | C | C | CH$_3$ | — | CH3 | H | 2A-D; 6B |
| C-283 | CF$_2$CF$_3$ | CH | 2 | N | C | N | C | C | CH$_3$ | — | CH3 | H | 2A-D; 6B |
| C-284 | CF$_2$Br | CH | 2 | N | C | N | C | C | CH$_3$ | — | CH3 | H | 2A-D; 6B |
| C-285 | CF$_3$ | CH | 2 | N | C | N | C | C | C$_2$H$_5$ | — | CH3 | H | 6B |
| C-286 | CHF$_2$ | CH | 2 | N | C | N | C | C | C$_2$H$_5$ | — | CH3 | H | 2A-D; 6B |
| C-287 | CF$_2$Cl | CH | 2 | N | C | N | C | C | C$_2$H$_5$ | — | CH3 | H | 2A-D; 6B |
| C-288 | CF$_2$CH$_3$ | CH | 2 | N | C | N | C | C | C$_2$H$_5$ | — | CH3 | H | 2A-D; 6B |
| C-289 | CF$_2$CHF$_2$ | CH | 2 | N | C | N | C | C | C$_2$H$_5$ | — | CH3 | H | 2A-D; 6B |
| C-290 | CF$_2$CF$_3$ | CH | 2 | N | C | N | C | C | C$_2$H$_5$ | — | CH3 | H | 2A-D; 6B |
| C-291 | CF$_2$Br | CH | 2 | N | C | N | C | C | C$_2$H$_5$ | — | CH3 | H | 2A-D; 6B |

Further examples of specific compounds of the present invention include each of the compounds in table A and table B and their analogues wherein X=SO$_2$ and X=CS and wherein one of Y$^1$, Y$^2$, Y$^3$, Y$^4$ or Y$^5$ is N in form of its pyridine N-oxide such as the N-oxides shown in table D below:

| No | Structure | HPLC | Rt | m/z | MW |
|---|---|---|---|---|---|
| D-1 | 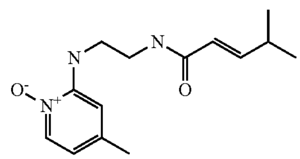 [SMILES: Cc1cc[n+]([O-])c(NCCNC(=O)/C=C/C(C)C)c1] | 2 | 0.74 | 264.1 | 263.3 |
| D-2 | 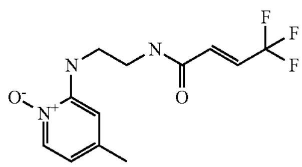 [SMILES: Cc1cc[n+]([O-])c(NCCNC(=O)/C=C/C(F)(F)F)c1] | 2 | 0.74 | 290.1 | 289.3 |
| D-3 | 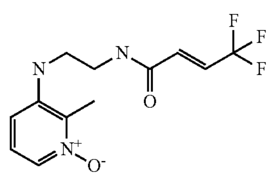 [SMILES: Cc1c(NCCNC(=O)/C=C/C(F)(F)F)ccc[n+]1[O-]] | 2 | 0.68 | 290.1 | 289.3 |
| D-4 | 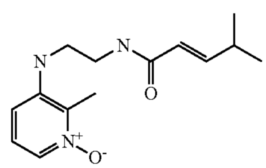 [SMILES: Cc1c(NCCNC(=O)/C=C/C(C)C)ccc[n+]1[O-]] | 2 | 0.69 | 264.1 | 263.3 |

E Biological Examples: Determining Activity Against *Ascaridia galli* and *Oesophagostomum dentatum*

Anthelmintic effects of compounds of this invention were tested in vitro using gut-welling larval stages of two parasitic nematode species: *Ascaridia galli* (intestinal roundworm of chicken), larval stage 3 ("L3"); and *Oesophagostumum dentatum* (nodular worm of swine), larval stages 3 and 4 (respectively "L3" and "L4"). When conducting these experiments, DMSO-solutions of various concentrations of compounds of this invention were prepared and incubated in 96-well microtiter plates. The parasites were then distributed at 20 larvae per well. The anthelmintic effects were classified by microscopic examination. The microscopic examination included assessing mortality, damage, motility, progression of development, and neutral red uptake by the larvae in comparison to a DMSO-control. The anthelmintic effects were defined by the minimum effective concentration ("MEC"), which is the concentration by which at least one of the larvae shows mortality, damage, change in motility, change in progression of development, or no neutral red uptake. The following compounds showed at least some activity against one or more of the nematodes at an MEC of 50 µM or less: A-1-A-25, A-27-A-48, A-51, A-54, A-55, A-57-A-63, A-68-A-100, A-102-A-107, A-115-A-120, A-122-A-124, A-126-A-153, A-155-A-167, A-169-A-187, B-1, B-3-B15, C-1-C-16, C-18-C-24, C-26-C-39, D-2-D4.

DEFINITIONS

The term "alkyl" (alone or in combination with another term(s)) means an acyclic (i.e. straight-chain or branched-chain) or cyclic saturated hydrocarbyl substituent (i.e., a substituent containing only carbon and hydrogen) which unless otherwise specified typically contains from 1 to 6 carbon atoms, and even more typically from 1 to about 4 carbon atoms. Examples of such substituents include methyl, ethyl, n-propyl, isopropyl, n-butyl, iso-butyl, sec-butyl, tert-butyl, pentyl, iso-pentyl, hexyl, and octyl. For instance the term "C$_1$-C$_6$-alkyl" includes but is not limited to methyl, ethyl, n-propyl, isopropyl, cyclopropyl, methylcyclopropyl, n-butyl, iso-butyl, sec-butyl, tert-butyl, cyclobutyl, methylcyclobutyl, n-pentyl, iso-pentyl, neo-pentyl, cyclopentyl, methylcyclopentyl, n-hexyl, iso-hexyl and cyclohexyl. It is noted that "C$_x$-C$_y$" is also denoted as "Cx-Cy" throughout this specification.

Typically preferred alkyl substituents are acyclic alkyl substituents such as acyclic C$_1$-C$_6$alkyl which includes but is not limited to methyl, ethyl, n-propyl, isopropyl, n-butyl, iso-butyl, sec-butyl, tert-butyl, n-pentyl, iso-pentyl, neo-pentyl, n-hexyl and iso-hexyl, more preferred are methyl and ethyl, even more preferred is typically methyl. For R$^1$ cyclic alkyl substituents such as cyclic C$_1$-C$_6$ alkyl are also preferred, however acyclic alkyl substituents such as acyclic C$_1$-C$_6$ alkyl are even more preferred.

The term "alkenyl" (alone or in combination with another term(s)) means a straight- or branched-chain hydrocarbyl substituent containing one or more double bonds and unless otherwise specified typically contains from 2 to 6 carbon atoms, even more typically from 2 to 4 carbon atoms. Examples of such substituents include ethenyl (vinyl); 2-propenyl; 3-propenyl; 1,4-pentadienyl; 1,4-butadienyl; 1-butenyl; 2-butenyl; 3-butenyl; and 2-hexenyl.

The term "alkynyl" (alone or in combination with another term(s)) means a straight- or branched-chain hydrocarbyl substituent containing one or more triple bonds and unless otherwise specified typically from 2 to 6 atoms, even more typically from 2 to 4 carbon atoms. Examples of such substituents include ethynyl, 2-propynyl, 3-propynyl, 1-butynyl, 2-butynyl, 3-butynyl, and 2-hexynyl.

The term "halogen" (alone or in combination with another term(s)) means a fluorine radical ("fluoro", which may be depicted as F), chlorine radical ("chloro", which may be depicted as Cl), bromine radical ("bromo", which may be depicted as Br), or iodine radical ("iodo", which may be depicted as I). Typically, fluoro or chloro is preferred.

The term "alkylsulfoxyl" means an alkyl as defined above bound to an (S=O) group such that if this "alkylsulfoxyl" is bound to, for example, another alkylgroup, a sulfoxide is formed.

When a chemical formula is used to describe a monovalent substituent, the dash on the left side of the formula indicates the portion of the substituent that has the free valence. To illustrate, benzene substituted with —C(O)—OH has the following structure:

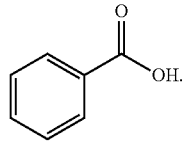

When a chemical formula is used to describe a di-valent (or "linking") component between two other components of a depicted chemical structure (the right and left components), the leftmost dash of the linking component indicates the portion of the linking component that is bound to the left component in the depicted structure. The rightmost dash, on the other hand, indicates the portion of the linking component that is bound to the right component in the depicted structure.

The term "pharmaceutically acceptable" is used adjectivally to mean that the modified noun is appropriate for use in a pharmaceutical product. When it is used, for example, to describe a salt, solvate, N-oxide, active compound or excipient, it characterizes the salt, solvate, N-oxide, active compound or excipient as being compatible with the other ingredients of the composition, and not deleterious to the intended recipient animal, e.g. to the extent that the benefit(s) outweigh(s) the deleterious effect(s).

The above detailed description of preferred embodiments is intended only to acquaint others skilled in the art with the invention, its principles, and its practical application so that others skilled in the art may adapt and apply the invention in its numerous forms, as they may be best suited to the requirements of a particular use. This invention, therefore, is not limited to the above embodiments, and may be variously modified.

The invention claimed is:

1. A compound of the formula (IV) or a pharmaceutically acceptable solvate, N-oxide, or salt thereof,

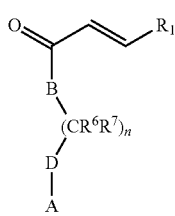

Formula (IV)

wherein $R^1$ is C1-C4 alkyl, wherein each carbon containing radical is optionally substituted by one or more halogen atoms,
$R^6$ is hydrogen, alkyl, phenyl or benzyl,
$R^7$ is hydrogen, alkyl, phenyl or benzyl,
n is 1-3,
B and D are N and,
A is a heteroaryl, chosen from the group consisting of a 6 membered aromate according to formula II and a 5 membered heteroaromate according to formula III,

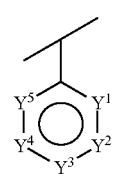

Formula II

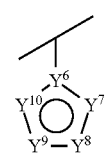

Formula III

Formula II Formula III in formula II:
$Y^1, Y^2, Y^4$ and $Y^5$ may be N or $CR^9$, wherein at least one and at most three of $Y^1, Y^2, Y^4$ and $Y^5$ is N,
$Y^3$ is $CR^{10}$,
$R^9$ is hydrogen, alkyl, alkoxy, alkylthio, halogen, nitrilo, nitro, alkylsulfonyl, alkylcarbonyl, alkoxycarbonyl, aminocarbonyl, alkylaminocarbonyl, dialkylaminocarbonyl, aminosulfonyl, amino, dialkylamino, N-pyrrolidinyl, N-piperidinyl, N-morpholinyl, alkylcarbonylamino, phenyl wherein each of the carbon-containing radicals optionally is substituted by one or more halogen atoms,
$R^{10}$ is hydrogen, alkyl, alkoxy, alkylthio, halogen, nitrilo, nitro, alkylsulfonyl, alkylcarbonyl, alkoxycarbonyl, alkylaminocarbonyl, dialkylaminocarbonyl, aminosulfonyl, N-piperidinyl, N-morpholinyl, alkylcarbonylamino, phenyl wherein each of the carbon-containing radicals optionally is substituted by one or two halogen atoms,
$Y^1$ and $Y^2$ may form a ring system or $Y^2$ and $Y^3$ may form a ring system or $Y^3$ and $Y^4$ may form a ring system or $Y^4$ and $Y^5$ may form a ring system,
and in formula III:
$Y^6$ is N or C,
$Y^7, Y^8, Y^9$ and $Y^{10}$ is $CR^{11}$, $NR^{12}$, O or S, wherein at least one and at maximum three of $Y^7, Y^8, Y^9$ and $Y^{10}$ is $NR^{12}$, O or S,
$R^{11}$ is hydrogen, alkyl, alkylthio, nitrilo, alkoxycarbonyl, aminocarbonyl, alkylsulfonyl, aminosulfonyl, alkylamino, dialkylamino, N-piperidinyl, N-morpholinyl, phenyl, wherein each of the carbon-containing radicals optionally is substituted by one or more halogen atoms,
$R^{12}$ is hydrogen, alkyl or missing,
$Y^7$ and $Y^8$ may form a ring system or $Y^8$ and $Y^9$ may form a ring system.

2. The compound of claim 1, wherein the compound is

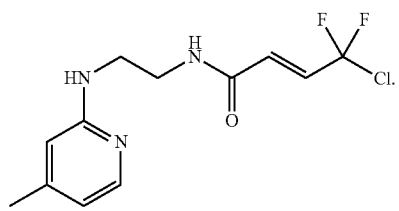 [SMILES: Cc1ccnc(NCCNC(=O)/C=C/C(F)(F)Cl)c1]

3. A method of treating a parasitic infection in an animal comprising administering to the animal, a compound according to claim 1,
for use in the treatment of a parasitic infection of an animal.

4. The method of claim 3, wherein the parasitic infection is a helminth infection.

5. A method of treating a parasitic infection in an animal comprising administering to the animal, a compound according to claim 2.

6. The method of claim 5, wherein the parasitic infection is a helminth infection.

7. An antiparasitic composition comprising one or more compounds of claim 1 and one or more pharmaceutically acceptable excipients.

8. An antiparasitic composition comprising the compound of claim 2 and one or more pharmaceutically acceptable excipients.

* * * * *